United States Patent
Brooks et al.

(10) Patent No.: US 7,165,451 B1
(45) Date of Patent: Jan. 23, 2007

(54) METHODS FOR USING RESONANT ACOUSTIC AND/OR RESONANT ACOUSTO-EM ENERGY TO DETECT AND/OR EFFECT STRUCTURES

(75) Inventors: Juliana H. J. Brooks, Columbus, OH (US); Albert E. Abel, Powell, OH (US)

(73) Assignee: GR Intellectual Reserve, LLC, Havre de Grace, MD (US)

( * ) Notice: Subject to any disclaimer, the term of this patent is extended or adjusted under 35 U.S.C. 154(b) by 0 days.

(21) Appl. No.: 09/786,794

(22) PCT Filed: Sep. 10, 1999

(86) PCT No.: PCT/US99/20776

§ 371 (c)(1), (2), (4) Date: Mar. 8, 2001

(87) PCT Pub. No.: WO00/15097

PCT Pub. Date: Mar. 23, 2000

(51) Int. Cl.
*A61N 7/00* (2006.01)

(52) U.S. Cl. .............................................. 73/579; 601/2

(58) Field of Classification Search ................ 600/427, 600/429, 439; 601/2, 3, 4; 73/579; 607/97, 607/51; 604/22
See application file for complete search history.

(56) References Cited

U.S. PATENT DOCUMENTS

| | | | |
|---|---|---|---|
| 3,280,816 A | 10/1966 | Priore | |
| 3,368,155 A | 2/1968 | Priore | |
| 3,735,755 A | 5/1973 | Eggleton et al. | 128/24 |
| 3,872,443 A | 3/1975 | Ott | 340/172.5 |
| 4,235,243 A | 11/1980 | Saha | 128/740 |
| 4,457,162 A | 7/1984 | Rush et al. | 73/24 |
| 4,538,596 A * | 9/1985 | Colasante | 601/47 |
| 4,622,952 A | 11/1986 | Gordon | 128/1.3 |
| 4,850,959 A * | 7/1989 | Findl | 604/14 |
| 5,188,738 A | 2/1993 | Kaali et al. | 210/748 |
| 5,230,334 A | 7/1993 | Klopotek | 128/399 |
| 5,267,939 A | 12/1993 | Liboff et al. | 600/13 |
| 5,269,746 A | 12/1993 | Jacobson | 600/13 |
| 5,348,002 A | 9/1994 | Caro | 128/633 |
| 5,375,595 A | 12/1994 | Sinha et al. | 600/402 |
| 5,389,790 A | 2/1995 | Honey et al. | 250/342 |
| 5,441,495 A | 8/1995 | Liboff et al. | 600/9 |
| 5,472,441 A | 12/1995 | Edwards et al. | 606/41 |
| 5,520,612 A | 5/1996 | Winder et al. | 601/2 |

(Continued)

FOREIGN PATENT DOCUMENTS

BE          1010049 A3 *   12/1997

(Continued)

OTHER PUBLICATIONS

G. Wade; A Physicist's View of Dr. Rife's Non-Drug Treament and Cure of Microbial Associated Diseases; pp. 1-12; Aug. 1994; Health Freedom News.

(Continued)

*Primary Examiner*—Hezron Williams
*Assistant Examiner*—Rose M. Miller
(74) *Attorney, Agent, or Firm*—Mark G. Mortenson

(57) ABSTRACT

The present invention relates to detection of inorganic and biologic structures and/or disruption and/or augmentation functions of biologic structures using resonant acoustic and/or resonant acousto-EM energy.

40 Claims, 28 Drawing Sheets

U.S. PATENT DOCUMENTS

| | | | | |
|---|---|---|---|---|
| 5,591,913 | A | | 1/1997 | Tucker ........................ 73/628 |
| 5,606,130 | A | | 2/1997 | Sinha et al. ................... 73/627 |
| 5,778,591 | A | * | 7/1998 | Oschman et al. ............ 43/17.1 |
| 5,904,659 | A | * | 5/1999 | Duarte et al. ................... 601/2 |
| 5,908,441 | A | | 6/1999 | Bare ............................. 607/1 |
| 5,908,444 | A | * | 6/1999 | Azure ......................... 607/88 |
| 5,935,516 | A | * | 8/1999 | Baugh ........................... 422/1 |
| 6,221,094 | B1 | | 4/2001 | Bare ............................. 607/1 |

FOREIGN PATENT DOCUMENTS

| | | |
|---|---|---|
| SU | 1534490 A * | 1/1990 |
| WO | WO 9324645 A1 * | 12/1993 |

OTHER PUBLICATIONS

G. Wade; Technical Addendum Article To: A Physicist's View Of Dr. Rife's Non-Drug Treatment And Cure Of Microbial Associated Disease; pp. 1-2; Feb. 1996; Robert Cathey Research Source.

G. Wade; Appendix B: The Intensity Of Ultra Sound Generated In The Upper Surface of The Skin By The Rife Frequency Instrument Which Will Kill A Cancer Tumor; pp. 1-7; Educate-Yourself (originally released Jan. 12, 1993).

G. Wade; Exciting Possibilities In Pulsed Intense Magnetic Field Therapy—A Physicist's View; pp. 1-5; Educate-Yourself (Originally published in Health Freedom News, Aug.-Sep. 1993).

V. Shashlov; On The Mechanism Of Frequency-Selective Giological Effects Of The EHP Radiation And The Ways To Increase Them; pp. 1-4; Radiophysics and Quantum Electronics, vol. 32, No. 1, 1994.

M. Vogel; Information Transfer; pp. 1-2; Physic Research Newsletter; vol. 6, No. 1 Jan.-Feb. 1989.

M. Vogel; Cut Crystals; pp. 1-35; The Lifestream Letter; vol. 4 & 5, Sep.-Dec. 1994.

D. Jones; Daedalus, Inside Stories; p. 519; Dec. 1996; NATURE, vol. 384.

K. A. Fackelmann; Device Sounds Out Salmonella-Infected Eggs; p. 150; Mar. 1992/Science News, vol. 141.

E. Carstensen, et al; Cavitation As A Mechanism For The Biological Effects Of Ultrasound On Plant Roots; pp. 1285-1291; Nov. 1979; Journal of Acoustics Society of America.

S. Child, et al; Growth Of Pea Roots Exposed To Pulsed Ultrasound; pp. 1109-1110; Nov. 1975; Journal of Acoustics Society of America.

F. Eames, et al; Ultrasonic heating of *Vicia faba* roots; pp. 1192-1194; May 1975; Journal of Acoustics Society of America.

S. Barnett, et al; Current Status of Research on Biophysical Effects of Ultrasound; pp. 205-218; Mar. 1994; Ultrasound in Medicine and Biology; vol. 20, No. 3.

P. Chandraratna, et al; Clinical Investigations: High Frequency Ultrasound: Determination of the Lowest Frequency Required for Cellular Imaging and Detection of Myocardial Disease; pp. 1-6; Jan. 1995; American Heart Journal.

W. O'Brien, et al; Mouse Lung Damage from Exposure to 30 kHz Ultrasound; pp. 287-297; Mar. 1994; Ultrasound in Medicine and Biology; vol. 20, No. 3.

A. Tarantal, et al; Ultrasound-Induced Lung Hemorrhage in the Monkey; pp. 65-72; Jan. 1994; Ultrasound in Medicine and Biology; vol. 20, No. 1.

S. Poliachik, et al; Effect of High Intensity Focused Ultrasound On Whole Blood With And Without Microbubble Contrast Agent; pp. 1-18, Figures 1-5; Paper submitted to Ultrasound in Biology and Medicine for publication Nov. 1998.

J. Heckman, et al; Acceleration of Tibial Fracture-Heading by Non-Invasive, Low-Intensity Pulsed Ultrasound; pp. 26-34; Jan. 1994; The Journal of Bone and Joint Injury, vol. 76, No. 4.

I. El'piner; Action of Ultrasonic Waves on Unicellular and Multicellular Organisms; pp. 296-331; 1964; ULTRASOUND-Physical, Chemical, and Biological Effects, Chapter 10 of Book.

Acoustic technique detects chemicals in sealed containers; American Chemical Society.

W. Hedrick et al; Basic Ultrasound Physics; pp. 1-30, Chapter 1; 1995; Ultrasound Physics and Instrumentation, Third Edition.

W. Hedrick, et al; Biological Effects; pp. 249-279, Chapter 12; 1995; Ultrasound Physics and Instrumentation, Third Edition.

F. Dunn; Chapter 140, Introduction; pp. 1699-1701; 1997; Encyclopedia of Acoustics, vol. Four, 1997.

J. Bamber; Chapter 141, Acoustical Characteristics of Biological Media; pp. 1703-1726; 1997; Encyclopedia of Acoustics, vol. Four.

E. Carstensen; Chapter 142, Biological Effects of Ultrasound; pp. 1727-1750; 1997; Encyclopedia of Acoustics, vol. Four.

K. Shung, et al; Chapter 143, Medical Diagnosis With Acoustics; pp. 1739-1750; 1997; Encyclopedia of Acoustics, vol. Four.

J. Greenleaf; Chapter 144, Acoustic Medical Imaging Instrumentation; pp. 1751-1760; 1997; Encyclopedia of Acoustics, vol. Four.

H. von Gierke; Chapter 145, Effects of Vibration and Shock on People; pp. 1761-1779; 1997; Encyclopedia of Acoustics, vol. Four.

W. Tiller; Preface; pp. IX-XII; 1997; Science and Human Transformation.

E. Pecci, Forward; pp. XIII-XIX; 1997; Science and Human Transformation.

W. Tiller; pp. 2-4; 101-138; 189-200; 1997; Science and Human Transformation.

W. Tiller; Foreword; pp. 21-25; 1988; Vibrational Medicine.

R. Gerber; Preface; pp. 31-36; 1998; Vibrational Medicine.

R. Gerber; Chapter III, The Earliest Beginnings of Medical Energetic Approaches: The Birth of Vibrational Medicine; pp. 91-117; 1998; Vibrational Medicine.

The Synergy Between Ultrasound and Cancer Therapy; p. 1; Acoustical Society of America-135th Meeting, Presentation of Abstracts.

R. Lerner, et al; pp. 1064-1067; 1991; Encyclopedia of Physics.

R. Hobbie; pp. vii-ix; 218-224, 246-250; 1997; Intermediate Physics for Medicine and Biology.

C. Polk, et al; Introduction, pp. 27-35, Chapter 1, pp. 99-118; Chapter 2, pp. 121-138, Chapter 5, pp. 197-218; 1986; Handbook of Biological Effects of Electromagnetic Fields.

M. Blank; Preface, pp. xiii-xiv; Chapter 1, pp. 1-10; Chapter 11, pp. 190-223; Chapter 14, pp. 261-275; Chapter 15, pp. 277-285; Chapter 23, pp. 423-436; and Chapter 24, pp. 437-450; 1995; Electromagnetic Fields: Biological Interactions and Mechanisms.

United States Environmental Protection Agency; Executive Summary, pp. 1-1-1-6; Chapter 2, pp. 2-1-2-37; 1990; Evaluation of the Potential Carcinogenicity of Electromagnetic Fields: Review Draft.

B. Lynes; Introduction and Foreword, pp. 1-10; Chapter 13, pp. 87-107; 1997; The Cancer Cure That Worked! Fifty Years of Suppression.

Chou, et al; Auditory perception of radio-frequency electromagnetic fields; pp. 1321-1333; 1982; The Journal of the Acoustical Society of America.

W. Scherer; Biological Effects of Radiofrequenzy Radiation: Application, Hazards, and Safeguards; pp. 1-5; 1994.

K. Kraus, et al; The use of a Cap-Shaped Coil for Transcranial Magnetic Stimulation of the Motor Cortex; pp. 353-362; 1993; The Journal of Clinical Neurophysiology, vol. 10, No. 3.

P. Jennum, et al; Paired transcranial magnetic stimulations and motor evoked potentials; pp. 341-348; 1996.

C. Johnson, et al; Nonionizing Electromagnetic Wave Effects in Biological Materials and Systems; pp. 692-719; 1972; Proceedings of the IEEE, vol. 60, No. 6.

L. Paros, et al; Cranial Electrotherapy Stimulation (CES): A Very Safe and Effective Non-Pharmacological Treatment for Anxiety; pp. 1-12; The Anxiety-Panic internet resource.

J. Raloff; Medicinal EMFs: Harnessing electric and magnetic fields for healing and health; pp. 316-319; Science News, vol. 156.

S. Webb, et al; Inhibition of Bacterial Cell Growth by 136 gc Microwaves; pp. 374-375; 1968; Nature; vol. 218.

S. Webb, et al; Absorption of Microwaves by Microorganisms; pp. 1199-1200; 1969; Nature, vol. 222.

M. Stuchly; Interactions of Electromagnetic Fields with Living Systems; pp. 1-4.

Physical Characteristics and Possible Biological Effects of Microwaves Applied in Wireless Communications; pp. 1-6; 1997; Microwave News—FDA Workshop.

R. Coghill, et al; Extra Low Frequency Electric and Magnetic Fields in the Bedplace of Children Diagnosed with Leukemia: A Case-Control Study; pp. 1-2; 1997; Berner Digest Update, vol. VII, Issue 1.

J. Weaver, et al; Theoretical Limits on the Threshold for the Response of Long Cells to Weak Extremely Low Frequency Electric Fields Due to Ionic and Molecular Flux Rectificion; pp. 1-9; 1998; Biophysical Journal.

M. Jensen; Electromagnetic fields may trigger enzymes; p. 119; 1998; Science News, vol. 153.

Shocking Treatment Proposed for Aids; "Electrocuting" The Aids Virus, A Safer-Yet Blood Supply; Scientists say Electric Current may help fight Aids; 1 Page; News Report.

Plants: Forest Overachievers; 1 Page; 1995; Popular Science.

* cited by examiner

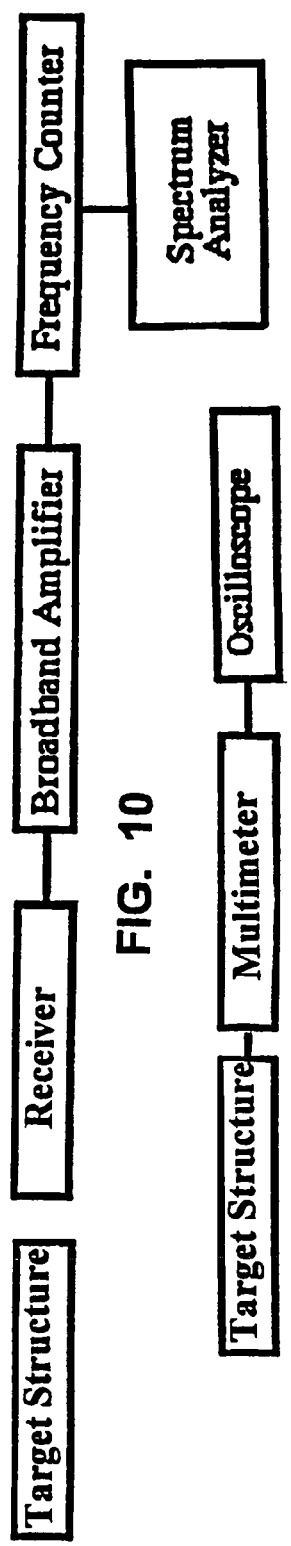
FIG. 10
FIG. 11
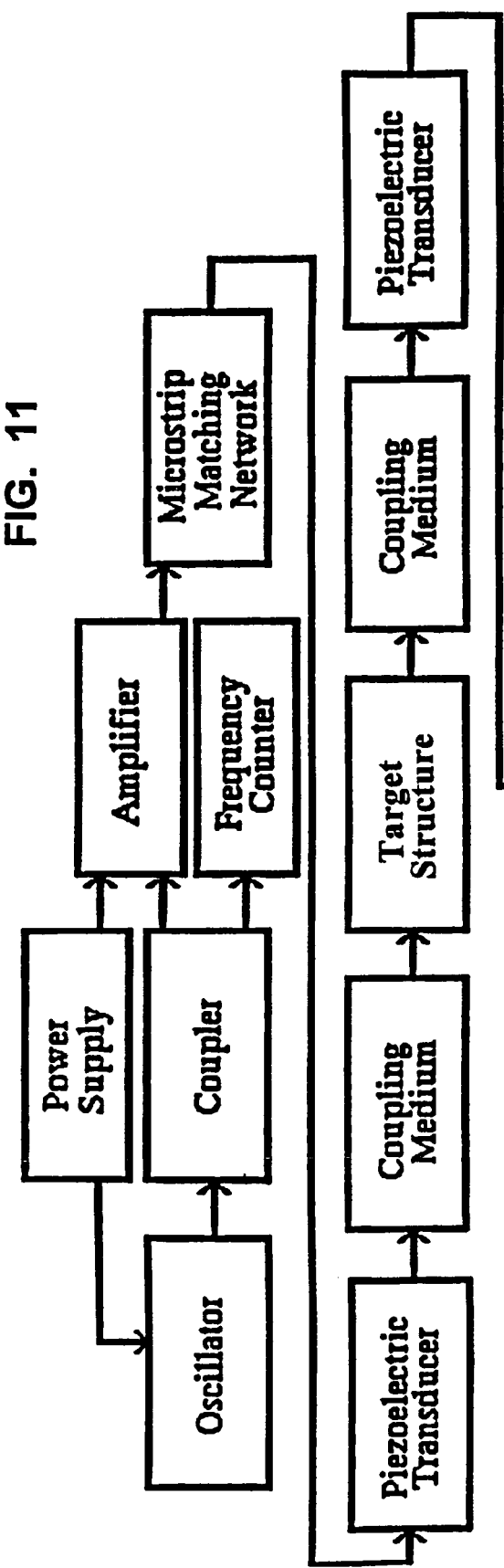
FIG. 12

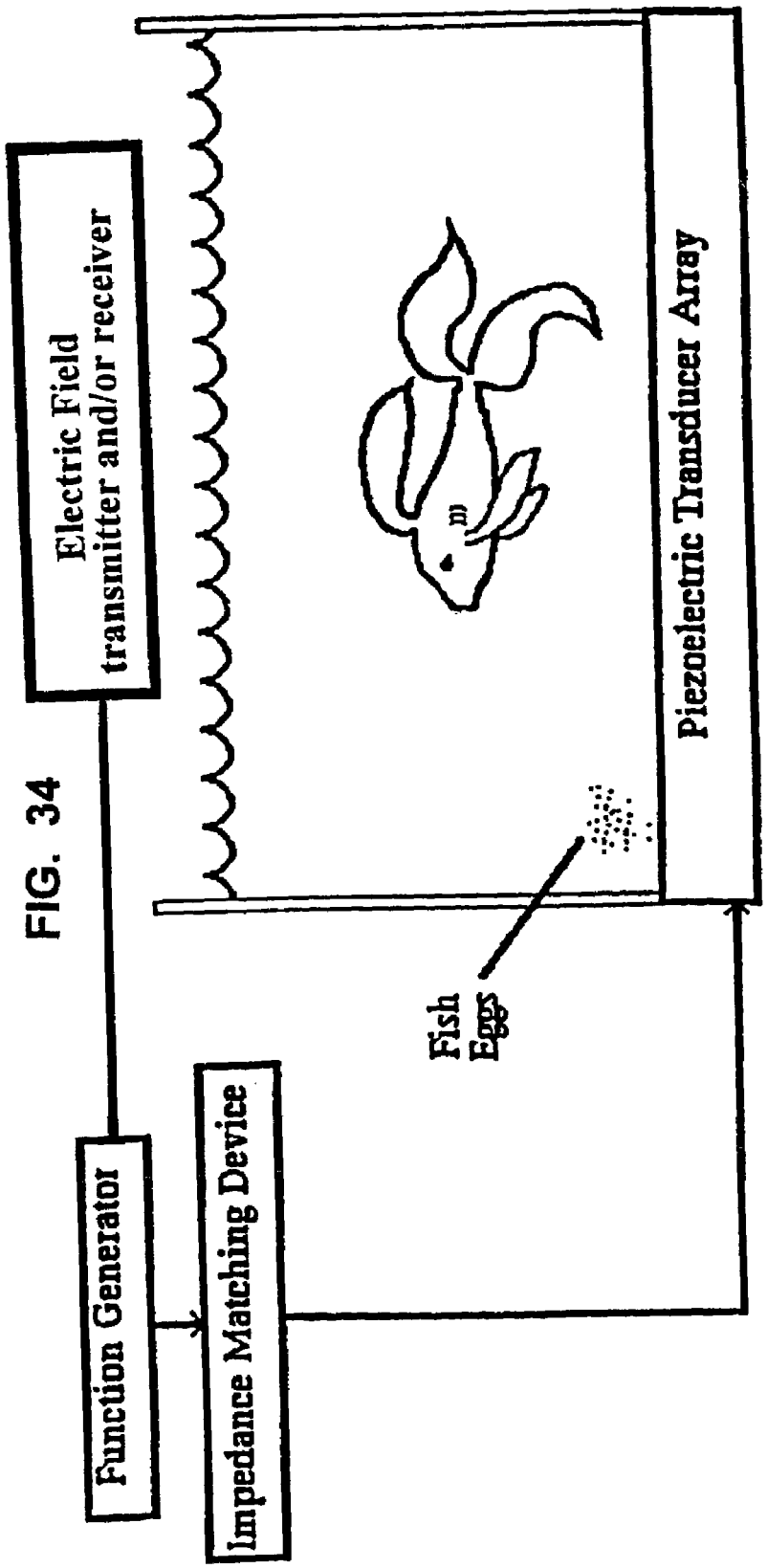

METHODS FOR USING RESONANT ACOUSTIC AND/OR RESONANT ACOUSTO-EM ENERGY TO DETECT AND/OR EFFECT STRUCTURES

TECHNICAL FIELD

The present invention relates to detection of inorganic and biologic structures and/or disruption and/or augmentation of functions of structures using acoustic, resonant acoustic, and/or resonant acousto-EM energy and/or electromagnetic properties and/or fields.

BACKGROUND OF THE INVENTION

The resonant acoustic frequency of a system is the natural free oscillation frequency of the system. A resonant acoustic system can be excited by a weak mechanical or acoustic driving force in a narrow band of frequencies, close or equal to the resonant frequency thereby inducing acoustic resonance in a targeted structure.

Acoustic resonance has been used to determine various properties of solid materials. For instance, Migliori et al in U.S. Pat. Nos. 4,976,148 and 5,062,296 and 5,355,731 disclose a method for characterizing a unique resonant frequency spectroscopic signature for objects derived from ultrasonic excitation of objects, the use of resonant ultrasound spectroscopy for grading production quantities of spherical objects such as roller balls for bearings, and the use of resonant ultrasound spectroscopy with a rectangular parallelpiped sample of a high dissipation material to enable low amplitude resonance to be detected for use in calculating the elastic constants of the high dissipation sample. However, the Migliori patents are directed to solid materials and not to selectively targeting organic or biologic material especially when liquid systems are involved.

In addition to interacting with inanimate structures, acoustic energy also interacts with living, biologic organisms and structures. Acoustic energy has been used extensively in medicine and biology for imaging structures, by directing an acoustic wave at a biologic structure and analyzing the reflection pattern of the acoustic wave. Also, acoustic energy has been used in physical therapy medicine for delivering heat to targeted areas of injury or pain. However, all of the above applications depend on using acoustic energy that is non-selective for the specific targeted biologic structure, and as such, may affect more than just the targeted structure.

Vago, RE., U.S. Pat. Nos. 5,048,520 and 5,178,134 discloses ultrasonic treatment of animals for topical hygiene and antiviral effects. The frequencies disclosed are in the range of 15 kilohertz to 500 kilohertz. They also report that non-enveloped viruses were refractive to the inactivating effects of the ultrasound. The mechanism cited for their antimicrobial effects is "cavitation" on the skin surface only, and they specifically avoid the use of resonant frequencies in their apparatus.

Moasser, M., U.S. Pat. No. 4,646,725 discloses the use of an adaptor for diagnostic ultrasound machines for treatment of skin and mucous membrane lesions caused by infectious agents including herpes virus. The method of treatment was 2.0 to 3.0 minutes at a power output of 1.5 watts per square centimeter, with no specific frequencies being cited. The use of acoustic resonance is not discussed or contemplated.

Johnston, R G., U.S. Pat. No. 5,426,977 discloses ultrasonic measurement of the acoustic resonances in eggs to provide a technique for establishing the presence of *Salmonella* bacteria. Johnson characterizes the eggs and determines the difference between the egg with and without *Salmonella* bacteria. As such, this method does not detect the actual micro-organism, but instead characterizes the vibrational modes of an eggshell, which are modified by the physical presence of a bacteria.

The prior art has failed to suggest a satisfactory method or system for affecting functions of a biologic structure without also affecting near-by tissue. Furthermore, the prior art does not provide for a method that allows precise detection of biologic or inorganic structures using acoustic resonance to produce a signature with high signal to noise ratio, while producing little effect in nearby structures. Still further, use of non-resonant acoustic energy in the prior art affects targeted and non-targeted structures equally.

SUMMARY OF THE INVENTION

For purposes of this invention, the terms and expressions below, appearing in the specification and claims, are intended to have the following meanings:

"Acoustic energy" as used herein is defined as energy that is produced when a physical structure vibrates and the vibrational energy of motion may be transferred to the surrounding medium which includes air, liquid, or solid.

"Detect" as used herein is defined as determining the presence or absence of a structure, and if present identifying the structure.

"Electromagnetic (EM) properties and/or fields" as used herein includes direct and alternating currents, electric and magnetic fields, electromagnetic radiation, and fields which include but are not limited to waves, current, flux, resistance, potential, radiation or any physical phenomena including those obtainable or derivable from the Maxwell equations, incorporated by reference herein.

"Electromagnetic (EM) energy pattern" as used herein represents the electromagnetic energy produced by a structure as acoustic energy interacts with the structure and is manifested as electromagnetic properties and/or fields.

"Biologic structure" as used herein, and used interchangeably with organic, includes anything from the smallest organic or biochemical ion or molecule, to cells, organs, and entire organisms.

"Disruption" as used herein refers to deleterious effects on a structure.

"Acoustic signature" as used herein means a unique acoustic pattern that is produced by the structure when in acoustic resonance that may take the form of amplitude of signal.

"Resonant acoustic frequency" as used herein includes frequencies near or at the natural resonant frequency of the structure including harmonic and subharmonic frequencies of the natural resonant frequency to induce acoustic resonance therein.

"Acousto-EM signature" as used herein is defined as an EM energy pattern of an object in acoustic resonance and/or an EM energy equivalent in frequency to the resonant acoustic frequency.

"Acousto-EM spectroscopy" as used herein is defined as detecting a unique EM signature for a structure that is in acoustic resonance, or detecting a unique acoustic signature from a structure that is in resonance due to the introduction of electromagnetic energy, both of which can be used to detect and/or identify the structure in resonance.

"Living transducer" as used herein is defined as a biologic structure, such as a piezoelectric or semiconductor that converts electromagnetic energy or fields into mechanical energy and/or mechanical energy into electromagnetic energy or fields.

"Cavitation" as described herein is defined as the formation of vapor-filled cavities in liquids, e.g., bubble formation in water when brought to a boil.

"Mechanical" as described herein include mechanisms such as compression and rarefaction which are thought to take place in the intensity/duration threshold region between the thermal and cavitation regions.

"Non-resonant electromagnetic signature" as used herein is defined as an EM energy pattern produced by an object stimulated by a non-resonant acoustic field.

"Resonant acousto-EM energy" as described herein means electromagnetic properties and/or fields that induce acoustic resonance in a structure.

The present invention addresses the shortcomings of the prior art by inducing acoustic resonance in a targeted structure with select frequencies that affect the specific targeted structure but have virtually no effect on nearby, non-resonating structures. Furthermore, acoustic energy power intensities can be reduced by introducing a source of electromagnetic (EM) energy that augments, or replaces, the acoustic energy thereby reducing the destructive nature of high power acoustic energy. The interaction between EM energy and acoustic resonance allows for precise detection of a structure in acoustic resonance by producing a signature with high signal to noise ratio, while producing little effect in other structures.

The present invention provides methods to selectively detect, identify and/or affect an inorganic or biologic structure by using resonant acoustic and/or acousto-EM energy which can transfer useful energy to targeted structures while leaving nearby structures, which are not in resonance, virtually unchanged.

Therefore, it is an object of the present invention to provide a method of identifying or detecting an inorganic or biologic structure using its resonant acoustic and/or acousto-EM signature and/or EM energy patterns.

It is an object of the present invention to provide a method for using resonant acoustic and/or acousto-EM signatures and/or energy patterns to augment and/or disrupt the growth and/or function of biologic structures.

It is another object of the invention to provide a method for determining resonant frequencies of a biologic structure.

It is also an object of the invention to provide a method using resonant acoustic and/or resonant acousto-EM energies to detect the presence of and/or identify biologic structures.

In accordance with the aforesaid objects the present invention provides for the detection of inorganic or biologic structures and/or disruption and/or augmentation of growth and/or functions of said structures using resonant acoustic and/or resonant acousto-EM signatures and/or EM energy patterns.

Applying principles of acoustic resonance, the resonant acoustic frequency of a biologic system is the natural free oscillation frequency of the system, and thus a can be excited by a weak mechanical or acoustic driving force in a narrow band of frequencies.

Also, depending on the size, shape, and composition of the biologic structure, there can be more than one naturally occuring resonant acoustic frequency, as well as numerous subharmonic and superharmonic resonant acoustic frequencies.

When a structure, including both inorganic and biologic structures, goes into acoustic resonance, energy builds up in it rapidly. The energy is either kept in the system or released to the surrounding environment. Energy kept in the structure can enhance the structure's functions or cause disruption of the structure. The energy in a resonant system is either intrinsically dissipated as electromagnetic energy and/or is transmitted as acoustic energy to the nearby medium. The intrinsically dissipated energy is of particular interest, because it is dissipated through molecular and atomic vibrations, producing EM energy patterns. This EM energy is referred to as acousto-EM energy because it is produced when a structure is excited by acoustic energy and some acoustic energy interacts with the structure and is converted into electromagnetic energy thereby being intrinsically dissipated. The properties, fields and/or frequencies of EM energy produced depend on the unique molecular and atomic components of the structure in question. Moreover, the induction of acoustic resonance in a structure leads to the production of a unique acousto-EM signature for that structure, which can be used to detect and/or identify the structure as disclosed in the present invention. Conversely, if a structure is targeted with an applied EM energy equivalent to its acousto-EM signature, the energy dissipation pathway is reversed, and a state of acoustic resonance can be induced. Reversing the energy dissipation pathway with an applied acousto-EM signature can be used to produce the same augmentation, detection, and disruption effects that the original resonant acoustic energy field produces. An applied acousto-EM signature can be used either by itself, or in combination with resonant acoustic energy. Using the applied resonant acousto-EM signature and resonant acoustic energy together, allows for the use of lower power levels of both types of energy, lessening the potential adverse affects of electromagnetic energy and/or acoustic energy on nearby or adjacent nontargeted structures.

Electromagnetic energy may also interact with and complement an acoustic energy wave in a system in at least four ways: via the piezoelectric effect, intrinsic dissipation of electromagnetic energy and via the acoustoelectric or magnetoacoustic effect.

In the piezoelectric effect, acoustic vibratory energy is converted interchangeably with EM energy by a transducer. Biologic piezoelectric structures can modulate the same conversion of energy, thereby acting as living transducers. Thus, when an EM field is applied to a biologic piezoelectric structure, an acoustic wave is produced. Likewise, when an acoustic wave is applied to a biologic piezoelectric structure, EM energy is produced. The piezoelectric effect in biologic structures has many useful applications (see below.) This effect becomes even more useful when principles of acoustic resonance are applied. In the present invention specific biologic structures can be targeted with an acoustic wave or EM energy at power levels that dramatically affect the target structure, but have virtually no effect on adjacent, nonresonant structures. Although not previously postulated by others, biologic structures functioning as living, resonant piezoelectric transducers which modulate the conversion of mechanical and EM energy is undoubtedly one of the major underlying mechanisms responsible for the interaction of EM fields with biologic structures.

In the acoustoelectric effect, the passage of an acoustic wave through a semiconductor induces an electric current. The passage of an acoustic wave through the material is postulated to cause a periodic spatial variation of the potential energy of the charge carriers. This results in an electric field across the ends of the semiconductor as long as the acoustic wave is traversing the semiconductor. Free electron carriers are bunched in the potential-energy troughs, and as the acoustic wave having a specific frequency propagates, it drags the bunches along with it, resulting in an electric field such as a DC field pulsing at the specific acoustic frequency or an AC field having a frequency equal to the specific acoustic frequency. The effect is enhanced where there are both positively and negatively charged carriers, and where there are many different groups of carriers—conditions which are frequently found in biologic systems. The attributes of the current produced depend on the unique molecular and atomic components of the structure in question. This aspect alone provides a means to perform acoustoelectric spectroscopy on biologics many of which are semiconductors, and depending on the selected frequency, the acoustoelectric effect in biological structures has many other potentially useful applications. Thus understood, a targeted structure can be irradiated or exposed to acoustic energy having non-resonant frequency and an electromagnetic energy pattern of the acoustoelectric effect in the structure can be detected. This detected non-resonant electromagnetic signature can be used as a signature to affect, detect and identify the targeted structure.

However, the accustoelectric effect becomes even more useful when principles of acoustic resonance are applied. Augmentation, detection, and/or disruption of biologics can be targeted to specific structures at power levels that dramatically affect the target structure, but have virtually no effect on nearby, nonresonant structures. The current produced by the acoustoelectric effect in a resonant structure will be much stronger than any current produced by neighboring non-resonant structures, and may be of an alternating nature. The large signal to noise ratio obtained from a resonant structure improves accuracy of acoustic and EM energy pattern identification and detection. Similar to reversal of the piezoelectric effect and acoustic resonance intrinsic energy dissipation pathway (see above), application of the resonant acoustoelectric EM energy pattern to a targeted structure will amplify the acoustic wave (acoustoelectric gain which peaks at the frequency for which the acoustic wavelength is the Debye length, where bunching is optimum). Thus, combined use of the resonant acoustic, acoustoelectric and/or EM fields permit greater tissue penetration of high frequency acoustic energy that would otherwise be highly attenuated and have poor tissue penetration. Using the resonant acoustic frequency, acoustoelectric and/or EM fields together also allows for the use of lower power levels of these types of energy, lessening the potential effects on other nontargeted and nonresonant structures.

The magnetoacoustic effect is the magnetic-field-dependent attenuation of an acoustic field in a monotonic, oscillatory, or resonant manner, depending on the electronic properties of the substance in question. This variability in result, depending on structural composition, provides a further enhancement of acousto-EM spectroscopy in relation to biologics and other structures, via addition of a magnetic field. Also, the addition of a magnetic field provides the means to amplify or attenuate an acoustic field, thus improving or modulating the penetration of the acoustic field in biologic tissues.

Similarly, resonant acoustics combined with acoustic cyclotron resonance (ie. resonant acoustic cyclotron resonance) and Doppler-shifted resonant acoustic cyclotron resonance presents a powerful, and precise means of selectively causing augmentation, detection and/or disruption of structures.

The present invention provides a method that applies the principles of acoustic resonance to biologic structures for the purpose of disruption and/or augmentation of functions of the specifically targeted biologic structure. The resonant acoustic frequency of a biologic structure may be determined by performing resonant acoustic spectroscopy using methods and systems well know in the art. Particularly, a resonant acoustic frequency of a biologic structure may by determined by the steps of:

a) applying acoustic energy to the biologic structure and scanning through a range of acoustic energy frequencies; and b) detecting at least one specific frequency which causes a maximum signal output from the biologic structure indicating the biologic structure being induced into acoustic resonance by the at least one specific frequency.

The specific frequencies causing the maximum signals are the resonant acoustic frequencies of the biologic structure which are defined and used herein as the acoustic signature of the biologic structure. Once determined, at least one resonant acoustic frequency may be applied to the biologic structure to affect functioning therein and/or to determine its acousto-EM signature.

The acoustic energy, including the resonant acoustic frequencies (i.e., the acousto-EM signature) may be applied at a power level sufficient to affect functioning of the biologic structure. Depending on the power intensity of the acoustic energy, and the type of targeted structure that is induced into acoustic resonance, the structure may have its functions affected, such as disruption and/or augmentation.

At lower power levels functions of the biologic structure can be augmented while at higher power levels disruption of the structure may occur. Augmentation as used herein encompasses beneficial effects on the biologic structure. Such augmenting of functions or enhancing effects include but are not limited to enhancement of growth, reproduction, regeneration, embryogenesis, metabolism, fermentation, and the like. The results of such enhancement include but are not limited to increase in bone mass or density, increase in number and maturation of eggs, increase in number and/or function of leukocytes, increase in fermentation products in beer, wine and cheese manufacturing, increase in plant germination and growth and the like.

There are some situations where the ability to selectively disrupt a structure with acoustic resonance is very useful as disclosed in the present invention. As stated above, disruption as used herein refers to deleterious effects on the biologic structure. Such deleterious effects include but are not limited to structural failure of the biologic structure resulting in lysis, shattering, rupture or inactivation of the biologic or of one or more components of the biologic structure. Disruption as used herein also includes within its ambit inhibition of vital processes required for growth, reproduction, metabolism, infectivity and the like. Components which may be targeted for disruption include, but are not limited to DNA, RNA, proteins, carbohydrates, lipids, lipopolysaccharides, glycolipids, glycoproteins, proteoglycans, chloroplasts, mitochondria, endoplasmic reticulum, cells, organs and the like. In the case of virulent organisms, the virulence factors may be specifically targeted for disruption to prevent or inhibit the growth, infectivity or virulence of the organism. Such virulence factors include but are not limited to endotoxins, exotoxins, pili, flagella, proteases, ligands for host cell receptors, capsules, cell walls, spores, chitin, and the like.

Organics, biologics or one or more targeted portions thereof which are amenable to disruption using the methods of the present invention include but are not limited to viruses, bacteria, protozoans, parasites, fungi, worms, mollusks, arthropods, tissue masses, and the like. The organics or biologics to be disrupted may be isolated, present in a multicellular organism or portion thereof, or other complex environment.

It is postulated that disruption of the targeted biologic structure without affecting nearby tissue or structures occurs due to acoustic resonance being induced only in the targeted structure which until now has not been considered a mechanism to affect a biologic structure. This is very different from that disclosed in the prior art which contemplates only three mechanisms for affecting a biologic structure which include cavitation, thermal and mechanical.

At specific power levels, such as in lower levels, that do not cause the actual disruption of a structure, resonant acoustic energy can intrinsically dissipate within the structure. This intrinsically dissipated acoustic energy can be converted by the structure into an electromagnetic energy having specific properties and/or fields that may be manifested as direct and alternating currents, electric and magnetic fields, electromagnetic radiation and the like. The pattern of the electromagnetic energy represents a produced acousto-EM signature of the structure.

The present invention provides a method to determine an acousto-EM signature of a structure which comprises irradiating the structure with acoustic energy having a frequency at or near a previously determined resonant acoustic frequency of the structure to induce resonance therein and detecting the electromagnetic energy pattern caused by the intrinsic dissipation of energy.

Once an acousto-EM signature is determined for a specific structure, this structure can be induced into acoustic resonance by applying an EM energy pattern or equivalent to the acousto-EM signature of the structure. Typical electromagnetic energies applied include direct and alternating current, electric and magnetic fields, and electromagnetic radiation and the like.

As such, the present invention applies the principles of acoustic resonance by applying resonant acoustic frequencies and electromagnetic energy equivalent to the predetermined acousto-EM signature of a targeted structure individually, or in combination, to affect the targeted structure, the method comprising the steps of:

a) applying at least one resonant acoustic frequency of the targeted structure; and/or b) applying electromagnetic energy equivalent to part or all of the acousto-EM signature of the targeted structure; and c) applying (a) and/or (b) each at a power intensity level to induce acoustic resonance within the targeted structure and affect functioning of the structure.

Either the resonant acoustic frequency of the targeted structure or the acousto-EM signature must be predetermined, as discussed above, to provide the applicable energy for inducing acoustic resonance in the structure. The electromagnetic energy can be introduced into the targeted structure in the form of a direct or alternating current having a specific frequency that is equivalent to the electromagnetic energy pattern (i.e., the acousto-EM signature) detected when the structure is induced into acoustic resonance. Furthermore each type of energy can be applied at a power level less than used individually and this allows for inducing acoustic resonance in the structure with the possibility of reducing damage to the structure.

The present invention provides a method for detecting and/or identifying inorganic or biologic structures using resonant acoustic and/or acousto-EM energy. The method includes determining the acoustic signature of a structure by irradiating the structure with a range of frequencies to determine the specific frequency and/or frequencies that induce acoustic resonance therein to provide an acoustic signature of the structure. The acoustic signature can be compared with reference signatures to detect and/or identify the structure.

Furthermore, the identification and/or detection of a structure can also be achieved by detecting an acousto-EM signature of a targeted structure, the method comprising the steps of:

a) inducing acoustic resonance in the targeted structure; and b) detecting an electromagnetic energy pattern from the targeted structure in acoustic resonance which represents an acousto-EM signature of the structure.

The acousto-EM signature can be compared to reference signatures to detect and/or identify the structure.

The targeted structure can be induced into acoustic resonance by introducing acoustic energy including at least one resonant acoustic frequency, electromagnetic energy equivalent to the resonant acoustic frequency, and/or an electromagnetic energy pattern equivalent to the acousto-EM signature.

The electromagnetic energy pattern manifested as electromagnetic properties and fields may be determined by detection means well known to those skilled in the art such as those disclosed in *Introduction to Electromagnetic Fields and Waves*, by Erik V. Bohn Addison-Wesley Publishing Co., 1968, the contents of which are incorporated by reference herein.

In another embodiment of the present invention, a structure may be induced into acoustic resonance by applying to the structure part or all of the acousto-EM signature of the structure to induce the structure into acoustic resonance. If the structure is induced into acoustic resonance, this fact may be used to detect and/or identify the structure. This represents another method of the present invention that may used for identification or detection of a specific structure, because each structure will not only have its own unique acoustic signature but also will have a unique acousto-EM signature to which it responds by resonating acoustically. Also, depending on the power intensity of the electromagnetic properties and/or fields and the type of targeted structure that is induced into acoustic resonance, the structure may have its functions affected, such as disruption and/or augmentation.

In all the above embodiments the introduction of acoustic and/or electromagnetic energy including a resonant acoustic frequency can be applied in either continuous and/or periodic form depending on the desired effect.

The acoustic and/or EM energy or fields may be applied individually or in combination. Likewise the acoustic and/or EM energy or fields may be detected individually or in combination.

Many biochemical compounds and biologic structures are naturally occurring crystals and especially susceptible in that regard to the effects of resonant acoustic energy. Many biologic substances are piezoelectric materials. For instance, bone is a piezoelectric material and the piezoelectric properties of bone play a vital role in its biological functions. As such, it is further envisioned by the inventors that biologic structures having a piezoelectric nature may be affected by applying a sufficient amount of acoustic energy and/or electromagnetic energy to induce the structure into resonance thereby affecting the functions of the biologic structure either positively or negatively. Thus understood, biologic structures that act as living transducers may be induced into acoustic resonance by introducing electromagnetic energy equivalent to a resonant acoustic frequency of the biologic structure which is converted to mechanical energy by the living transducer thereby inducing acoustic resonance in the structure.

Another aspect of the invention is a system for detecting a biologic or inorganic structure by determining the resonant acoustic and/or acousto-EM signature of the structure comprising;

a) means for inducing acoustic resonance in the biologic or inorganic structure;

b) means for detecting the acoustic signature of the biologic or inorganic structure; and c) means for comparing the acoustic signature of the biologic or inorganic structure with a reference acoustic signature of the structure.

Also, the above system may also or instead comprise means for detecting a resonant acousto-EM energy signature of the structure in acoustic resonance which produces an electromagnetic energy pattern such as described above. The acousto-EM signature can be compared with a previously determined reference acousto-EM signature by providing means for comparing in a detection or identification system. The electromagnetic energy pattern is manifested as electromagnetic properties and/or fields that include but are not limited to energy in the form of direct and alternating current, electric and magnetic fields, and electromagnetic radiation. The targeted structure can be induced into acoustic resonance by introducing acoustic energy including at least one resonant acoustic frequency, electromagnetic energy equivalent to the resonant acoustic frequency, and/or an electromagnetic energy pattern equivalent to the acousto-EM signature.

In another embodiment of the present invention a system for augmenting and/or disrupting a targeted biologic structure comprises means for applying acoustic energy including a previously determined resonant acoustic frequency to induce acoustic resonance in the biologic structure, the acoustic energy being applied at a sufficient power input to affect functions of the biologic structure. Alternatively, the targeted structure may be induced into acoustic resonance by providing electromagnetic energy equivalent to the resonant acoustic frequency or the acousto-EM signature that was previously determined, such electromagnetic energy including direct and alternating current, electric and magnetic fields, and electromagnetic energy.

In yet another embodiment a system is provided to introduce acoustic energies having acoustic frequencies at or near the resonant acoustic frequencies of the targeted structure and also electromagnetic energy to augment the resonant acoustic frequencies comprising:

means for introducing a frequency at or near the resonant acoustic frequency of the targeted structure; and means for introducing electromagnetic energy equivalent to the electromagnetic energy pattern previously determined as an acousto-EM signature of the structure, such means including direct and alternating current, electric and magnetic fields, and/or electromagnetic radiation and the like.

The acoustic energy and EM energy equivalent to the acousto-EM signature may be applied and/or detected by a single means that can apply both types of energy.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

Other objects, features and many of the advantages of the invention will be better understood upon a reading of the following detailed description when considered in connection with the accompanying drawings wherein:

FIG. 10 is a block schematic of detection of electromagnetic radiation emitted from a biologic structure.

FIG. 11 is a block schematic of detection of direct and alternating current in a biologic structure.

FIG. 12 is a block schematic showing a method for determining resonant acoustic frequencies of viruses.

FIG. 34 is a block schematic showing a method for augmenting the growth rate of multicellular organisms using resonant acoustic and/or acousto-EM energy.

DETAILED DESCRIPTION OF THE
PREFERRED EMBODIMENTS

Figure 1:
FIG. 1 is a block schematic of a basic Acoustic Energy Generating System.

The methods of the present invention comprise delivering acoustic energy at resonant frequencies to an inorganic or biologic structure as shown in FIG. 1. Using methods known to those skilled in the art, any device capable of generating and transmitting acoustic energy through any medium can be used to generate the resonant acoustic frequencies utilized by the invention. This includes, but is not limited to, devices that produce acoustic energy using traditional EM stimulation of piezoelectric transducers, (man-made or naturally occurring), purely mechanical devices (such as high frequency air whistles), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator, also called signal generator or function generator, that produces a signal with predetermined characteristics such as frequency, mode, pulse duration, shape, and repetition rate may be utilized to generate the resonant acoustic frequencies utilized by the invention. Various oscillators or signal generators can be commercially purchased for frequencies ranging from Hertz to Gigahertz, such as the MicroLambda LMOS series (500 MHz–18 GHz), the BK Precision 2005A (100 KHZ–450 MHz) (B&K Precision, Chicago, Ill.), the Tektronix SMEO2 (5 KHZ–5 GHz), and the Tektronix 25 SME 4040 (0.5 Hz–20 MHz) (Tektronic, Inc., Beaverton, Oreg.), and the Matec 700 series (1–1100 MHz) and the like.

The frequency at which resonance occurs depends on the size, shape, and composition of a structure. For instance, the resonant frequency of a sphere is the frequency at which the acoustic wavelength is equal to the sphere diameter. A more complex structure—a cylinder—has two resonant frequencies based on two axes of orientation, with one of the resonant frequency wavelengths being equal to 1.5 times the length. The more complex the shape of the structure, the more complex the resonant acoustic frequency pattern, however, the wavelength at which acoustic resonance occurs is roughly equivalent to the size of the structure.

The frequency which matches a particular acoustic wavelength depends on the composition of the structure, according to the equation:

$$\text{velocity} = \text{frequency} \times \text{wavelength} \quad (1)$$

where velocity refers to the speed of the acoustic wave propagation (the speed of sound) in the medium composing the structure. Although the speed of sound varies among various biological tissues, it is roughly equivalent to the speed of sound in water (1,500 m/s), because most biologic organisms are composed chiefly of water. Using the speed of sound in water as the velocity of the acoustic wave, and using the structure size as the rough equivalent of the wavelength, the approximate range of resonant acoustic frequencies in organic or biologic structures, is given by:

$$\text{Frequency} = \frac{\text{Velocity}}{\text{Wavelength}} = \frac{\text{Velocity}}{\text{Size}} = \frac{1{,}500 \text{ m/s}}{\text{Size}} \quad (2)$$

(See the chart that follows.)

Other known speeds of sound in biologic tissues vary and include:

(1) liver (1550 n/s); (2) muscle (1580 n/s); (3) fat (1459 n/s); (4) brain (1560 m/s); (5) kidney (1560 m/s); (6) spleen (1570 m/s); (7) blood (1575 m/s); (8) bone (4080 n/s); (9) lung (650 m/s); (10) lens of eye (1620 m/s); (11) aqueous humor (1500 m/s); and (12) vitreous humor (1520 m/s). Resonant acoustic frequency ranges for targeted organic or biologic structures comprised of tissues with acoustic velocities different from the speed of sound in water, are derived using the same equation (velocity/wavelength) and correlate to the charted ranges listed below, plus or minus, depending on the speed of sound in the targeted tissue.

Although velocity of acoustic energy in a particular medium is for the most part constant, there is a slight dependence of velocity on frequency—an effect called dispersion. For example, over the frequency range of 1 to 20 MHz, the acoustic velocity changes by 1%. Thus, in the present invention the resonant frequency(s) or at least the range of frequencies within which the resonant frequency can be found for a targeted structure depend on its size, shape, and composition, and the specific frequency range under examination. Some approximate acoustic resonant frequencies for biologic structures are included in the following Table 1.

TABLE 1

Approximate Acoustic Resonant Frequency Ranges for Biologic Structures
(Speed of sound = 1,500 m/s)

| Size | Structure | Frequency | Range |
|---|---|---|---|
| 10 m | whales | 150 Hz | *Hertz |
| 1 m | humans | 1.5 kHz | *KiloHertz |
| 1 dm | hamster | 15 kHz | |
| 1 cm | beetle | 150 kHz | |
| 1 mm | lice | 1.5 MHz | *MegaHertz |
| 100 um | plant cells | 15 MHz | |
| 10 um | animal cells | 150 MHZ | |
| 1 um | bacteria | 1.5 gHz | *GigaHertz |
| 100 nm | viruses | 15 gHz | |
| 10 nm | proteins | 150 gHz | |
| 1 nm | small molecules | 1.5 tHz | *TerraHertz |

To obtain the maximum transfer of acoustical energy from one medium to another, the characteristic acoustical impedance of each should be as nearly equal to the other as possible. This problem of impedance matching, as it is termed, occurs in many branches of physics, and is employed in acoustical techniques, as a means of matching two media of different acoustical impedances $R_1$ and $R_2$ respectively. The matching medium is sandwiched between the other two and should be the appropriate thickness relative to the wavelength of the sound transmitted, and its acoustical impedance R should be nearly equal to $\sqrt{(R_1 R_2)}$. An impedance matching device that is commercially available and which can be utilized in this invention includes Model 60, manufactured by Matec Instruments, Inc.

Acoustic energy can be produced by a transducer that converts received electromagnetic energy into rapid, physical vibrations, and thus acoustic energy. The first acoustic transducers used the piezoelectric properties of naturally occurring quartz to produce acoustic energy waves.

EM energy→piezoelectric transducer→acoustic energy waves

New transducers use materials such as ferroelectric ceramics (barium titanate, lead titanate, or lead zirconate) and zinc oxide. Recent advances in materials engineering have also produced piezoelectric polymers which can be shaped into sheets and cords, allowing a multiplicity of applications.

Transducers are also commercially available from a wide variety of manufacturers, in a wide variety of designs which can be configured to particular applications and frequencies. Examples of acoustic transducers that may be utilized in the present invention and which can be commercially purchased for frequencies ranging from Hertz to Gigahertz include Matec broadband immersion transducers MIA series (10–196 MHz), Matec broadband MIBO series (5–10 MHz), Matec broadband MICO (3.5 MHz), Matec broadband MIDO (2.25 MHz), Matec broadband MwO series (50 KHZ–1 MHz), Matec GPUT series (500 KHz–20 MHz), Matec intravascular blood flow VP-A50 series (5–30 MHz), the Teledyne Electronic Technologies In-phase or Out-of-phase broadband MHz/GHz (up to 17.5 GHz) array transducer of zinc oxide on sapphire and optional anti-reflective coating, and Channel Industries Kilohertz transducers. In the ultrahigh acoustic frequencies (upper GHz and THz) maser and laser systems may be utilized.

The transducers can produce an acoustic wave within a range of frequencies (broadband) or for one specific frequency (narrowband).

Commercially available acoustic amplifiers include but are not limited to Matec gated amplifier systems (100 KHZ-200 MHz), and EM broadband amplifier model 607L (0.8–1,000 MHz.)

Complete acoustic systems including power frame, computer interface, pulse width generator, gated amplifier, broadband receiver, and phase detector (100 KHZ-100 MHz) can be purchased commercially from sources such as Matec.

The acoustic delivery system is variable depending on the application. Acoustic energy waves can be transmitted into gaseous, liquid, or solid media either by direct contact of the transducer with the target structure medium, or by coupling of transmission of the acoustic wave through other structures or mediums one of which is in direct contact with the target structure. In the case of biologic structures, coupling through multiple structures or media is a likely occurrence, as the acoustic wave travels through multiple layers of biologic tissue to reach its target structure. If the target structure is a liquid, a transducer can be placed into the liquid in direct contact with it, or the liquid can be placed in a container whose walls are themselves transducers, in direct contact with the liquid. Also, a transducer can be placed on the outside of the walls of a container in which the liquid is placed.

If the target structure is a solid, a transducer can again be placed in direct contact with it. The solid can be placed in a gas or liquid which is used as a coupling agent. A liquid or gel-type coupling agent can also couple between a free-standing solid and a transducer, when the transducer is placed on a surface of the solid.

Figure 2:
FIG. 2 is a block schematic of a basic Acoustic Energy Detection System.
Figure 3:
FIG. 3 is a block schematic of a stationary magnetic field applied to a biologic structure.
Figure 4:
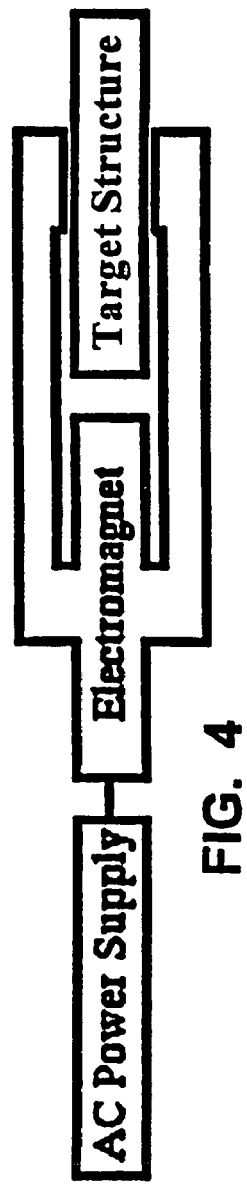
FIG. 4 is a block schematic of an oscillating magnetic field applied to a biologic structure.
Figure 5:
FIG. 5 is a block schematic of a direct or alternating current applied to a biologic structure.
Figure 6:
FIG. 6 is a block schematic of a static charge applied to a biologic structure.

The present invention also comprises receiving and analyzing acoustic energy derived from an inorganic or biologic structure as shown in FIG. 2. Using methods known to those skilled in the art, any device capable of receiving and analyzing acoustic energy through any medium can be used to detect the resonant acoustic and/or acousto-EM frequencies utilized by the invention.

Detection of acoustic energy waves is basically the reverse process of producing acoustic energy waves. Acoustic energy waves striking a transducer apply a mechanical stress, producing electric polarization proportional to the mechanical stress via the piezoelectric effect. The resultant EM energy is converted electronically via oscilloscope type devices to a readable format.

EM energy←piezoelectric transducer←acoustic energy waves.

Thus, piezoelectric transducers may be used to both produce and detect acoustic energy, using the reversible piezoelectric effect.

The structure after being induced into an acoustic resonance state will emit vibrational waves that will cause mechanical stress in the transducer. In turn, an alternating potential difference having the same frequency as the acoustic wave appears as voltage across electrodes connected to a transducer. This voltage is converted via oscilloscope type devices to a readable format.

Oscilloscopes that may be utilized in the present invention include but are not limited to those such as the BK Precision 21 60A (0–60 MHz), the Tektrorix TDS 784A (0–1 GHz), the Tektronix TDS 820 (6–8 GHz), the Tektronix 1180 a B (0–50 GHz); and spectrum analyzers such as Hewlett-Packard 8577A (100 Hz–40 GHz), HP 8555A (10 MHz–40 GHz), Tektronix 492 (50 KHZ–21 GHz), Anritsu MS62C (50 Hz–1.7 GHz), and Polarad 640B (3 MHz-40 GHz) which are all commercially available.

Complete acoustic detection and analysis systems (50 KHz–100 MHz) including power frame, computer interface, pulse width generator, gated amplifier, broadband receiver, phase detector, control software, pre-amplifiers, diode expander, diplexer, filter, and attenuators can be purchased commercially from Matec Instruments Inc., or from other sources.

The acoustic energy under examination can be either reflected or transmitted. For example, in traditional medical ultrasound methods, an acoustic wave is produced from a single transducer. The acoustic wave strikes various structures. Some of the acoustic wave is reflected back from the structures and is detected as reflected waves by the same single transducer. Some of the acoustic wave may also be transmitted through the structures. Many industrial applications of acoustic energy utilize the transmitted, rather than reflected waves.

The present invention also comprises delivering EM energy at resonant acoustic and/or resonant acousto-EM frequencies to a targeted structure as shown in FIGS. 3–7.

Figure 7:
FIG. 7 is a block schematic of delivery of electromagnetic radiation to a biologic structure.
Figure 8:
FIG. 8 is a block schematic of detection of a stationary or oscillating magnetic field in a biologic structure.
Figure 9:
FIG. 9 is a block schematic of detection of a static charge in a biologic structure.
Figure 13:
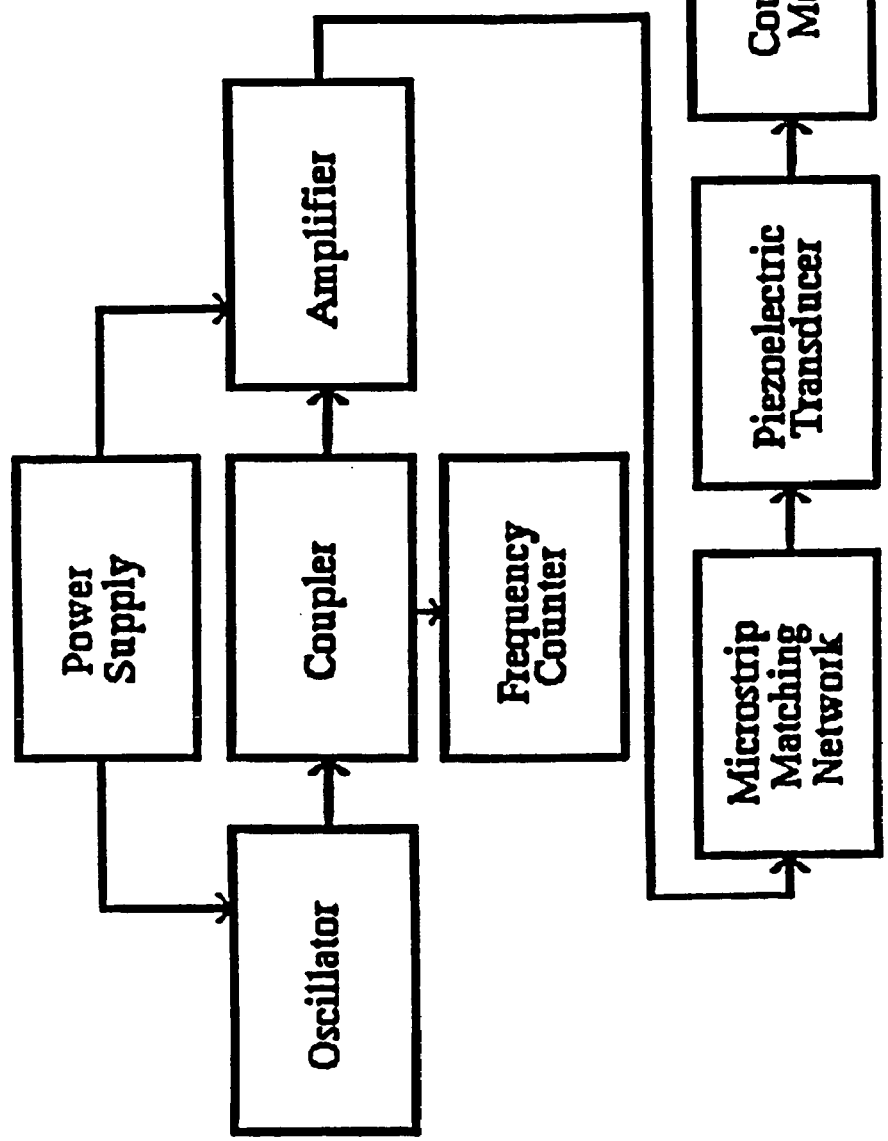
FIG. 13 is a block schematic showing a method for assessing the effects of resonant acoustic fields on viruses.

If a resonant system is embedded in a fluid environment (as is the case with most biologic structures) the dissipation of energy occurs through an intrinsic source in the system. (i.e. via conversion to EM energy), or through loss to the nearby medium (via coupling and transmission of acoustic energy). Using methods known to those skilled in the art, any device capable of generating and transmitting EM energy through any medium can be used to generate the resonant acoustic and/or acousto-EM energy utilized by the present invention including, but not limited to, stationary and oscillating magnetic field (FIGS. 3 and 4), direct or alternating current (FIG. 5), static charge (FIG. 6), electric field, and EM radiation (FIG. 7).

Electrodes for delivering direct and alternating current are available commercially from a wide variety of sources.

Magnetic field generators are commercially available and include Radio Shack Rare-earth magnets 64-1895, GMW Model 5403AC and the like. Oscillators and signal generators as listed above in FIGS. 1 and 2 are commercially available. Likewise, numerous EM radiation delivery systems are commercially available including Waveline Model 99 series Standard Gain Horns (1.7–40 GHz), and JEMA JA-1 50-MS.

Systems known to those skilled in the art for exposing biologic structures to EM energy include anechoic chambers, transverse electromagnetic cells (TEM), resonant cavities, near-field synthesizer, waveguide cell culture exposure system, and coaxial transmission line exposure cells.

The present invention also comprises receiving and analyzing EM energy derived from a targeted structure as shown in FIGS. 8–11. Using methods known to those skilled in the art, any device capable of sensing and analyzing EM energy through any medium can be used to detect the resonant acoustic and/or acousto-EM frequencies utilized by the invention. Direct and alternating current can be assessed by measuring voltage changes (FIG. 11) with 15 voltmeters such as the BK Precision 283 1A (0–1200V, 0.1 mV resolution, or the BK Precision 3910-1 OOOV, 10 uV resolution), detection of static charge (FIG. 9) and by measuring stationary and oscillating magnetic field changes (FIG. 8) with a system such as HET Micro Switch 5594A1F transducer by Honeywell, and instrumentation amplifier chip AD524 by Analog Devices. Monitoring electrodes which are EM field compatible and nonperturbing are made of carbon loaded Teflon by Technical 20 Fluorocarbons Engineering and by Polymer Corp.

Broadband survey meters are commercially available such as Aeritalia RV and 307 series (1–1,000 MHZ), General Microwave Raham 12 (10 MHZ–18 GHz), Holaday Industries 3000 series (5–300 MHz and 500 MHz–6 GHz), Narda Microwave 8608 (10 MHz-26 GHz), and Instruments for Industry RHM-1(10 KHz–220 MHZ) and the like.

Electric field strength meters are commercially available through sources including but not limited to Rohde & Schwarz MSU (25–1000 MHz), Rohde & Schwarz MSU (0.1–30 MHz), Scientific Atlanta 1640APZ (20 MHz-32 GHz), Electro-Metrics EMS-25 (20 KHz–1 GHz), Anritsu M, NM series (500 KHz–1 GHz) and the like.

Magnetic fields may be assessed using the Bartington Fluxgate Nanoteslameter, Mag-01 and the like.

Spectrum analyzers are commercially available through sources including but not limited to HP 8566A (100 Hz–40 GHz), HP 8555A (10 MHz–40 GHz), Tektronix 492 (50 kHz–21 GHz), Anritsu M562C (50 Hz–1.7 GHz), and Polarad 640B (3 MHz–40 GHz) and the like.

Thermocouple E-field probes are manufactured by Narda, and tissue implantable E-field probes include, for example, the Narda 26088, the EIT 979, and the Holaday IME-O1. Field probes can be connected with the external circuitry by optical-fiber telemetry. This limits perturbation of the test field and eliminates RF interference, thus improving signal to noise detection. Optical fiber kits with transmitter and receiver are commercially available from Hewlett-Packard and Burr-Brown.

EM transmitters, include but are not limited to the JEMA, model JA-150-MS (139–174 MHz) and the like.

While the invention is described in relation to certain specific embodiments and certain system components, it will be understood that many variations are possible, and alternative equipment and/or arrangement of components can be used without departing from the invention. In some cases such variations and substitutions may require some experimentation, but will only involve routine testing.

The following examples and descriptions of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments and system components.

Example 1

Disruption. Augmentation, Detection and/or Identification of Viruses

Since the induction of resonance in a structure can lead to sudden and irreversible structural failure due to rupture of one or more components of that structure, biologic structures can be selectively disrupted using resonant acoustic energy. The present invention takes advantage of the rigid, crystalline structure of viruses for the purposes of detection, augmentation, identification and/or physical disruption of the virion structure using acoustic energy and/or acousto-EM at the resonant frequencies un Viruses may be considered piezoelectric crystals, and therefore, can act as living transducers.

Human illnesses caused by viruses include hepatitis, influenza, chicken pox, mumps, measles, small pox, acquired immune deficiency syndrome (A/DS), ebola, polio, hemorrhagic fever, herpes, and hairy cell leukemia.

Diseases in animals caused by viruses include but are not limited to parvo infection in dogs, feline leukemia, cowpox, rabies, and avian plague.

One of the most notable examples of viral diseases in plant life is the historical potato famine in Ireland, caused by a virus which infects potato plants.

There are two major types of virus symmetry—icosahedral and helical. The icosahedral shape is roughly equivalent to a soccer ball, while the helical shape looks like a toy slinky. The majority of viruses fall into one of these groups, the remainder being complex or unknown. The icosahedral is roughly a spherical shape made up of 20 identical, equilateral triangles, with 3 axes of five-fold symmetry. In the helix, the units of the capsid spiral out around the nucleic acid, which runs down the center of the virus, and there is only one axis of spiraling symmetry.

Within each symmetry group, viruses can further be separated into DNA and RNA groups. Viruses have a central core of nucleic material, either DNA or RNA. This nucleic core is surrounded by a symmetrical protein shell, called a capsid or protein coat. The capsid is composed of individual capsomere morphological units, which are in turn composed of individual structural units. The structural units are also called crystallographic units, because they form a repeating pattern and can be demonstrated with X-ray crystallographic diffraction techniques. Structural units are the building blocks of the virus structure and are usually identical proteins.

In some viruses, a lipoprotein membrane, or envelope, surrounds the capsid. The envelope is derived from host cell membranes and is modified by the virus during its departure from the host cell. The envelope may carry specific virus proteins such as hemagglutinin or neuramimidase that are important for future functions and survival of the virus. The envelope of some viruses is studded with projections, or peplomers, which look like a fringe around the edge. The fringe may also be important for function and survival of the virus.

Classically, the piezoelectric phenomenon is said to exist when the application of a mechanical stress to certain dielectric (electrically nonconducting) crystals produces electric polarization (electric dipole moment per cubic meter) which is proportional to the mechanical stress. Conversely, application of an EM field to a crystal produces mechanical stress and distortion, and hence acoustic energy.

A necessary condition for the piezoelectric phenomenon in a crystal is the absence of a center of symmetry. Twenty of the 32 classically defined crystal classes lack a center of symmetry and are piezoelectric. Viruses are crystalline structures and as such are susceptible to vibrational effects by the use of resonant acoustic and/or acousto-EM energy. Icosahedral viruses have 5-fold symmetry and thus do not have a classical center of symmetry in their crystalline structure, the necessary condition for a piezoelectric substance. Helical viruses likewise do not have a classical center of symmetry, as the spiraling capsids are offset from the 90 degree horizontal of the center axis. In addition to the crystalline structure of viruses being susceptible to the vibrational resonant effects of acoustic energy, viruses, as used in the present invention, may also function as piezoelectric, acoustic resonance structures.

The classical 32 groups of naturally occurring crystals defined in non-organic chemistry, do not include a group with 5-fold or offset helical symmetry. It is postulated by the inventors that viruses may represent a 33rd and 34th group of naturally occurring crystals.

The present invention has the potential to significantly reduce the number and severity of viral infections suffered by the world population. The invention has the potential to augment production of vaccines, or viral gene transfer. Also, the present has veterinary applications, i.e. treating viral infections in livestock and poultry, as well as agricultural applications. Unlike prior art treatments that use non-resonant frequencies in the ultrasound range, the present invention uses specific frequencies that create resonance in specific viruses, but not in the adjacent tissues. The methods of the present invention also use electromagnetic energy equivalent to the acousto-EM signatures produced by viruses in a state of acoustic resonance, and utilize the piezoelectric, intrinsic energy dissipation, acoustoelectric, and/or magnetoacoustic properties of viruses, either alone, in combination with each other or in combination with a resonant acoustic field.

The disruption of viruses is useful to treat multicellular organisms, in particular, animals, including mammals, birds, plants, fruit, insects, arthropods, and the like or portions thereof which are susceptible to infection by viruses. Portions of a multicellular organism which may be treated for disruption of viruses include but are not limited to whole body, limbs, organs such as the kidney, spleen, liver, pancreas, heart, lung, gastrointestinal tract, and the like, tissue such as the cornea, bone, bone marrow, blood, cartilage and the like. Products derived from the multicellular organism such as blood products are included within the scope of the invention.

In one embodiment of the present invention used in disruption of a virus, the body or the portion of the body to be treated may be immersed in a conductive medium and acoustic waves applied through the medium to the body or portion thereof at a resonant frequency to cause resonance and disruption of the virus infecting the body or portion thereof. The duration of the treatment is sufficient to disrupt at least about 25% of the virus present, preferably at least about 50%. In one embodiment the duration of treatment is sufficient to disrupt at least about 50% to about 100% of the virus and at the same time have little or no harmful side effects to the host multicellular organism. The power intensity is dependent upon the tissue or organism and may range from $1\times10^{-11}$ W/m$^2$ to $1\times10^{11}$ W/m$^2$ and preferably from about 100 to about 10,000 W/m$^2$.

In the case where the multicellular organism is infected with more than one genus or species of virus, it is desirable to treat the organism with a resonant frequency specific to disrupt each type of virus infecting the organism. As in the case of a human infected with HIV-1, opportunistic infections may occur caused by such viruses as cytomegalovirus, adenovirus, Herpes Simplex virus, and the like. In such a case, the unique resonant frequency may be applied for each organism infecting the human.

The present method is beneficial in organ or tissue transplantation. Treatment of organs or tissues from a donor prior to transplantation prevents or inhibits the transmission of disease-causing viruses to the recipient. Such a method is useful in xenotransplants, allogeneic transplants, syngeneic transplants and the like. Donor organ or tissue to be treated for disruption of virus include but are not limited to cornea, heart, liver, lung, skin, bone, bone marrow cells, blood and blood products, kidney, pancreas, and the like.

Examples of diseases caused by retroviruses which may be inhibited or treated using the disruption methods described herein include but are not limited to AIDS, leukemia, mouse mammary tumor, sarcoma and the like.

Examples of diseases caused by Hepadna viruses include but are not limited to Hepatitis B, Hepatitis C, liver cancer, woodchuck hepatitis, ground squirrel hepatitis, duck hepatitis and the like.

Examples of diseases caused by Herpes viruses which may be prevented, inhibited or treated using the methods described herein include but are not limited to genital and oral herpes, chickenpox, shingles, cytomegalovirus disease (birth defects and pneumonia), mononucleosis, Burkitt's lymphoma, nasopharyngeal cancer, bovine mammillitis, pseudorabies, and the like.

Examples of diseases caused by Pox viruses which may be prevented, inhibited or treated using the methods described herein include but are not limited to smallpox, cowpox, pseudocowpox, molluscum contagiosum, contagious pustular dermatitis, buffalopox, camelpox, monkeypox, rabbitpox, mousepox, bovine papular otomatitis, fowlpox, turkeypox, sheeppox, goatpox, harepox, squirrelpox, swinepox and the like.

Examples of diseases caused by Papova viruses which may be prevented, inhibited or treated using the method of disrupting viruses include but are not limited to human wart virus, genital warts, cervical cancer, progressive multifocal leukoencephalopathy, warts and tumors in mice, monkeys and rabbits.

Examples of diseases caused by Adenovirus which may be prevented, inhibited or treated using the method of disrupting viruses include but are not limited to upper respiratory tract infections, gastroenteritis, conjunctivitis and tumors.

Examples of diseases caused by Parvo viruses amenable to prevention, inhibition or treatment using the methods described herein include but are not limited to Fifth disease, bone marrow failure, Rheumatoid arthritis, fetal death and low birth weight, feline leukemia and the like.

Examples of Picorna virus related diseases which may be prevented or treated using the methods described herein include but are not limited to polio, Hepatitis A, common cold, foot and mouth disease, encephalitis, myocarditis, enteritis, swine vesicular disease, contagious vesicular disease and the like.

Examples of diseases caused by Reo viruses amenable to prevention, inhibition or treatment using resonant acoustic energy include, but are not limited to, upper respiratory tract infections, Colorado tick fever, gastroenteritis and the like.

Examples of Orthomyxo virus related diseases which may be prevented, inhibited or treated using the methods described herein include but are not limited to influenza of man, pigs, horses, seals, birds and the like.

Other examples of diseases caused by viruses which may be prevented, inhibited or treated using resonant acoustic energy of the present invention include but are not limited to viral diarrhea, infantile gastroenteritis, vesicular exanthema of swine, sea lion disease encephalomyelitis, Dengue fever, yellow fever, rubella, equine encephalomyelitis, hog cholera, Bwamba fever, Oriboca fever, Rift Valley fever, Congo hemorrhagic fever, Nairobi sheep disease, African swine fever and the like.

The present method of disrupting a virus may also be utilized in agricultural settings. For example, plants, fruits, vegetables, and the like, suspected of containing disease causing viruses may be treated using resonant acoustic and/or acousto-EM energy for disruption of the viruses. Portions of plants which may be treated for disruption of a virus include but are not limited to seeds, seedling, pulp, leaves, vegetables, fruits, and the like.

The methods of the present invention comprise delivering acoustic energy at resonant frequencies to viruses. For example, the qualitative and quantitative resonant frequencies can be determined in vitro as shown by the apparatus in FIG. 12. A drop of fluid (whole blood, serum, culture fluid, or host cells, etc.) with known resonant acoustic characteristics, and which also contains a known virus as determined by standard virology methods, is placed on a thin disc of absorptive media with known resonant acoustic characteristics (paper, cellulose, cotton, polymer, etc.). A thin slice of viral-laden tissue or material (embedded or sliced material such as provided commercially by Polysciences, Inc. JB4 Embedding, Paraffin, Immuno-Bed Kit, LR Gold, Osteo-Bed Bone Kit, Polyfreeze, PEG 4000 Resin, PolyFin Paraffin, etc.) can be used. The virus disc is placed between two broadband low GHz or high MHz transducers such as disclosed above and clamped into place.

The target range of frequencies to be examined for qualitative viral resonance signatures are derived using the speed of sound in biologic tissues 1,500 m/s divided by desired wavelength, based on viral dimensions. If the viral dimensions are unknown, they may be determined by electron microscopy using techniques known in the art.

One transducer generates the acoustic signal and may sweep through a wide band of target frequencies, and the other transducer detects the transmitted acoustic signal. The acoustic signal transmitted from the virus test disc/slice is fed into the positive lead of a signal analyzer. The known acoustic signals from the test fluid and disc, or test embedding material serve as a control and are fed into the negative lead of the signal analyzer. The control signatures are canceled out and the remaining resonant acoustic signature displayed is from the virus in the sample, yielding a qualitative result.

By varying the range of frequencies analyzed and comparing the amplitudes at each frequency, one can identify the primary resonant frequencies, and the associated harmonic resonant frequencies. The primary resonant frequencies will have the highest amplitude. Each virus will have multiple primary frequencies depending on viral dimensions including, but limited to, the diameter, length (if cylindrical or helical), apical distance, and unit distance. See Table 2 for calculated ranges of primary resonant frequencies for individual viruses, using acoustic velocity as 1,500 m/s, and viral dimensions as currently determined by standard virology methods. Results may vary in practice depending on specific viral factors such as bulk modulus, dispersion, acoustic velocity in viral materials, in vivo vs. in vitro dimensions, etc. and thus the frequencies are in no way limited to the calculated frequencies in Table 2.

TABLE 2

I. ICOSAHEDRAL SYMMETRY

A. DNA Viruses

| VIRUS (# capsomeres) | DIAMETERS (nm) | APICAL LENGTH 58% ave d (nm) | UNIT DISTANCE (nm) | FREQUENCY (Hz) |
|---|---|---|---|---|
| Parvovirus | 21 | | | $7.143 \times 10^{10}$ |
| (32) | 23 | | | $6.522 \times 10^{10}$ |
| (Adeno-Assoc. Virus) | 22 | | | $6.818 \times 10^{10}$ |
| | | 12.76 | | $1.176 \times 10^{10}$ |
| | | | 6.63 | $2.26 \times 10^{11}$ |
| Polyomavirus | 40 | | | $3.75 \times 10^{10}$ |
| (JC Virus, BK Virus, | 50 | | | $3.00 \times 10^{10}$ |
| Simian Virus 40, | 45 | | | $3.33 \times 10^{10}$ |
| Bovine, Baboon) | | 26.1 | | $5.75 \times 10^{10}$ |
| (72) | | | 13? skewed | |
| Papillomavirus | 45 | | | $3.33 \times 10^{10}$ |
| (72) | 55 | | | $2.72 \times 10^{10}$ |
| | 50 | | | $3.00 \times 10^{10}$ |
| | 29 | | | $5.17 \times 10^{10}$ |
| | | | ? skewed | |
| Herpesvirus | 95 | | | $1.57 \times 10^{10}$ |
| (162) | 105 | | | $1.42 \times 10^{10}$ |
| (Oral, genital, | 100 | | | $1.50 \times 10^{10}$ |
| chickenpox, zoster, | | 58 | | $2.58 \times 10^{10}$ |
| I, II, III) | | | 25 | $6.00 \times 10^{10}$ |
| | | | 9 | $1.66 \times 10^{10}$ |
| Bovine herpes virus | 95 | | | $1.57 \times 10^{10}$ |
| (162) | 105 | | | $1.42 \times 10^{10}$ |
| | 100 | | | $1.50 \times 10^{10}$ |
| | | 58 | | $2.58 \times 10^{10}$ |
| | | | 25 | $6.00 \times 10^{10}$ |
| | | | 9 | $1.66 \times 10^{11}$ |
| Herpesvirus IV virus | 95 | | | $1.57 \times 10^{10}$ |
| (162) | 105 | | | $1.42 \times 10^{10}$ |
| (Epstein Barr) | 100 | | | $1.50 \times 10^{10}$ |
| | | 58 | | $2.58 \times 10^{11}$ |
| | | | 25 | $6.00 \times 10^{10}$ |
| | | | 9 | $1.66 \times 10^{10}$ |
| Herpesvirus V virus | 95 | | | $1.57 \times 10^{10}$ |
| (162) | 105 | | | $1.42 \times 10^{10}$ |
| (Cytomegalo) | 100 | | | $1.50 \times 10^{10}$ |
| | | 58 | | $2.58 \times 10^{10}$ |
| | | | 25 | $6.00 \times 10^{10}$ |
| | | | 9 | $1.66 \times 10^{11}$ |
| | | 50 nm core | | $3.00 \times 10^{10}$ |
| Adenovirus | 70 | | | $2.14 \times 10^{10}$ |
| (252) | 75 | | | $2.00 \times 10^{10}$ |
| | 72.5 | | | $2.07 \times 10^{10}$ |
| | | 42.05 | | $3.57 \times 10^{10}$ |
| | | | 8.41 | $1.78 \times 10^{11}$ |
| Vaccinia | 200 | | | $7.5 \times 10^{9}$ |
| | 250 | | | $6.0 \times 10^{9}$ |
| Variola | 200 | | | $7.5 \times 10^{9}$ |
| (Smallpox) | 250 | | | $6.0 \times 10^{9}$ |
| Cowpox Virus | 200 | | | $7.5 \times 10^{9}$ |
| | 250 | | | $6.0 \times 10^{9}$ |
| Molluscum | 200 | | | $7.5 \times 10^{9}$ |
| Contagiosum | 250 | | | $6.0 \times 10^{9}$ |
| ORFVirus | 150 | | | $1.0 \times 10^{10}$ |
| | 250 | | | $6.0 \times 10^{9}$ |
| Paravaccinia | 150 | | | $1.0 \times 10^{10}$ |
| | 250 | | | $6.0 \times 10^{9}$ |
| Hepatitis B | 40 | | | $3.75 \times 10^{10}$ |
| Virus | 45 | (Dane Particle) | | $3.33 \times 10^{10}$ |
| | 42.5 | | | $3.53 \times 10^{10}$ |
| | | 28 nm core (Spheres and bacillary forms noninfective) | | $5.36 \times 10^{10}$ |

B. RNA VIRUSES

| VIRUS (# capsomers) | DIAMETERS (nm) | TRIANGLE LENGTH (nm) | UNIT DISTANCE (nm) | FREQUENCY (Hz) |
|---|---|---|---|---|
| Calicivirus | 31 | | | $4.84 \times 10^{10}$ |
| 32 | 35 | | | $4.28 \times 10^{10}$ |

TABLE 2-continued

| | | | | |
|---|---|---|---|---|
| | 33 | | | $4.54 \times 10^{10}$ |
| | | 19.14 | | $7.84 \times 10^{10}$ |
| | | | 9.96 | $1.51 \times 10^{11}$ |
| Picornavirus | 25 | | | $6.00 \times 10^{10}$ |
| 32 | 30 | | | $5.00 \times 10^{10}$ |
| | 27.5 | | | $5.45 \times 10^{10}$ |
| | | 15.95 | | $9.40 \times 10^{10}$ |
| | | | 8.29 | $1.81 \times 10^{11}$ |
| Reovirus | 70 | | | $2.14 \times 10^{10}$ |
| (92) | 75 | | | $2.00 \times 10^{10}$ |
| | 72.5 | | | $2.07 \times 10^{10}$ |
| | | 42.05 | | $3.57 \times 10^{10}$ |
| | | | 14.02 | $1.07 \times 10^{10}$ |
| HIV | 85 | | | $1.76 \times 10^{10}$ |
| | 150 | | | $1.00 \times 10^{10}$ |
| | 100 | | | $1.76 \times 10^{10}$ |
| | | Surface spikes 12 nm | | $1.25 \times 10^{10}$ |
| | | 18 nm | $8.33 \times 10^{10}$ | |
| | | Cone width 1/4 of diameter | | |

II. HELICAL SYMMETRY

RNA Viruses

| VIRUS (# capsomers) | DIAMETERS (nm) | TRIANGLE LENGTH (nm) | UNIT DISTANCE (nm) | FREQUENCY (Hz) |
|---|---|---|---|---|
| Influenza | 80 | | | $1.88 \times 10^{10}$ |
| Human A, B | 120 | | | $1.25 \times 10^{10}$ |
| & C, Avian | | Peplomers 10 nm (A & B) | | $1.5 \times 10^{10}$ |
| | | Peplomers 8 nm (C) | $1.88 \times 10^{11}$ | |
| | | A - 6 nm wide helix core | $6.66 \times 10^{11}$ | |
| | | C - 9 nm wide helix core | $1.66 \times 10^{11}$ | |
| Parainfluenza | 90 | | | $1.66 \times 10^{10}$ |
| (Mumps, Croup) | 300 | | | $5.00 \times 10^{9}$ |
| | | Helix 15 nm | | $1.00 \times 10^{11}$ |
| | | Helix 19 nm | | $7.89 \times 10^{10}$ |
| | | 7.5 rimby | | $2.00 \times 10^{11}$ |
| | | 3 nm | | $5.00 \times 10^{11}$ |
| | | Central canal 5 nm | $3.00 \times 10^{11}$ | |
| Paramyxovirus | 90 | | | $1.66 \times 10^{10}$ |
| (NewcastleDs. | 300 | | | $5.00 \times 10^{9}$ |
| Avian, Simian, | | Helix 15 nm | | $1.00 \times 10^{11}$ |
| Measles) | | Helix 19 nm | | $7.89 \times 10^{10}$ |
| | | Central canal 5 nm | $3.00 \times 10^{11}$ | |
| Respiratory | 120 | | | $1.25 \times 10^{10}$ |
| Syncytial Virus | | | | |
| | | Helix 15 nm | | $1.00 \times 10^{11}$ |
| | | Helix 19 nm | | $7.89 \times 10^{10}$ |
| | | Central canal 5 nm | | $3.00 \times 10^{11}$ |
| Marburg virus | 80 nm wide helix | | | $1.88 \times 10^{10}$ |
| & Ebola Virus | 50 nm internal canal | | | $3.00 \times 10^{10}$ |
| | 20 nm central canal | | | $7.50 \times 10^{10}$ |

Once the qualitative viral resonant acoustic signature has been determined, quantitative results may be determined by comparing the resonant acoustic signature amplitudes from samples of known concentrations of a specific virus. Samples with higher viral loads (concentrations) will have higher resonant acoustic signature amplitudes. A ratio of primary resonant frequency amplitude to viral concentration is thus derived, allowing for assessment of viral load in samples of unknown concentration.

In another embodiment, resonant acoustic signatures from the test disc/slice may be generated either by first clamping a control disc/slice into the transducer chamber and storing the resonant acoustic signature in a microprocessor for subsequent processing with the test disc/slice signature, or by clamping a control into a second transducer chamber and sweeping through the wide band of frequencies simultaneously with the test disc/slice virus sweep. Also, the test disc/slice may be clamped between the transducer and a reflective surface, and the acoustic wave generated and received by the same transducer, thus analyzing reflected rather than transmitted acoustic waves. Furthermore, one or more transducers analyzing reflected or transmitted acoustic energy may by immersed into a fluid or medium containing the virus.

In another embodiment one or more transducers analyzing reflected or transmitted acoustic energy constitute the walls of a vessel into which a fluid or medium containing virus is placed.

The present invention also allows the effects of the resonant frequencies to be determined in vitro as shown by the apparatus in FIG. 13. Using standard virology culture methods, known to those skilled in the art, the viral culture may be placed in a reusable/autoclavable test cylinder. The bottom surface of the test cylinder is the transducer, constructed for the appropriate frequencies, such as a thin film zinc oxide on a sapphire substrate. The host medium thus placed in the test cylinder spreads over the bottom of the cylinder in a monolayer and in direct contact with the transducer. Acoustic energy of the desired resonant frequency is then delivered through the culture fluid and host medium to the viruses, and the effects on growth and function are assessed using standard virology methods. By varying the acoustic wave characteristics, such as amplitude, mode (continuous vs. pulsed), shape (sinusoidal vs. square), intensity etc., the ideal frequency and waveform required to obtain specific effects can be determined.

For example, in testing the augmenting and/or disrupting effects of resonant acoustic frequencies on HIV, uninfected T-lymphocyte host cells are first assessed in the test cylinder with the resonant acoustic intervention (resonant frequencies in varying waveform patterns for varying periods of time at varying intensities) using the trypan blue dye exclusion test, which excludes anomalous viral results by assessing the effects of the acoustic intervention on the host cells alone. Step 2 involves placing a calculated number of HIV infected T-lymphocytes in the test cylinder. The host cells form a monolayer on the transducer/floor of the test cylinder, where the acoustic intervention is delivered. The results are then assessed using standard in vitro methods such as the Coulter HIV-1 p24 antigen kit, HIV cultures, HIV-1 DNA by PCR, viral load measurement, quantitative measurements, time to positivity, and growth suppression.

Figure 14:
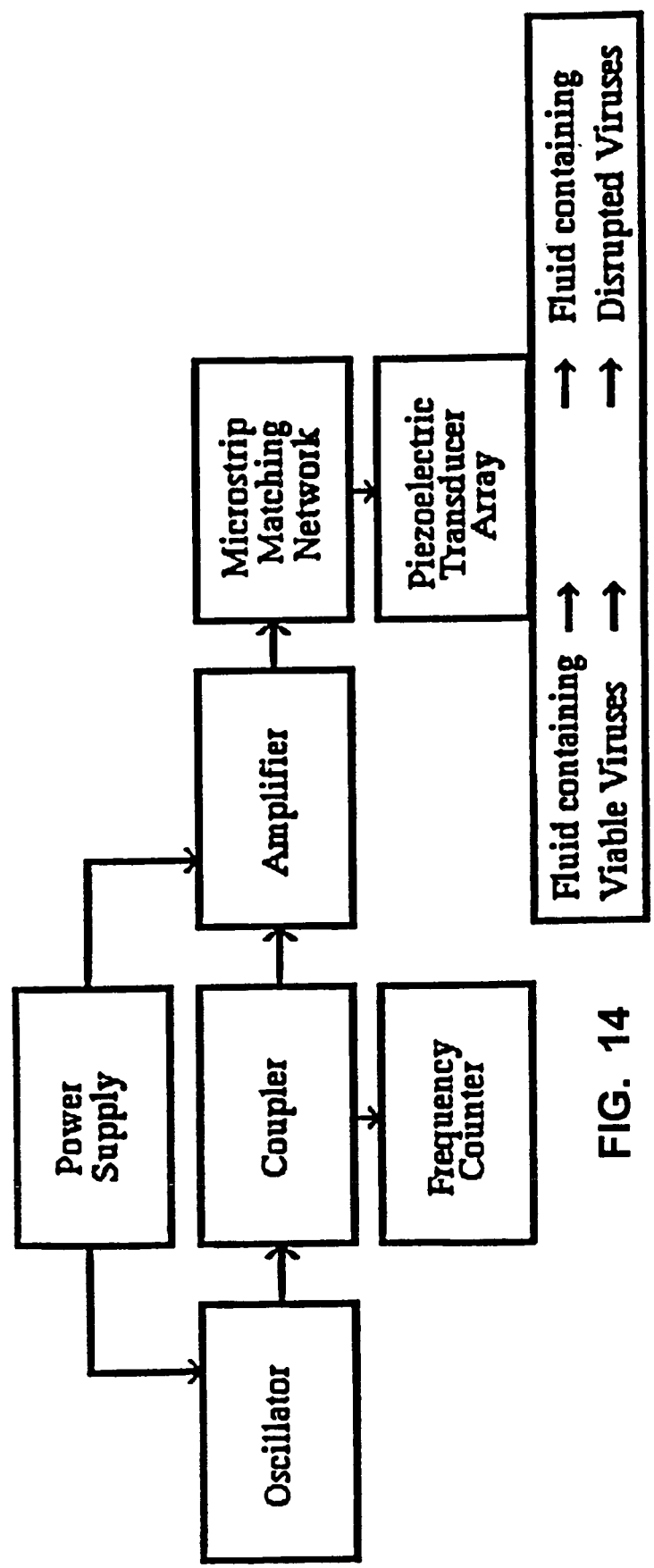
FIG. 14 is a block schematic showing a method for disrupting viruses extra corporeally with resonant acoustic fields.

The methods of the present invention also provide means to disrupt viruses in vivo and extracorporeally in animals as shown in FIG. 14. For example, in humans infected with HIV, an extracorporeal blood circulation system is established using techniques known to those skilled in the art. The extracorporeal blood is passed over a series of reusable/autoclavable sterilized transducers that deliver acoustic energy at primary or harmonic resonant frequencies. The acoustic transducer series acts in effect as an acoustic filter, disrupting viruses in the blood stream. Efficacy of treatment is assessed using viral load studies, as known to one skilled in the art, both prior to and after the extracorporeal treatments.

In another embodiment, the above described acoustic filter is also fitted with a receiving transducer mode for analysis of the blood sample. With initial passes of blood containing large numbers of intact virus, the resonant amplitude will be high. After prolonged exposure of the blood to the disrupting resonant frequencies, the resonant amplitude will decline as the numbers of intact viruses decline, thus giving viral load readings and a method to determine when cessation of the extracorporeal treatment is indicated.

In another embodiment, a sheet of piezoelectric material is fashioned into an envelope or mesh-type transducer, through which the extracorporeal blood is passed. In another embodiment, a tube of piezoelectric material is fashioned into a coil transducer, through which the extracorporeal blood is passed. In another embodiment, the extracorporeal blood is separated into red and white blood cell portions, and only the while blood cell portion is passed through the acoustic filter, thus reducing the time required for treatment and reducing mechanical damage to the red blood cell portion.

In another embodiment, banked blood is passed through an acoustic filter at any one of multiple points in the blood product collection and administration process (i.e., collection from the donor, separation into components, or administration to the recipient).

In another embodiment, nanosystem technology (see *Nanosystems*, by Eric Drechsler; publications of CJ Kim, Berkley University; publications of Ralph Merck, Xerox Co., Palo Alto, Calif.) is employed to make multiple small acoustic oscillators which are enclosed in filter material, the filter material preventing passage of the oscillators but allowing the passage of blood cells and blood components. The nanite virosonic filter is sterilized and attached in line on an extracorporeal system or in a blood products system.

In another embodiment, the resonant and/or harmonic acoustic frequencies are generated using acoustic laser or maser systems. In similar fashion, the whole or fractionated blood is passed extra corporeally over or through a laser or maser acoustic filter.

Figure 15:
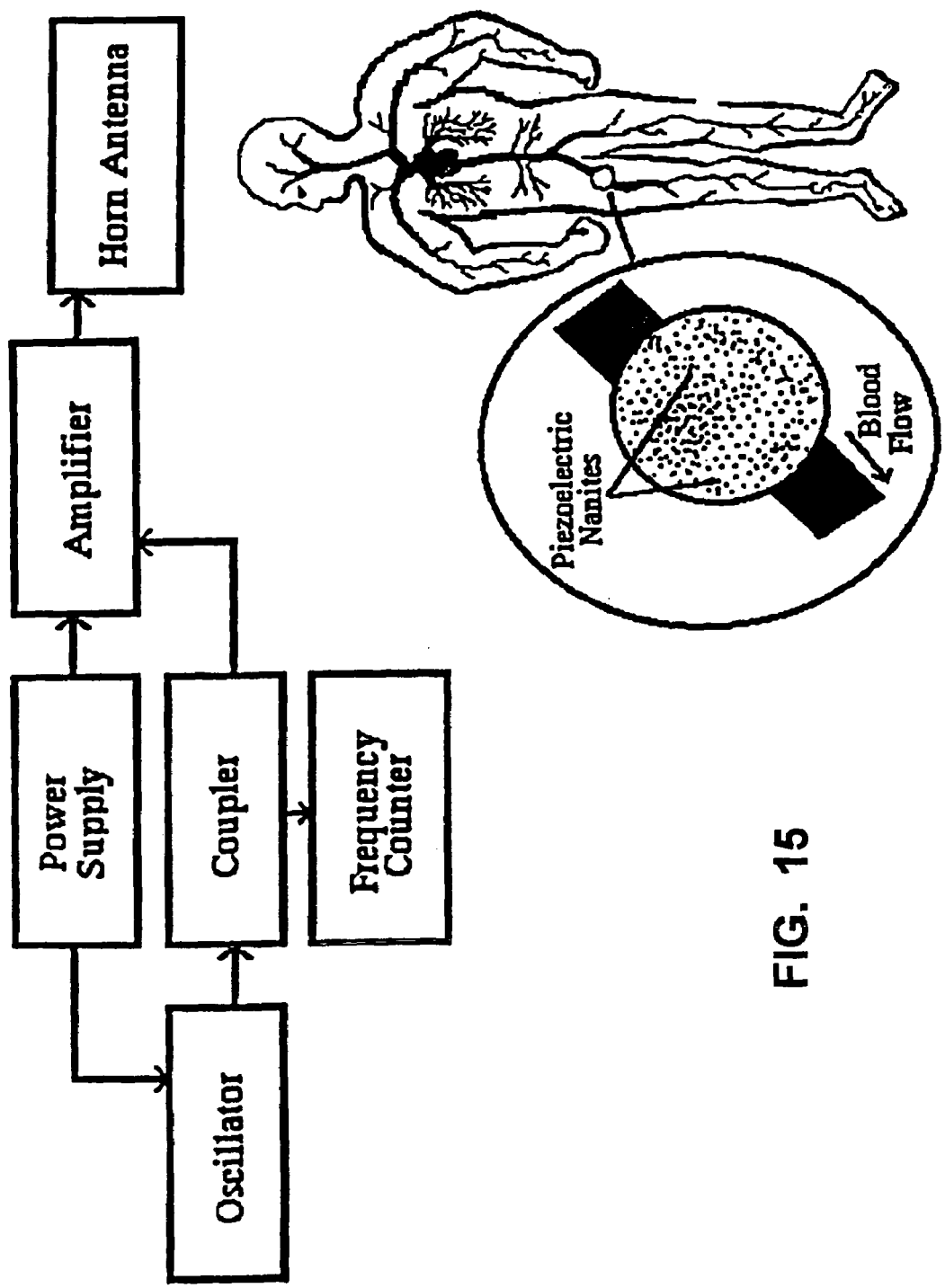
FIG. 15 is a block schematic showing a method for disrupting viruses in vivo intravascularly with resonant acoustic fields.

The method also provides a means to disrupt viruses in vivo and intracorporeally in animals as shown in FIG. 15, using intravascular devices. Nanosystem technology is employed to make multiple small acoustic oscillators which are enclosed in filter material, the filter material preventing passage of the oscillators but allowing the passage of blood cells and blood components. The nanite virosonic filter is attached in line on a CVP type catheter or in a Greenfield-type filter.

In another embodiment, a central venous catheter as known to one skilled in the art (produced commercially by Arrow, Baxter, etc.) is engineered and fitted with a transducer of appropriate frequency at the tip. The catheter is inserted using standard technique into a large vein such as the subclavian, jugular, or femoral vein. Resonant acoustic energy is then delivered to the circulating blood, thereby disrupting virus in vivo.

In another embodiment, the transducer is fitted as an acoustic filter on a larger intravascular device such as a Greenfield filter-type device for the inferior vena cava. The device is fitted with a battery that is rechargeable through the skin, as currently practiced with rechargeable cardiac pacemakers. Once inserted, the acoustic filter reduces viral load in the vena caval blood flow, without the need for the patient to be restricted by catheters.

In another embodiment, inclusion of a receiving acoustic transducer may also detect qualitative and quantitative resonant acoustic frequencies of the virus in the multicellular organism to determine efficacy and duration of treatment.

Figure 16:
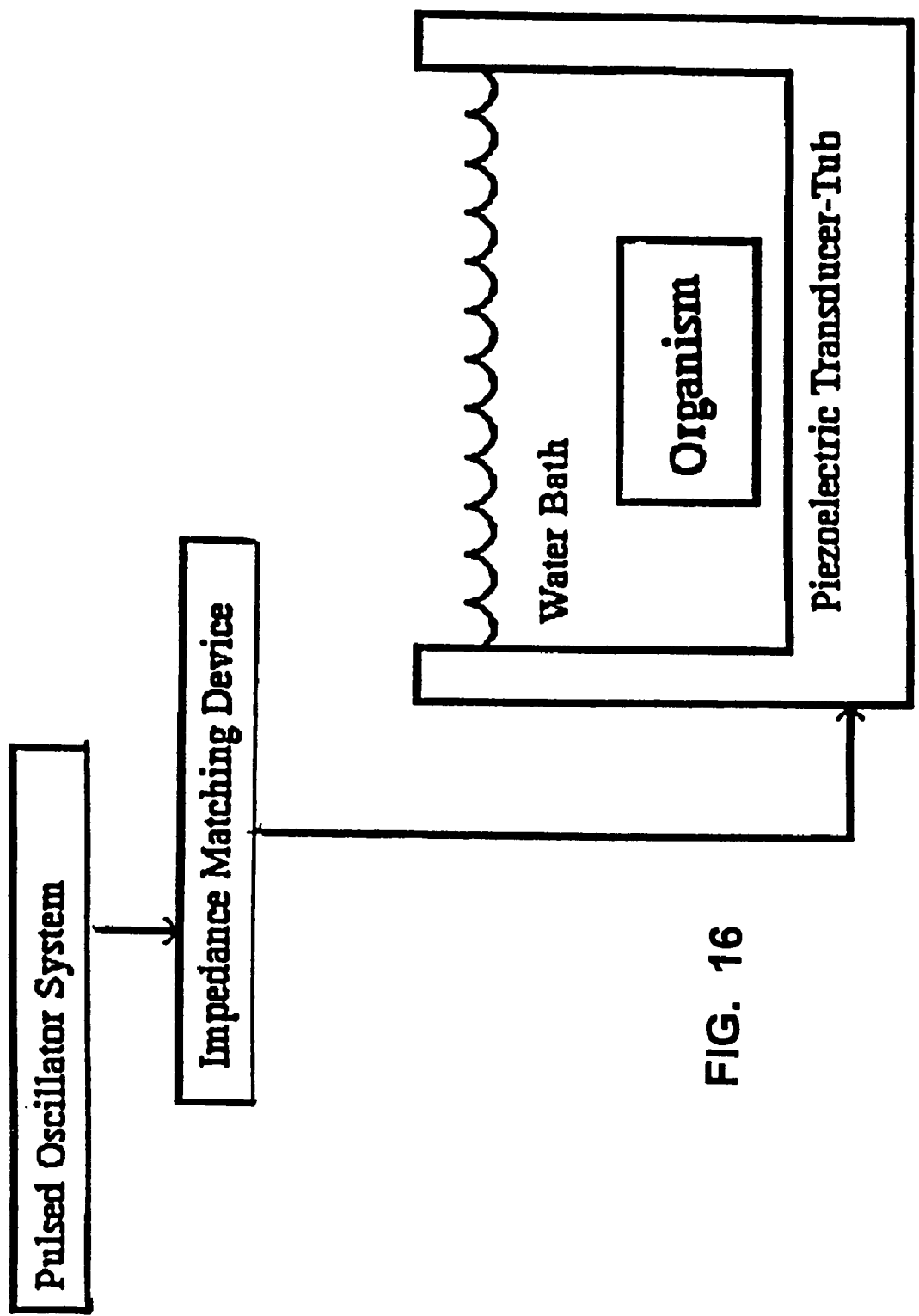
FIG. 16 is a block schematic showing a method for disrupting viruses in vivo in multicellular organism with resonant acoustic fields.

The methods of the present invention also provide a means to augment and/or disrupt viruses in vivo in a multicellular organism, as shown in FIG. 16, using resonant acoustic fields. The organism is placed in a form-fitting tub filled either with water or a coupling medium such as castor oil (reflection coefficient 0.0043) or mineral oil, or such other acoustic conductive gel as is available commercially. Acoustic transducers are either fitted into the walls and floor of the tub, or are themselves the walls and floor of the tub (i.e., piezoelectric polymer sheets or ceramics). A predetermined acoustic field (frequencies, harmonics, amplitude, mode, shape, etc., at a specific intensity) is delivered to the organism from the transducer tub through the coupling medium.

In another embodiment, a receiving acoustic transducer mode also detects qualitative and quantitative resonant acoustic frequencies of the virus in the multicellular organism to determine efficacy of treatment.

Figure 17:
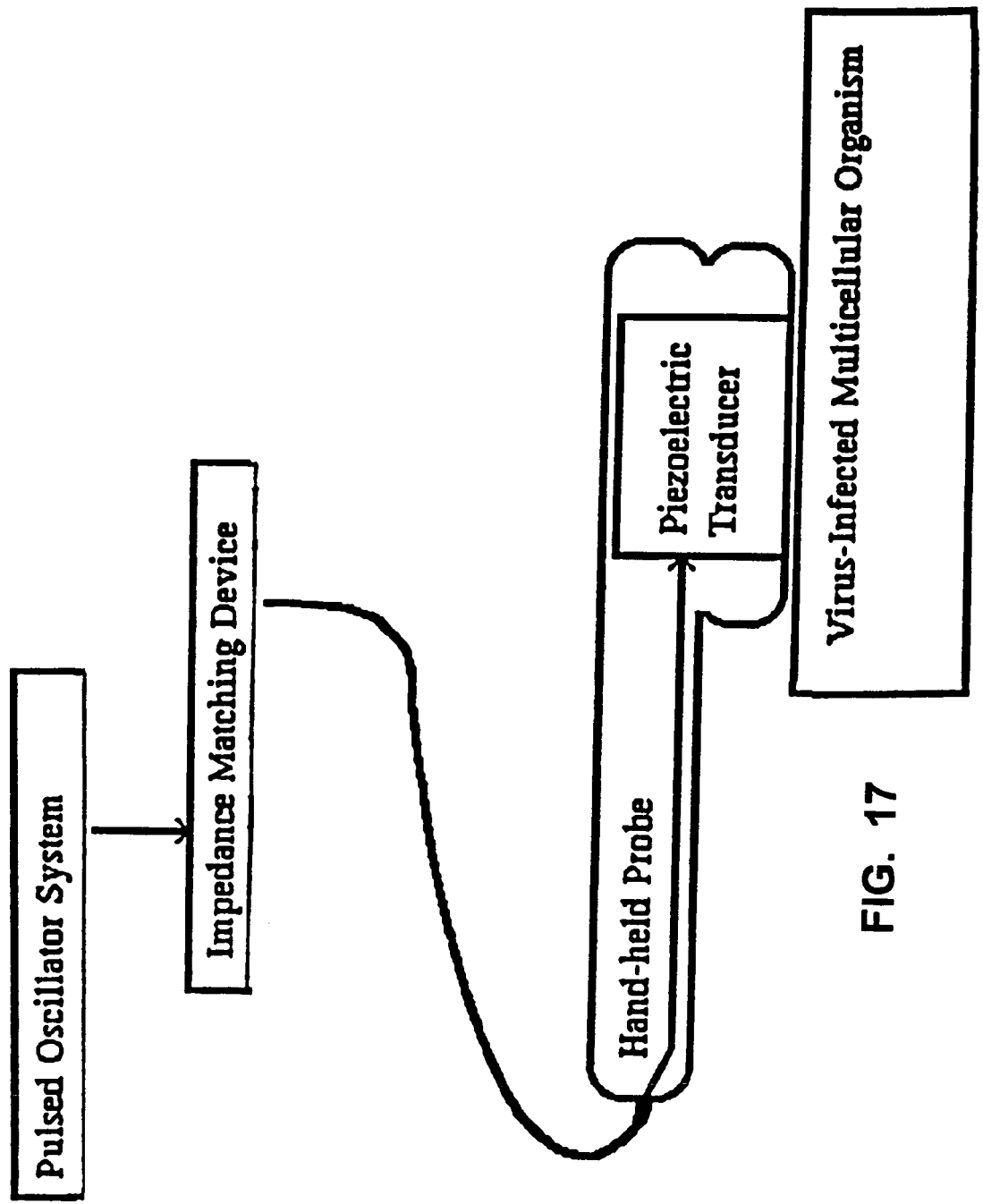
FIG. 17 is a block schematic showing a method for disrupting viruses in a portion of a multicellular organism with a resonant acoustic field probe.

The present invention also provides a method to augment and/or disrupt viruses in vivo in a portion of a multicellular organism as shown in FIG. 17, using a resonant acoustic field probe. Acoustic transducers of desired frequency are fitted into the end of a hand-held probe device, as currently known to those skilled in the art of medical ultrasonography. A predetermined acoustic field (frequencies, harmonics, amplitude, mode, shape, etc. at the required intensity to effect the organism) is delivered to a predetermined portion of the organism, from the hand-held transducer probe. Attenuation in air is eliminated by use of a commercially available acoustic coupling medium such as castor oil. For example, in a person afflicted with hepatitis, the treatment is delivered through the skin over the liver. Subharmonics of the resonant acoustic frequencies can be used to minimize acoustic attenuation at the higher frequencies.

In another embodiment, receiving acoustic transducer mode also detects qualitative and quantitative resonant acoustic frequencies of the virus in the multicellular organism to determine efficacy and duration of treatment.

Figure 18:
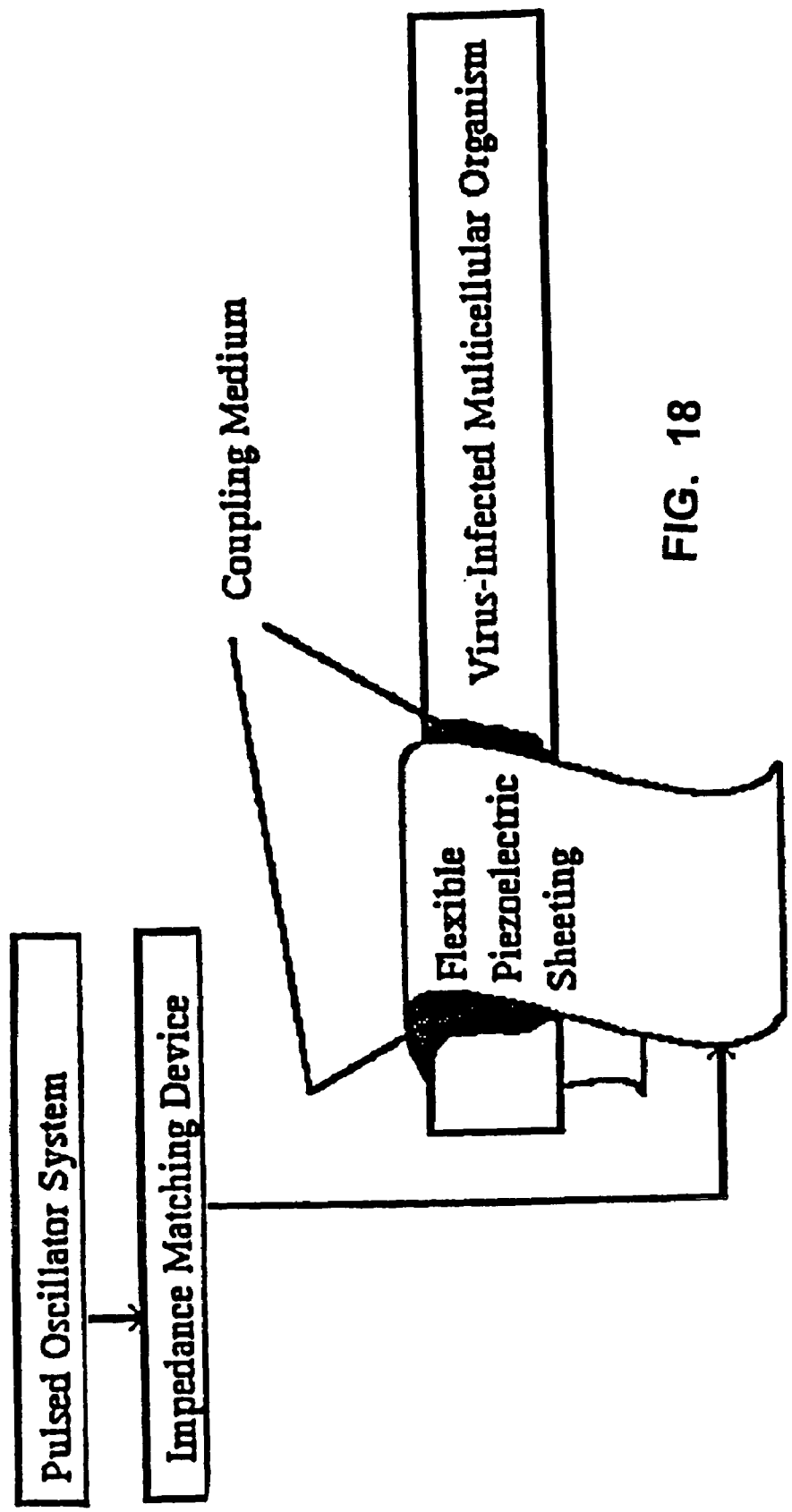
FIG. 18 is a block schematic showing a method for disrupting viruses in a portion of a multicellular organism with a resonant acoustic field sheet.

The present invention also provides a method to disrupt viruses in vivo in a portion of a multicellular organism as shown in FIG. 18, using a resonant acoustic field sheet. Piezoelectric polymer material of desired frequency is fashioned into a flexible transducer sheet device. A predetermined acoustic field (frequencies, harmonics, amplitude, mode, shape, etc.) is delivered to a predetermined portion of the organism, from the transducer sheet device. Attenuation in air is eliminated by use of a commercially available acoustic coupling medium such as castor oil. For example, in a person afflicted with hepatitis, the treatment is delivered by placing the sheet in contact with the skin over the liver. Subharmonics of the resonant acoustic frequencies can be used to minimize acoustic attenuation at the higher frequencies.

In another embodiment, receiving acoustic transducer mode also detects qualitative and quantitative resonant acoustic frequencies of the virus in the multicellular organism to determine efficacy and duration of treatment.

Figure 19A:
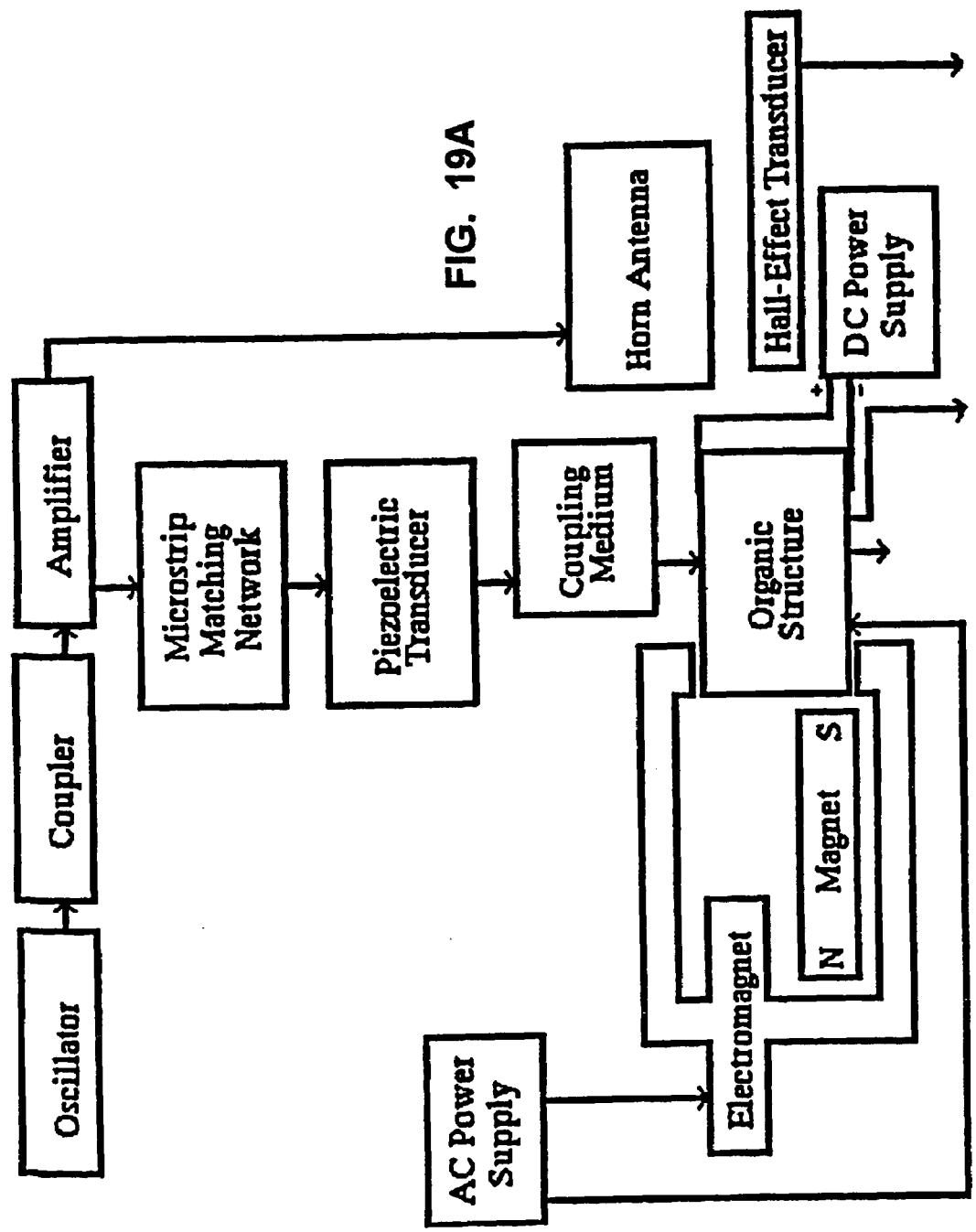
FIGS. 19 A & B are block schematics showing a method for determining resonant acoustic and/or acousto-EM frequencies of viruses.
Figure 19B:
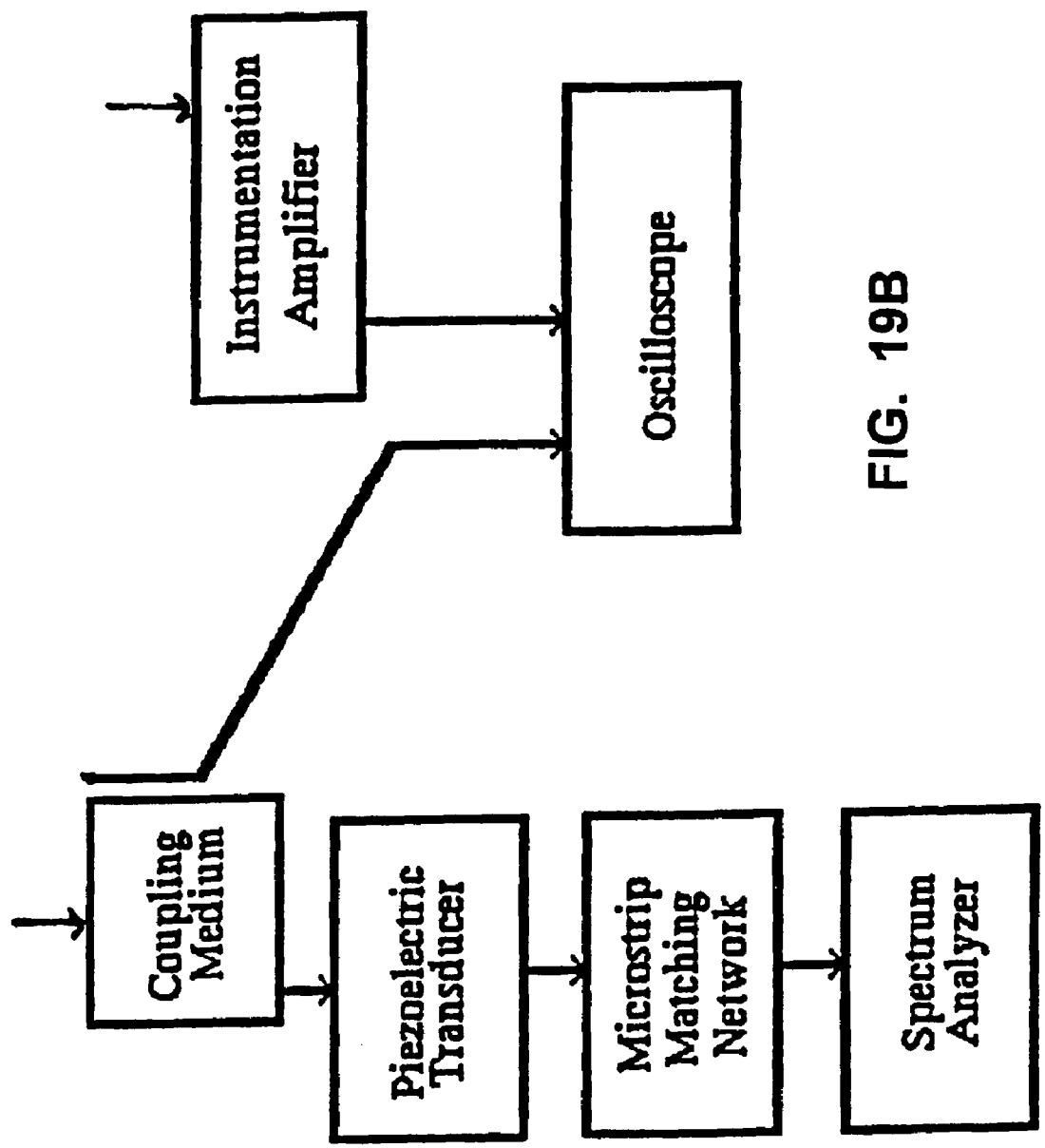

The present invention also provides a means to determine qualitative and quantitative resonant acoustic and/or acousto-EM frequencies in vitro as shown in FIG. 19 A&B. A test device, as described above and shown in FIG. 12, with any and all embodiments, is fitted with transmitters and receivers to transmit, detect, measure, and analyze EM energy. When the resonant acoustic frequencies are applied to the virus test disk, a unique electromagnetic energy pattern is generated, according to the structure and composition of the virus and test disk under study, referred to herein as the resonant acousto-EM signature. Mechanisms producing the resonant acousto-EM signature include, but are not limited to piezoelectricity, acoustoelectricity, magnetoacoustics, and/or intrinsic energy dissipation. The resonant acousto-EM signature represents one or more of several electromagnetic properties and/or fields including, but not limited to, direct current, alternating current, magnetic field, electric field, EM radiation, and/or acoustic cyclotron resonance (standard or Doppler shifted).

All of the above mentioned forms of EM energy are detected, measured, and analyzed with devices and methods known to those skilled in the art. (It should be noted that useful information may also be derived from application of nonresonant frequencies, ie. current characterization of semiconductor biologics via the acoustoelectric effect.) This data in combination with resonant signatures yields even greater sensitivity and specificity to the method. For example, Herpes simplex virus (HSV) I and II will have nearly identical resonant acoustic signatures because they are virtually identical in size and shape. They differ in molecular protein configuration, however, and can be distinguished by their acousto-EM signatures. This includes, but is not limited to, characterization at nonresonant and resonant frequencies of acoustoelectric currents, acousto-EM signatures produced via intrinsic energy dissipation, of acoustic modulation or attenuation in the presence of a magnetic field via the magnetoacoustic effect, and of electric or magnetic fields induced or affected by any of the above processes.

In another embodiment, the test device is also fitted with any and all combinations of resonant acoustic and acousto-EM generating equipment. A sample of unknown composition is exposed to the frequency energy pattern which is included in the acousto-EM signature for a particular structure. Detection of the associated resonant acoustic waves from the sample confirms the presence of the structure in the sample. Further analysis of amplitude would indicate the relative quantity of those particular structures in the sample. For instance, the combined use of resonant acoustic and acousto-EM signatures could be used to search a tissue slice first for the presence of HSV, and then to specify whether it is HSV I, HSV II, or a previously unknown and uncharacterized HSV. In addition, a quantitative assessment of viral load in the sample could also be performed based on relative amplitudes. Thus, the application of resonant acoustic and/or acousto-EM energy fields, in respect to organic or biologic organisms and structures, yields a form of resonant acousto-EM spectroscopy, with three basic stimulation and detection modes (1. acoustic, 2. EM, 3. acoustic and EM), producing nine basic combinations:

1. Acoustic stimulation, acoustic detection;
2. Acoustic stimulation, EM detection;
3. Acoustic stimulation, acoustic and EM detection;
4. EM stimulation, acoustic detection;
5. EM stimulation, EM detection;
6. EM stimulation, acoustic and EM detection;
7. Acoustic and EM stimulation, acoustic detection;
8. Acoustic and EM stimulation, EM detection; and
9. Acoustic and EM stimulation, acoustic and EM detection.

The more sophisticated the stimulation and detection/analysis modes are, the more sensitive and specific the spectroscopy apparatus will be. It should be noted that the use of resonant acousto-EM spectroscopy alone or in combination with resonant acoustic spectroscopy in the present invention is not limited to biological materials and can be utilized to detect and identify inorganic materials or structures as discussed below.

Figure 20:
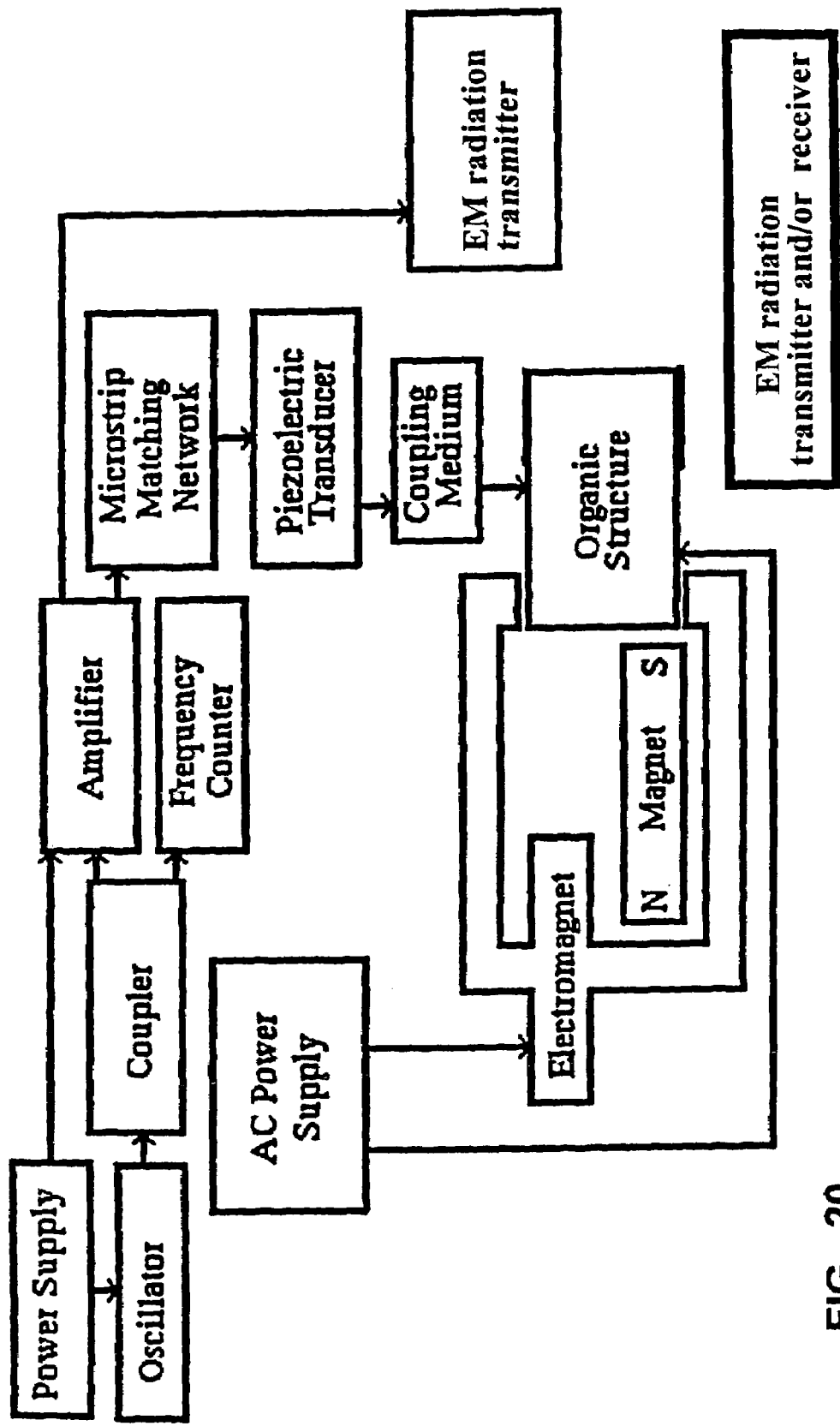
FIG. 20 is a block schematic showing a method for assessing effects of resonant acoustic and/or acousto-EM fields on viruses.

The present invention also provides a method to assess the effects of resonant acoustic and/or acousto-EM energy on viruses using any and all devices which produce acoustic and/or EM energy including, but not limited to, all devices and embodiments previously described. For instance, as shown in FIG. 20, to assess the piezoelectric effects of EM radiation on the crystalline structure of viruses, a test system is used which employs EM radiation of the same frequency as at least one of the resonant acoustic frequencies of the virus. In the case of HIV, the frequency is approximately 15 GHz. A test box made of EM absorptive material is fitted with a 15 GHz EM transmitter, with the EM radiation directed towards the floor of the box. Uninfected T-lymphocyte host cells are first assessed in the test box with the 15 GHz intervention with varying exposure patterns (resonant frequencies in varying waveform patterns for varying periods of time and at varying intensities) using the trypan blue dye exclusion test, which excludes anomalous viral results by assessing the effects of the acousto-EM intervention on the host cells alone. Step 2 involves placing HIV infected T-lymphocytes in the test box, where the acousto-EM intervention is delivered. The results are then assessed using standard in vitro testing of anti-HIV methods such as the Coulter HIV-1 p24 antigen kit, HIV cultures, HIV-1 DNA by PCR, and viral load measurement.

Figure 21:
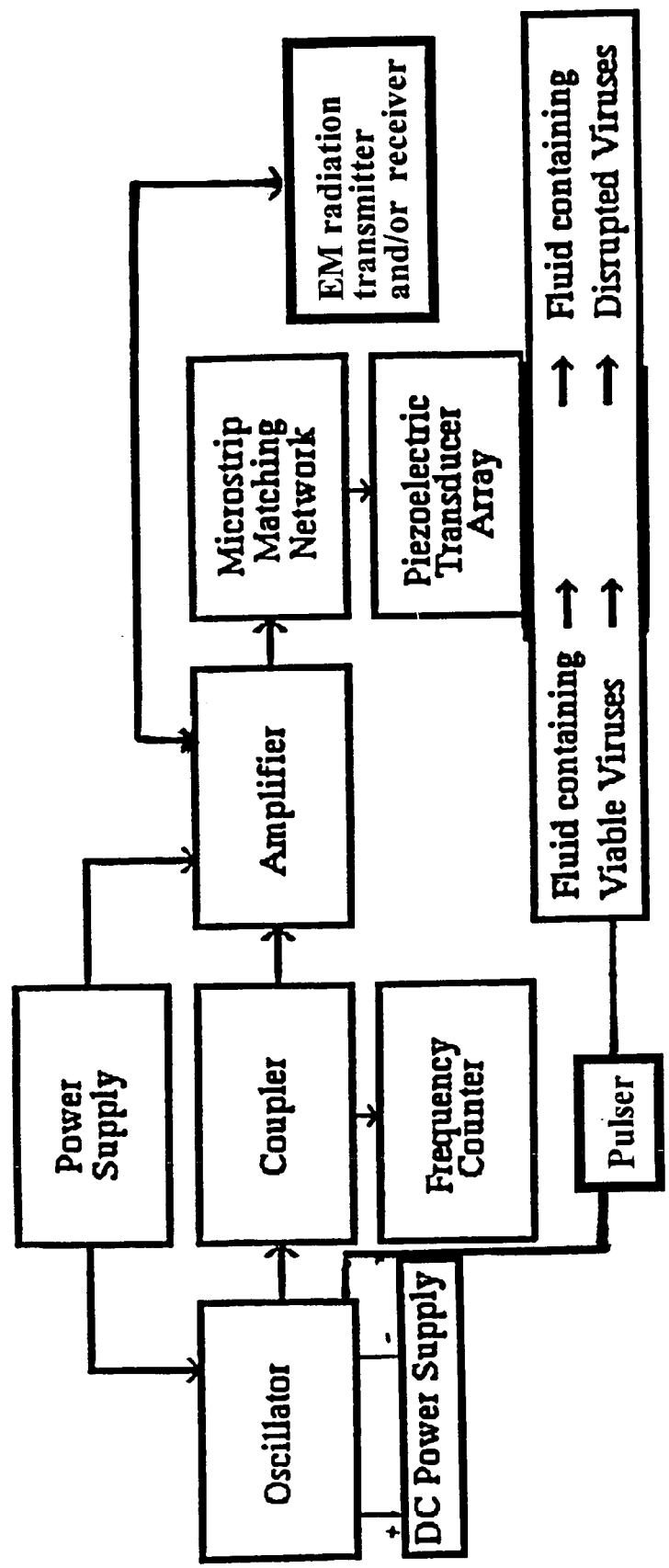
FIG. 21 is a block schematic showing a method for disrupting viruses extracorporeally with resonant acoustic and/or acousto-EM fields.

The present invention also provides a method to disrupt viruses extracorporeally and/or intravascularly in animals using resonant acoustic and/or acousto-EM fields as shown in FIG. 21. For example, in humans infected with HIV, an extracorporeal blood circulation system is established using techniques known to those in the art. The extracorporeal blood is passed over transducers as described in FIG. 14, including any and all embodiments. Acoustic penetration into the blood may be increased using acoustoelectric gain by passing a direct current into the blood parallel with the acoustic waves.

Figure 22:
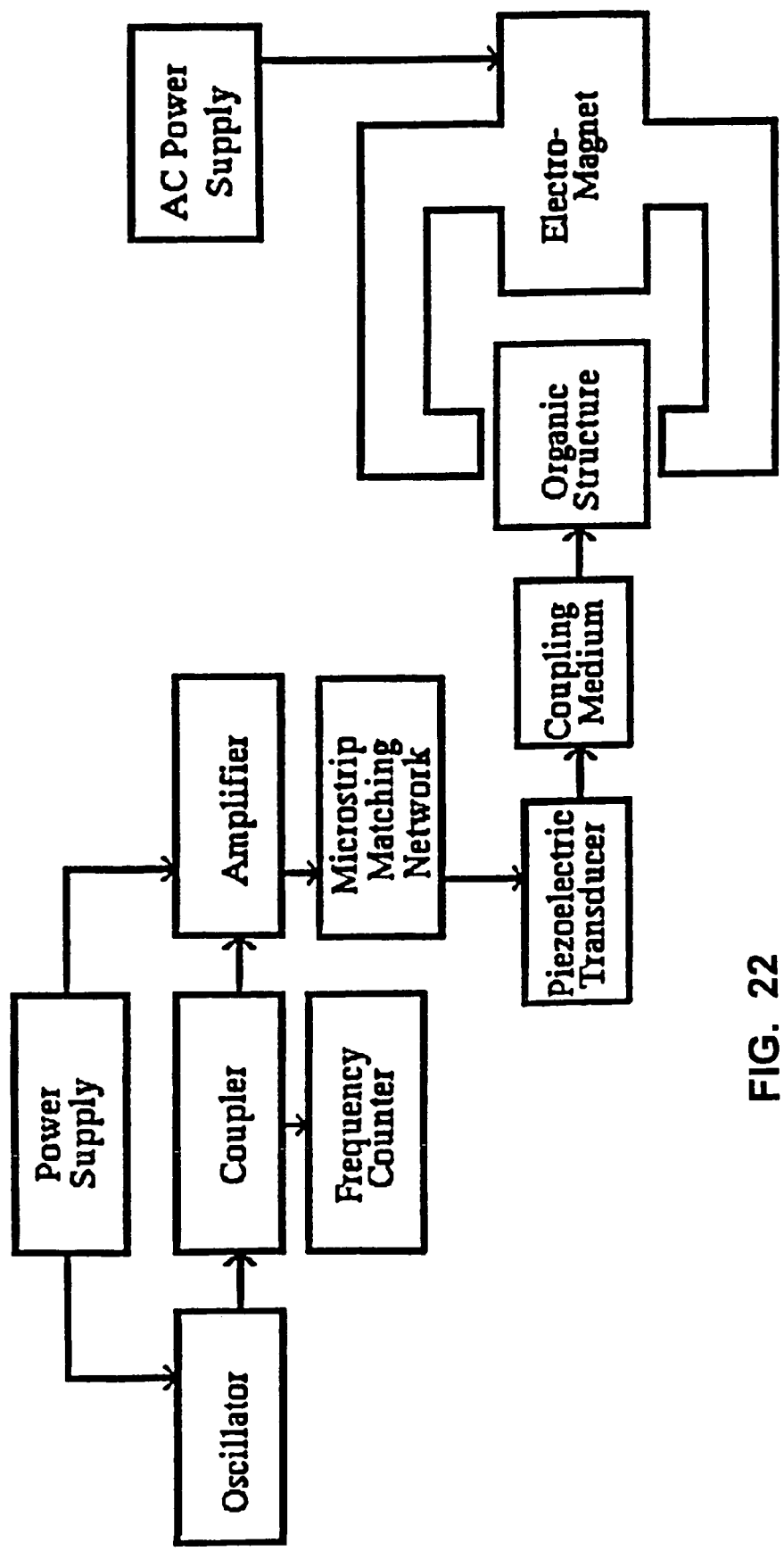
FIG. 22 is a block schematic showing a method for disrupting viruses in vivo intravascularly with resonant acoustic and/or acousto-EM fields.
Figure 23:
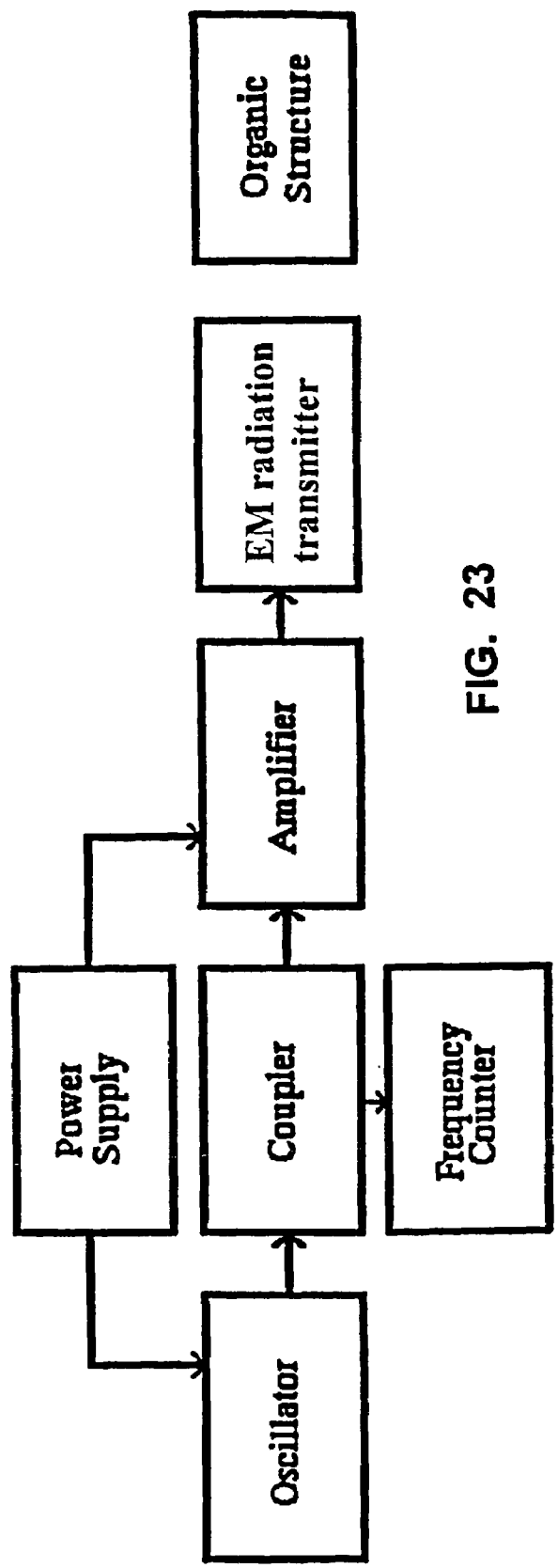
FIG. 23 is a block schematic showing a method for disrupting virus in a portion of a multicellular organism with resonant acoustic and/or acousto-EM field probe.

The present invention also provides a method to augment and/or disrupt viruses in an organ of a multicellular organism, as shown in FIG. 22, using resonant acoustic and/or acousto-EM fields. For instance, as in FIG. 16, including any and all embodiments, a human cadaver cornea for transplantation is placed in a form-fitting cup filled either with water or such other non-toxic acoustic conductive gel as is available commercially. A predetermined acoustic field (frequencies, harmonics, amplitude, mode, shape, etc.) is delivered to the cornea from a transducer tub through the coupling medium. Utilizing the magnetoacoustic effect, a magnetic field is placed perpendicular to the direction of the acoustic wave propagation, at a field strength which is a multiple of the acoustic frequency, thereby generating sinusoidal or peak-type resonance spikes in the acoustic power, and improving resonant acoustic penetration into the cornea without injuring the cornea tissue itself The present invention also provides a means to disrupt viruses in vivo in a portion of a multicellular organism using a resonant acoustic and/or acousto-EM field probe. For example, as shown in FIG. 23, a hand-held probe is fitted with an EM radiation generating device, as currently known to those skilled in the art. A predetermined EM radiation field (frequencies, harmonics, amplitude, mode, shape, etc.) replicating the acousto-EM signature representing the intrinsic dissipation pattern of a particular virus, is delivered to a predetermined portion of the organism, from the hand-held probe. For example, in a person afflicted with an upper respiratory tract infection (a "cold"), the treatment is delivered through the skin over the nose, throat, and sinuses, reversing the intrinsic energy dissipation pathway of the rhinovirus and inducing resonant acoustic oscillations which disrupt the rhinovirus.

Example 2

Disruption, Augmentation, Detection and/or Identification of Micro-organisms

Any micro-organism, such as bacteria, as well as structure and molecules contained or associated herewith, may be augmented, disrupted, detected and/or identified in vitro or in vivo using the methods of the present invention. Bacteria include, but are not limited to, those associated with animals, man, avians, reptiles, amphibians, insects, aquatic life, plants, fruit, soil, water, oil, fermentation processes for food production, and the like. In one embodiment the bacteria include but are not limited to Streptococcus sps., Staphylococcus sps., Hemophilus sps., Neisseria sps., Treponema sps., Salmonella sps, Shigella sps, Escherichia coli strains, Corynebacteria sps., Bordetella sps., Chlostridrium sps., Rickettsia sps., Chlamydia sps, Brucella sps., Mycobacterium sps., Borrelia sps., Mycoplasma sps., Lactobacillus sps., strains thereof and the like. Human illnesses caused by bacteria include pneumonia, skin and wound infections, heart valve infections, gastroenteritis, syphilis, gonorrhea, the plague, urinary tract infections, lyme disease, tuberculosis, cholera, typhoid fever, anthrax, tetanus, and gangrene.

Fungal infections include athlete's foot, ringworm, vaginal yeast infections, oral thrush, histoplasmosis, and cryptococcus.

Diseases in animals caused by bacteria, fungi protozoa and worms are similar to those in humans. Similarly, a wide range of micro-organisms infect plants, and even other micro-organisms are deemed to be beneficial (e.g., bakers yeast.).

Bacteria are first classified by staining characteristics as either Gram positive, or Gram negative. Bacterial response to staining is determined by the structure of the cell wall. Next bacteria are further classified by shape as either cocci (spherical) or rods (cylindrical.) Beyond that, the classification schemes generally involve various biochemical reactions.

Bacterial cell walls are composed of rigid peptidoglycan (mucopeptide or murien), a mixed polymer of hexose sugars (N-acetylglucosamine and N-acetyl muraric acid) and amino acids (the structural units of proteins, see below). As such, the cell walls are crystalline structures and are subject to vibrational effects from the use of acoustic energy. Thus bacteria are susceptible to augmentation, identification and detection, or disruption by resonant acoustic frequencies matched to their shape (sphere or cylinder), size, and composition. In addition, various organelles contained within the bacteria structure are also susceptible to specific resonant acoustic frequencies (i.e., pili, plasma membrane, flagellum, cytoplasmic inclusion bodies, basal bodies, capsule, spores, etc.). Finally, the compounds comprising the structure itself (crystalline proteins, etc.) also have unique resonant frequencies.

Fungi, protozoa, parasites, and worms are similar to bacteria in that the organisms are susceptible to the effects of specific resonant frequencies based on the size and shape of the entire organism, the size and shape of organelles making up a part of the organism, and the resonant characteristics of specific biochemical compounds making up the organism.

Any fungus, including yeasts, molds and mushrooms, protozoan, parasites or worms, as well as structures and molecules contained or associated therewith, may be augmented, disrupted and/or detected in vitro or in vivo using the methods of the present invention. These organisms include, but are not limited to those associated with animals, man, avians, reptiles, amphibians, insects, aquatic life, plants, fruit, soil, water, oil, fermentation possesses for food production, and the like. In one embodiment, these organisms include but are not limited to Crypto sporidia sps., Aspergillus sps, Trichophyton sps., Saccharomyces sps, Blastomyces sps., Coccidioides sps., Paracoccidioides sps., Penicillium sps., Rhizopus sps., Mucor sps., Neurospora sps., Microsporum sps, Streptomyces sps., Epidermophyton sps., Toxicara sps., Ascaris sps., Echinococcus sps., Giardia sps., Plasmodium sps., Trypanosoma sps., Schistosoma sps., Bruglia sps., strains thereof and the like.

At low acoustic and/or acousto-EM power inputs such as below $1 \times 10^{-5}$ W/m$^2$, the micro-organisms will be augmented in function and will emit a characteristic acoustic and/or acousto-EM signature which can be used to detect and diagnose the presence of the micro-organisms. At higher power inputs, the organisms will be disrupted and killed. In addition to the structures of bacteria, fungi, protozoa, and worms being susceptible to the vibrational resonant effects of acoustic and/or acousto-EM energy, they may also function as piezoelectric structures, intrinsic dissipation, acoustoelectric, and magnetoacoustic structures.

The present invention takes advantage of the composing parts of structures, or the entire organism of bacteria, fungi, protozoa, and worms for the purpose of augmentation, identification, and/or physical disruption of the micro-organism structures using acoustic and/or acousto-EM energy at specific resonant frequencies, and the piezoelectric, intrinsic dissipation, acoustoelectric and/or magnetoacoustic properties of any and all structures involved, either alone or in combination with a resonant acoustic field.

Unlike treatment in the prior art using ultrasound, the present invention uses specific resonant frequencies, which can be used to treat a multilayer organism. The invention also has the potential to augment the functional activity of micro-organisms deemed beneficial such as baker's yeast, wine yeast, lactic acid bacteria (wine and cheese,) petroleum yeast, and microbes producing specific amino acids, antibiotics, enzymes, or other chemicals. The functional activities may include growth, metabolism, oxidation or reduction activity and the like.

Figure 24A:
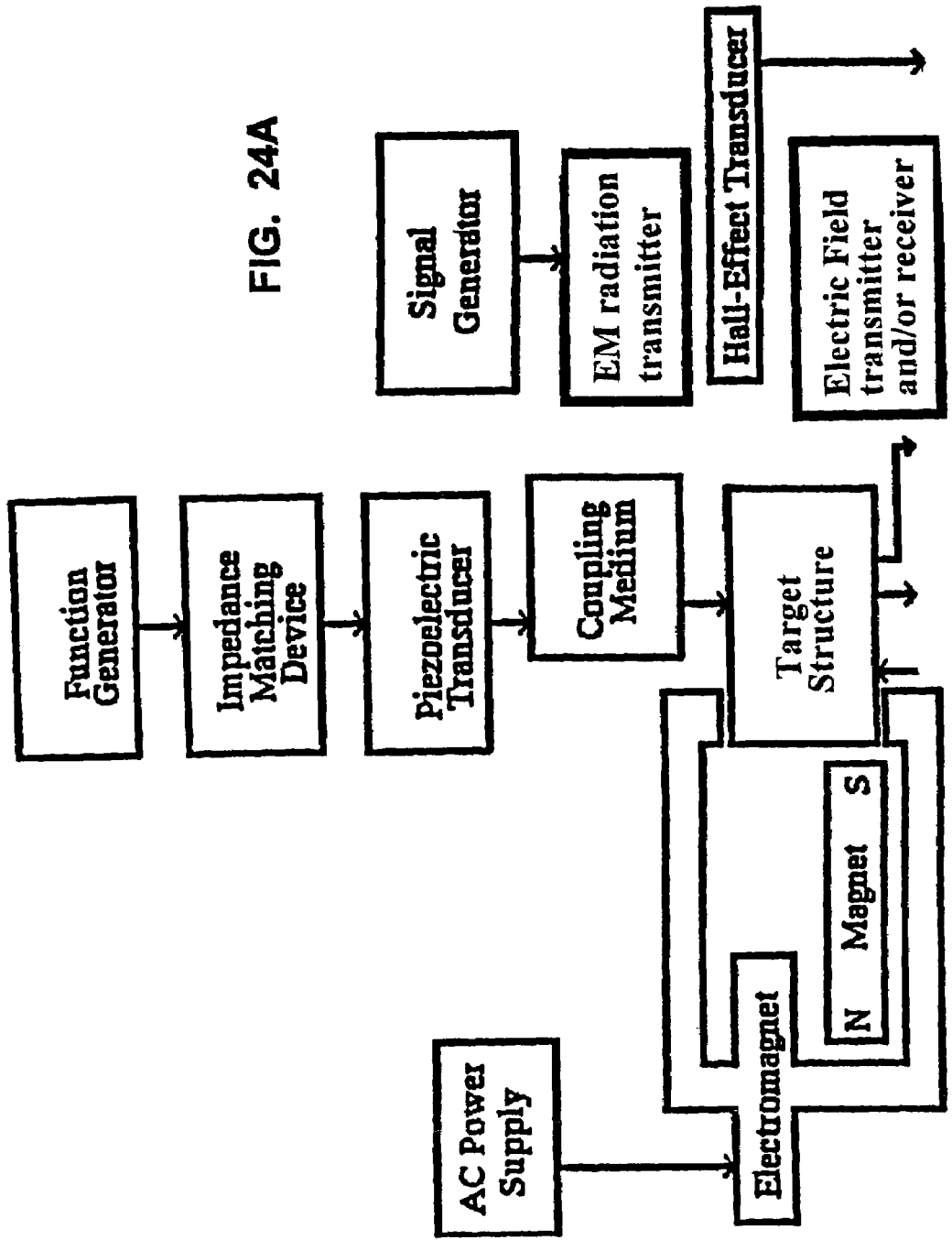
FIGS. 24 A & B are block schematics showing a method for determining resonant acoustic and/or acousto-EM frequencies of microorganisms.
Figure 24B:
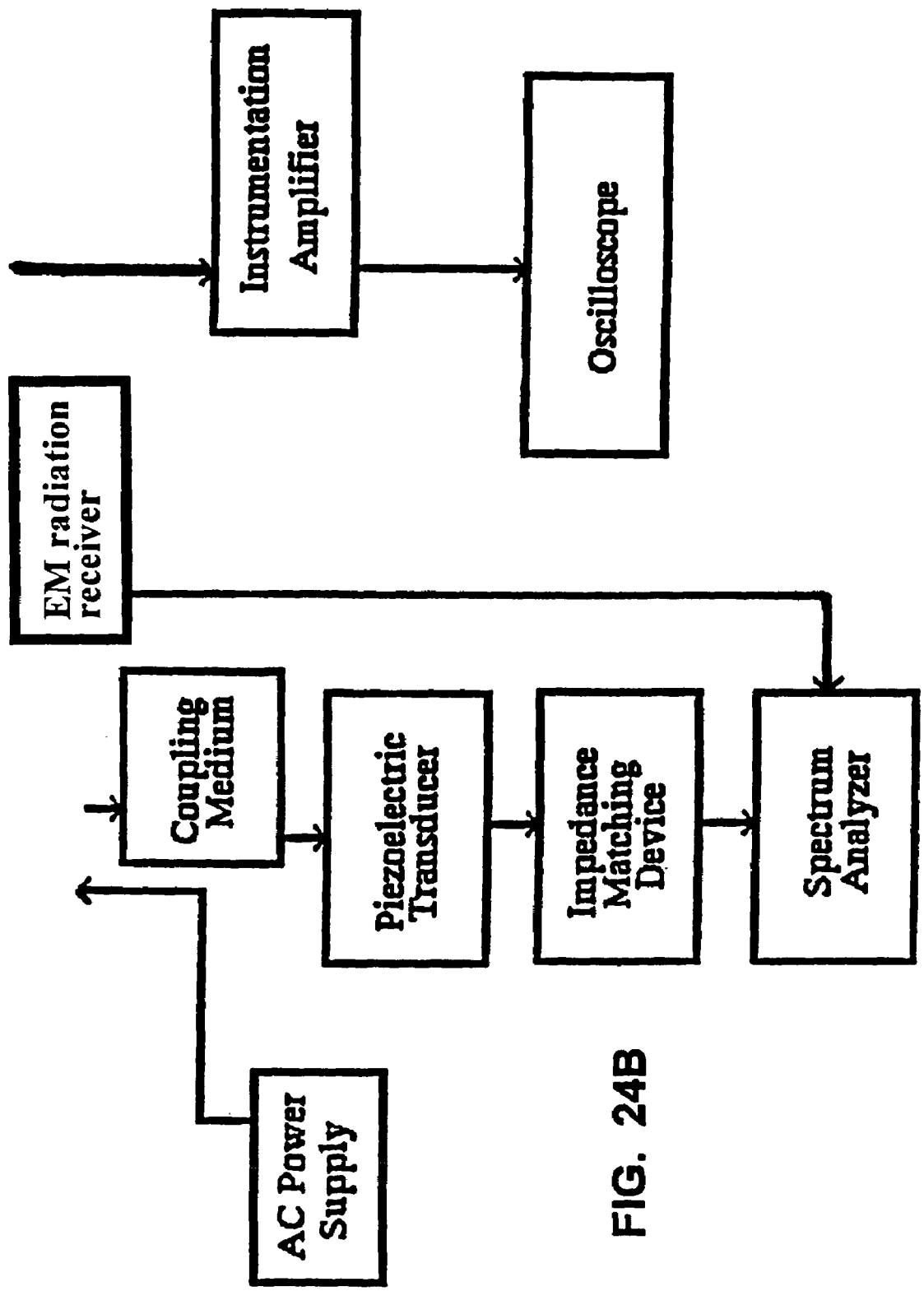

In one embodiment, the present invention allows the resonant acoustic and/or acousto-EM frequencies of micro-organisms to be determined in vitro as shown by the apparatus described in FIGS. 12 and 24 A & B, including any and all embodiments, with transducers designed for lower frequencies in the MHZ range (as provided commercially by Matec Instruments). For example, in a meat packing plant concerned with the contamination of beef by bacteria, in particular, E. coli a similar device can be used to screen the meat for bacteria, in a relatively short time span when compared to conventional culturing methods. First a swab of the meat surface is taken, and placed into a sterile test tube containing sterile saline at physiologic pH. A predetermined amount of the solution is pipetted onto a standard test disc, which is clamped between two transducers. Resonant or resonant harmonic acoustic frequencies are scanned for in the test sample, thereby screening for the presence or absence of potentially harmful E coli bacteria. Inspection of meat is done more efficiently and reliably than by current methods.

Figure 25:
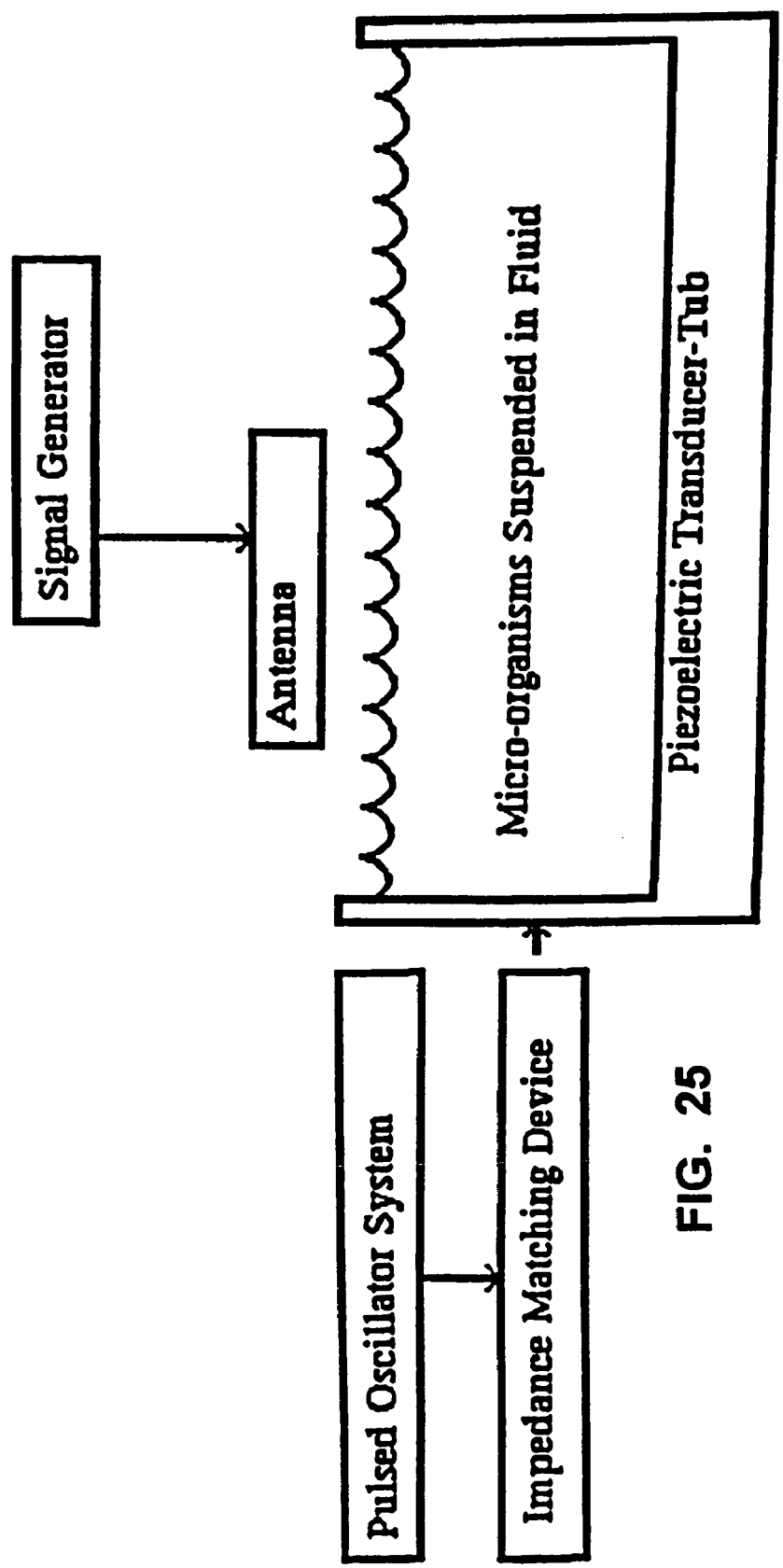
FIG. 25 is a block schematic showing a method for augmenting microorganisms with resonant acoustic and/or acousto-EM fields.

The present invention also allows the resonant acoustic and/or acousto-EM fields of micro-organisms to be used to augment these biologic organisms or their structures. For example, as shown in FIG. 25, the bottom of a beer fermentation vat is fitted with acoustic transducers of appropriate frequency and power output to augment the function of the special strains of Saccharomyces cerevisiae yeast. This yeast is currently used to ferment beer for a period of 5 to 10 days, however, with resonant acoustic augmentation, the fermentation time is reduced. The most efficient power output level can be determined by quantitatively detecting concentration of yeast and conversion of starch and/or sugar molecules to alcohol compound.

Figures 26, 27:
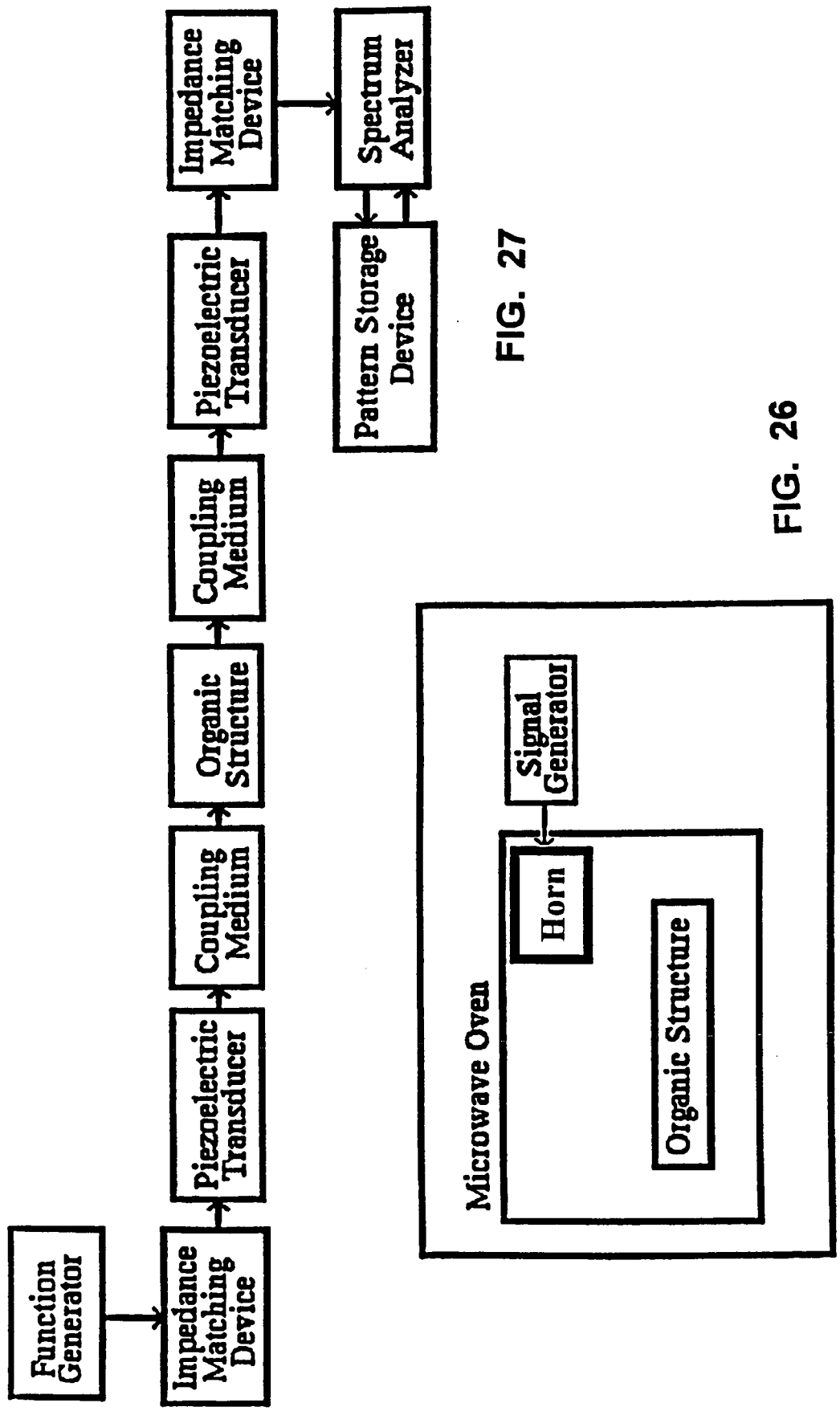
FIG. 26 is a block schematic showing a method for disrupting microorganisms with resonant acoustic and/or acousto-EM fields.
FIG. 27 is a block schematic showing a method for determining resonant acoustic and/or acousto-EM frequencies of arthropods.
Figure 28:
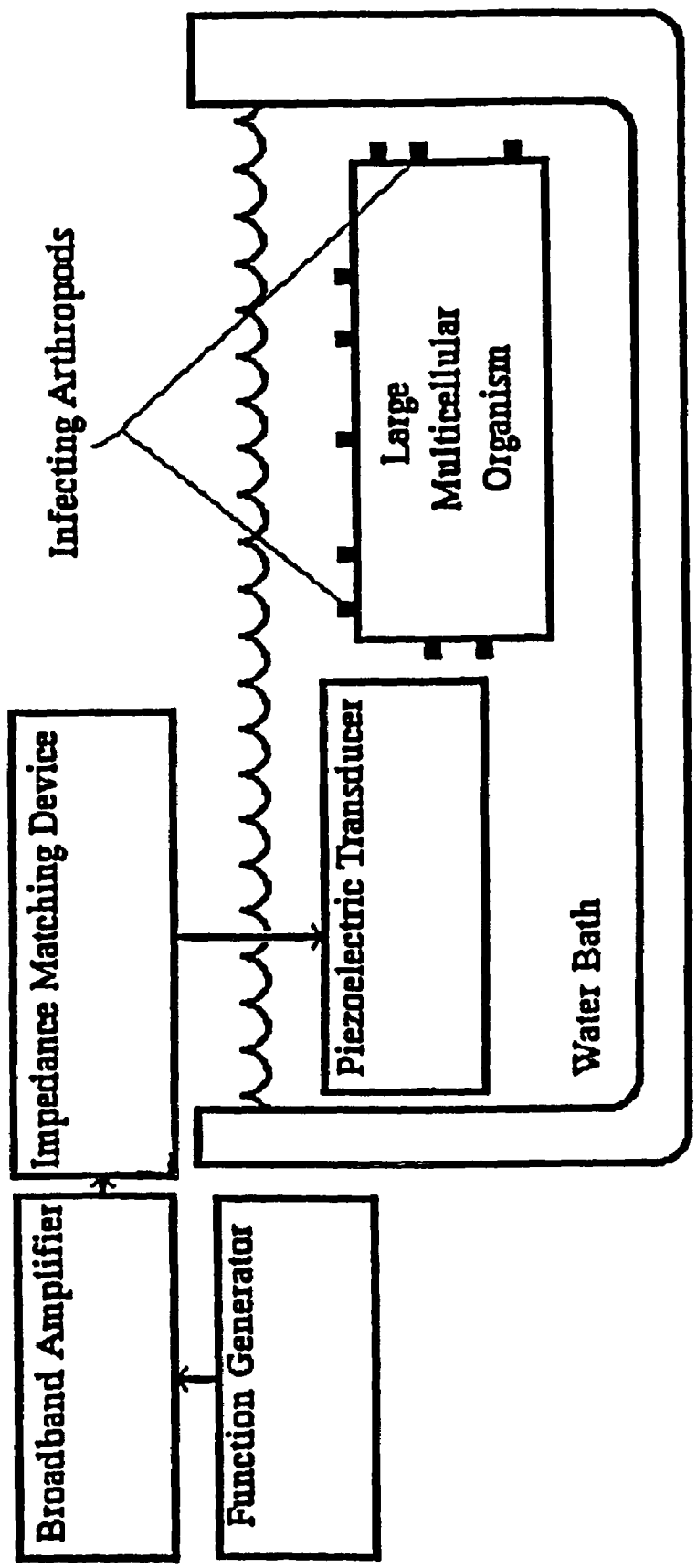
FIG. 28 is a block schematic showing a method for disrupting arthropods using resonant acoustic and/or acousto-EM energy.

The present invention also allows the resonant acoustic and/or acousto-EM fields of micro-organisms to be used to disrupt these biologic organisms or their structures. For example, as shown in FIG. 26, a commercial kitchen microwave is fitted with two (2) EM radiation horns—one for cooking and one for the resonant acoustic and/or acousto-EM frequencies of the common food pathogens such as E. coli and Salmonella sps. Prior to roasting, grilling, or such other food preparation method as may be desired, the home chef may decontaminate the meat or other food product of any potential pathogens by using the decontaminate cycle on the microwave oven.

Acoustic resonance measurements were conducted on several types of bacteria to determine the resonant acoustic frequency of the bacteria. A Matec high frequency 7000 pulse modulator and receiver was used in conjunction with a Matec automated data acquisition system and an oscilloscope. Klebsiella pneumoniae (American Type Culture Collection #13883) was grown on standard growth media. A Matec 90 MHz, ⅜" diameter transducer surface was cleaned and sterilized with alcohol. Live Klebsiella was placed on the surface of the transducer. Resonant acoustic spectroscopy was performed in the acoustic range of 100–200 MHz. A resonant acoustic frequency was detected for the Klebsiella at 125–130 MHz with a centered frequency at 127.5 MHz. This was presumed to be a resonant subharmonic frequency.

The same measurements were performed on E. coli bacteria (American Type Culture Collection # 25922) using the same equipment. A resonant acoustic frequency was detected for the E. coli with a centered frequency of 113 MHz. This too was presumed to be a resonant subharmonic frequency.

Example 3

Detection and Disruption of Infectious Arthropods

Arthropods include a diverse group of insects that infest and feed on the blood of humans and animals. Examples include lice, fleas, ticks, mosquitoes, mites, sandflies, and tsetse flies. Aside from the general discomfort and annoyance that these arthropods produce when they infest a human or animal, the true danger of infestation lies in the diseases transmitted by the arthropods. These diseases, in general, cost the world economy billions of dollars a year. The overall health status of the victims is impaired and they suffer loss of time, quality of life, and sometimes life itself Mosquitoes transmit dengue fever, yellow fever, encephalitis, hemorrhagic fever, malaria, and lymphatic filariasis. Ticks transmit encephalitis, Lyme disease, relapsing fever, and Rocky Mountain spotted fever. Fleas transmit the plague (Yersinia) and typhus. Lice transmit typhus. Mites transmit rickettsial pox. Flies transmit African sleeping sickness, leishmaniasis, and Chagas disease.

The distinguishing feature of arthropods is the chitinous exoskeleton, which covers the body and legs. Chitin is a long, unbranched molecule consisting of repeating units of N-acetyl-D-glucosamine. It is found abundantly in nature and forms the hard shell of insects, arthropods, crustaceans, mollusks, and even the cell walls of certain fungi. As such, chitin is a crystalline structure and is subject to the effects of acoustic and/or acousto-EM energy. Thus arthropods are susceptible to detection and disruption by resonant acoustic frequencies matched to their shape (sphere or cylinder), and size. In addition, various organs or appendages contained within the arthropod structure are also susceptible to specific resonant acoustic frequencies. Finally, the compounds comprising the structure itself (chitin, crystalline proteins, etc.) also have unique resonant frequencies.

At low acoustic power inputs, the infectious arthropods will emit a characteristic acoustic and/or acousto-EM signature which can be used to detect and diagnose their presence. At higher power inputs, the arthropods will be disrupted and killed. The specific range of intensities used for detection or disruption will be determinant on the structure and the intensity can be determined using standard methods known to those skilled in the art such as discussed above. In addition to the structures of arthropods being susceptible to the effects of acoustic and/or acousto-EM energy, they may also function as piezoelectric structures.

The present invention takes advantage of composing parts of the structures or the entire organism of arthropods for the purpose of identification and/or physical disruption of the arthropod structure using acoustic and/or acousto-EM energy at specific resonant frequencies and patterns, and using them as piezoelectric, intrinsic dissipation, acousto-electric, and or magnetoacoustic structures, either alone or in combination with a resonant acoustic field.

Figure 29:
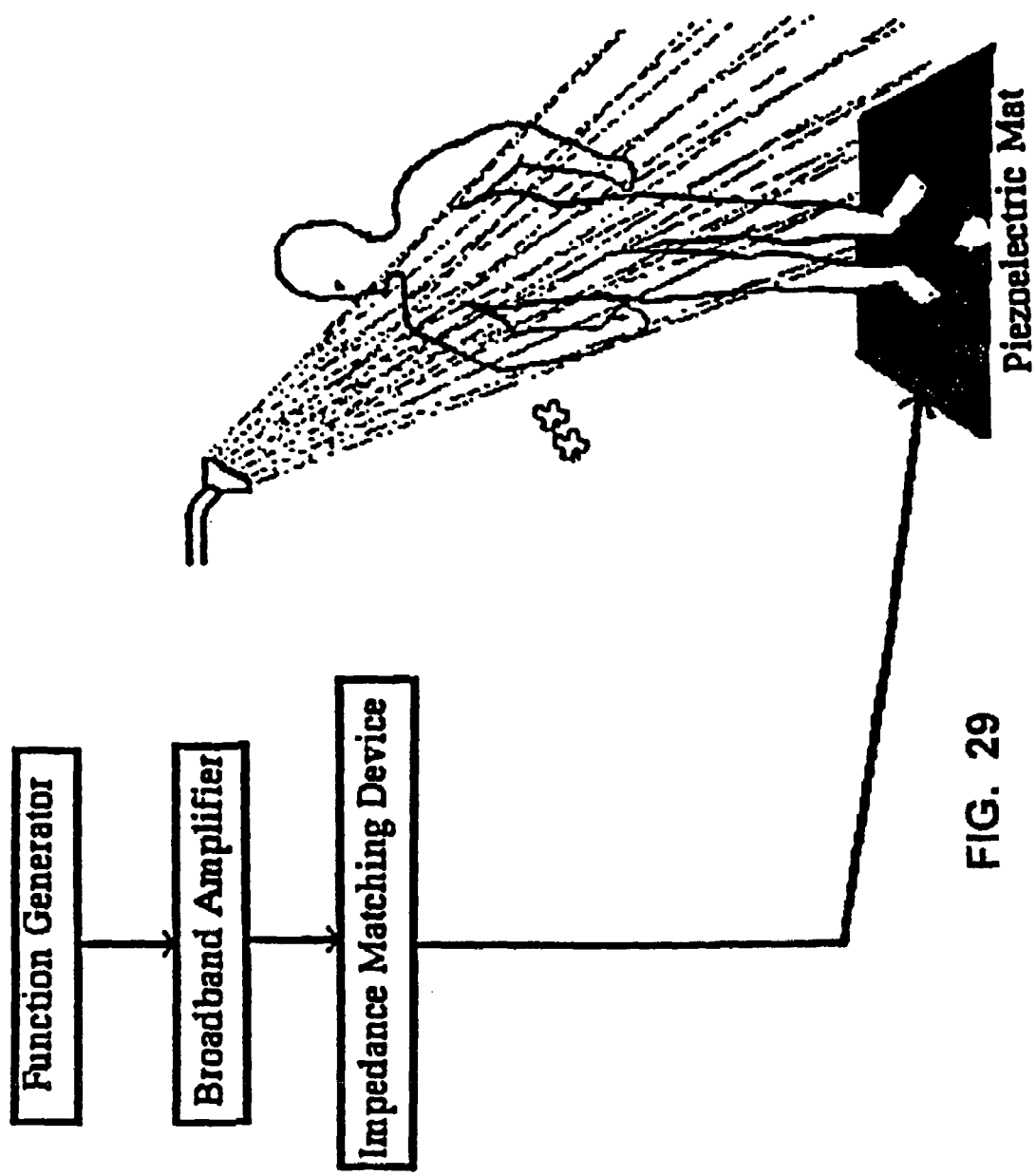
FIG. 29 is a block schematic showing a method for augmenting and maintaining normal bone structure in individuals with osteoporosis.

The methods of the present invention allow the resonant acoustic frequencies of arthropods to be determined and utilized, with devices of appropriate frequency similar to those previously described. For example, researchers capturing and cataloging thousands of insects and other arthropods in an effort to identify the source of an infectious agent such as Ebola, a hemorrhagic fever, or encephalitis, could use an apparatus such as that shown in FIG. 27. The portion of the acoustic spectrum containing the resonant frequencies of the infectious agent in question is scanned. Known resonant frequencies of arthropod materials are fed into the negative lead of the spectrum analyzer and cancel out their component resonant frequencies in the positive lead sample scan. The remaining frequencies are analyzed for the resonant acoustic signature of the offending microorganism. This provides a means to readily identify the host reservoir of an infectious agent without the need for expensive and time-consuming studies.

The present invention also provides a means to kill infecting arthropods on a large organism, for example fleas on a dog or human, as shown in FIG. 28. High kHz to very low MHz transducers are fitted onto a bathtub-type apparatus. The resonant acoustic frequencies for fleas are delivered through the water to the surface of the animal. High power outputs for deep tissue penetration are not required, as the infectious arthropods are restricted to the surface or outermost layers of the dog or human. The same method can also be used, for example, to de-flea or de-louse bedding and linens in a washing machine.

Example 4

Augmentation of Bone Growth

Bone demineralization in humans is a significant health care problem Thousands of elderly people sustain fractures of the hip, leg, or arm due to this bone demineralization (osteoporosis). These injuries cost the American health care system billions of dollars a year, for treatment, surgery, and rehabilitation after the injury. In addition, the overall health status of the victims is impaired, and they suffer loss of time and quality of life due to these fractures. Other conditions which contribute to bone matrix loss include weightlessness (e.g., in outer space) and prolonged confinement to bed. People in certain occupations may benefit from an increase in the normal bone density. Examples include professional athletes, military personnel, and jobs requiring exposure to increased atmospheric pressures (e.g., undersea diving).

Living bone is organized in a calcium based crystalline structure of hydroxyapatite, doped with copper, and embedded in collagen fibers. The application of force to the collagen fibers in the bony matrix, through mechanical pressure or gravitational fields, stimulates the piezoelectric effect and flow of ions via fluid channels in bone. This small electrical charge, in turn, acts as a signal to the body's osteoblasts to deposit more hydroxyapatite. As the hydroxyapatite density increases, the bone becomes stronger. Thus, bones maintain their normal structure and density in response to pressures and forces encountered in normal daily activities, via a piezoelectric effect.

With aging, normal copper doping is lost, and the piezoelectric effect diminished. The result is that hydroxyapatite density is not maintained, and the elderly suffer from osteoporosis and bone fractures. The same thing occurs in the absence of normal activity (weightlessness and confinement to bed), with subsequent absence of the normal piezoelectric effect and ionic current flows.

Bone is a crystalline piezoelectric structure and as such is subject to the vibratory effects of acoustic energy. The operative process behind normal physiologic bone density maintenance is the generation of hydroxyapatite molecular movement within collagen fibers, compressed by macro-pressures. These occur from daily activities, and stimulate the piezoelectric and subsequent bone building osteoblastic effects.

This molecular movement and the collagen fiber compression can also be generated from micro-pressures within the semiconductor matrix of bone. Thus understood, micro-pressures can be produced by acoustic energy waves.

In addition to the piezoelectric effect, since bone is a piezoelectric and semiconductor structure, it will exhibit the acoustoelectric, intrinsic dissipation and magnetoacoustic effects. Conditions with diminished bone semiconductor function (osteoporosis) and/or decreased macro-pressures (weightlessness and bed confinement) can be effectively treated through application of acoustic micro-pressures which generate a biological piezoelectric effect, and/or also via acoustic resonance, intrinsic dissipation, acoustoelectric and magnetoacoustic effects.

Prior literature describes the use of non-resonant ultrasound to speed the rate of healing of bone fractures, however, the mechanism causes gross disruption of the bone tissues, which in turn damages the microscopic capillary bed in bone, with leakage of serum and cells into the bony matrix, and with subsequent bone mineralization. The literature also describes attempts to use ultrasound to detect resonant frequencies of the structure of entire bones (femur and ulna) to diagnose a bone as normal or defective. However, the use of resonant acoustics and/or acousto-EM frequencies to activate the piezoelectric effect is not described. No consideration is given in the prior art to using bone as a living transducer for the piezoelectric, intrinsic dissipation, acoustoelectric, and magnetoacoustic effects, either alone or in combination with a resonant acoustic field.

The present invention takes advantage of the crystalline, piezoelectric structure of bone for the purpose of augmenting bone growth and calcification. The invention has the potential to significantly reduce the number and severity of bone fractures suffered by victims of osteoporosis. The invention has the potential to speed the healing process of fractures. Other conditions which contribute to bone matrix loss, such as weightlessness (i.e., in outer space), or prolonged confinement to bed, would also benefit from the invention. The invention has the potential to aid people in occupations which would benefit from an increase in their bone density (athletes, military personnel, and jobs requiring exposure to increased atmospheric pressures such as undersea diving.) The invention also has potential veterinary applications. Unlike prior treatment using ultrasound, the present invention uses resonant acoustic and/or acousto-EM frequencies of bone to stimulate at least the piezoelectric effect for augmentation of bone growth without affecting neighboring tissue.

The methods of the present invention provide a means to augment the growth and maintenance of bone using resonant acoustic and/or resonant acousto-EM energy. For example, as shown in FIG. 29, a sheet of piezoelectric material is fitted into a shower mat device. When an elderly person, prone to osteoporosis, showers the mat is activated. Water in the shower acts as a conductive medium and primary or harmonic resonant frequencies are delivered through the soles of the feet, along the lines of force, up into the legs and hips. The piezoelectric effect in bone is activated and bone density is increased.

Figure 30:
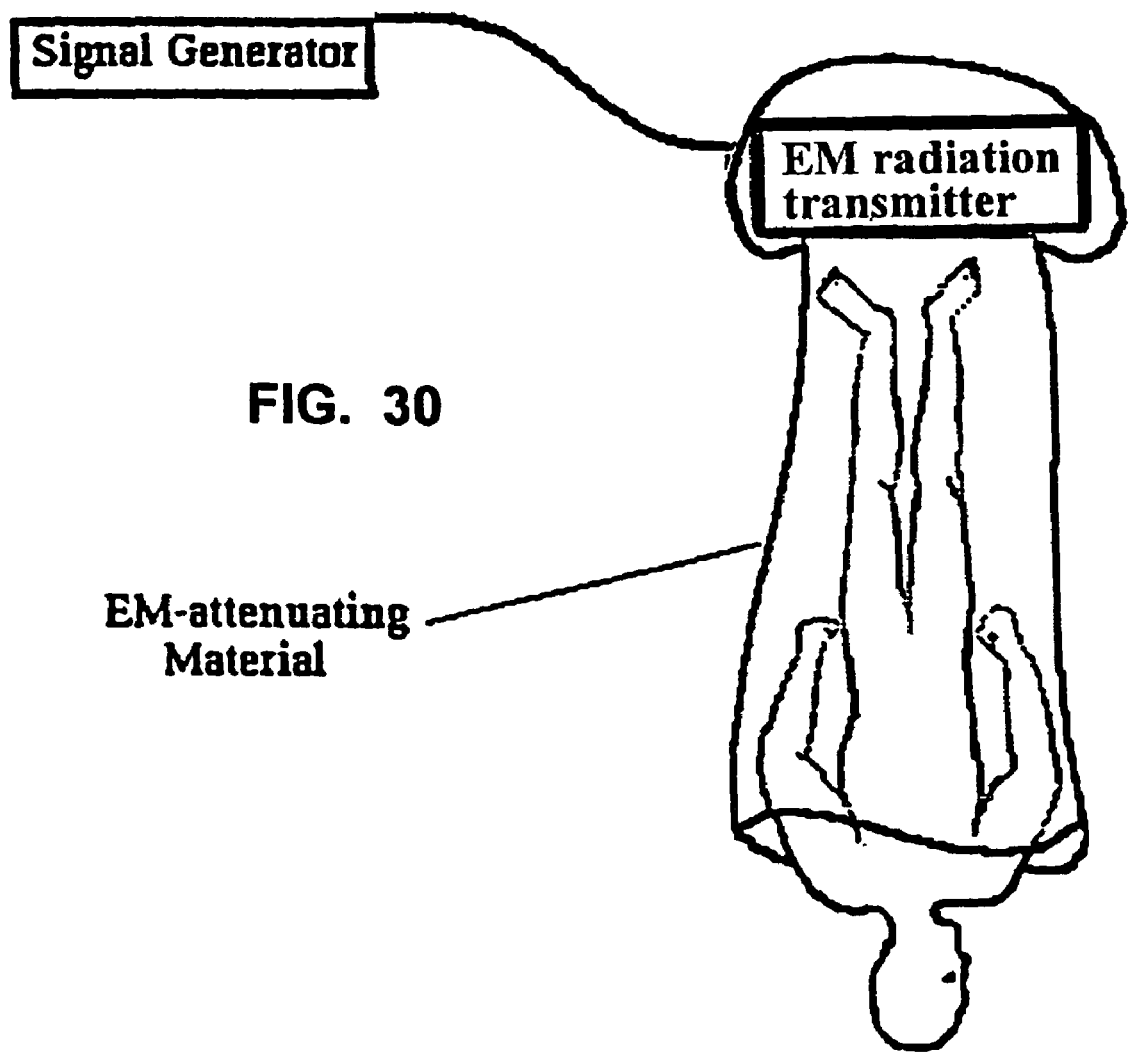
FIG. 30 is a block schematic showing a method for maintaining normal bone structure in normal individuals during weightlessness.

The present invention provides a method to augment the growth and maintenance of bone using resonant acoustic and/or acousto-EM energy, for example, as also shown in FIG. 30. The sleeping/tether bags used by astronauts during conditions of weightlessness are fitted with EM radiation transmitters in the foot of the bags. The bags are made of EM absorptive materials. The tethers that anchor the sleeping bags to the space vessel include the cables to connect the antennas to signal generators in the space craft. While sleeping, the bone maintenance devices in the sleeping bag are activated, delivering EM radiation to the astronauts at a resonant frequency that activates the piezoelectric effect in bone, and thus, maintains their normal body density. Extraneous EM radiation which might interfere with other equipment on board is blocked by the EM absorptive materials in the sleeping bags.

Example 5

Disruption and Detection of Benign or Malignant Tissues or Masses

There are a wide variety of tissue masses, both benign and malignant, which afflict humans and animals. Many tissue masses are encapsulated or are contained within a restricted area in the body. Nearly all benign tumors grow and expand slowly, developing a fibrous capsule, and producing a discrete, readily palpable and easily movable mass. Examples of benign tumors include fibroma, lipoma, chondroma, osteoma, hemangioma, lymphangioma, meningioma, leiomyoma, adenoma, papilloma, polyps, condyloma, fibroadenoma, and rhabdomyoma. Most malignant tumors are invasive and metastasize, however, notable exceptions are gliomas and basal cell carcinomas. Other tissue masses causing disease include emboli, thrombi, abscesses, stones, and foreign bodies.

By virtue of having a defined, discrete structure, many tissue masses are susceptible to the disrupting effects of acoustic energy at resonant frequencies matched to their size and shape. Prior art contains many applications for the use of acoustics at non-resonant frequencies to detect and even disrupt tissue masses, but to date detection of tissue masses via resonant acoustic energy and disruption of tissue masses via acoustic energy at resonant frequencies has not been disclosed.

In addition to tissue masses being susceptible to detection and disruption by resonant acoustic frequencies matched to their shape and size, the components comprising the tissue mass itself (cell types, crystalline proteins, etc.) also have unique resonant frequencies susceptible to detection and disruption. At lower power inputs, certain tissues or masses can be augmented in growth or metabolism, providing a supplemental technique for tissue culturing, regeneration, and growth.

Depending on their structure, certain tissue masses or types may also exhibit resonant acousto-EM effects as well as functioning as piezoelectric, intrinsic dissipation, acoustoelectric, and/or magnetoacoustic structures.

The present invention takes advantage of the discrete shape, size, and composition of numerous benign and malignant tissues and masses to cause the identification, augmentation, detection, and/or disruption of those structures using acoustic and/or electromagnetic energy at specific resonant frequencies. Unlike prior treatments using ultrasound, the present invention uses specific resonant acoustic and/or electromagnetic frequencies, which can be used to treat a multilayer organism by targeting a specific structure therein. It combines the known tumor/mass detection abilities of acoustic energy (diagnostic ultrasound) with the disruptive characteristics of acoustic and/or electromagnetic energy at resonant frequencies. The invention also has the potential to augment the growth and function of various tissues and masses, where desirable.

Figure 31:
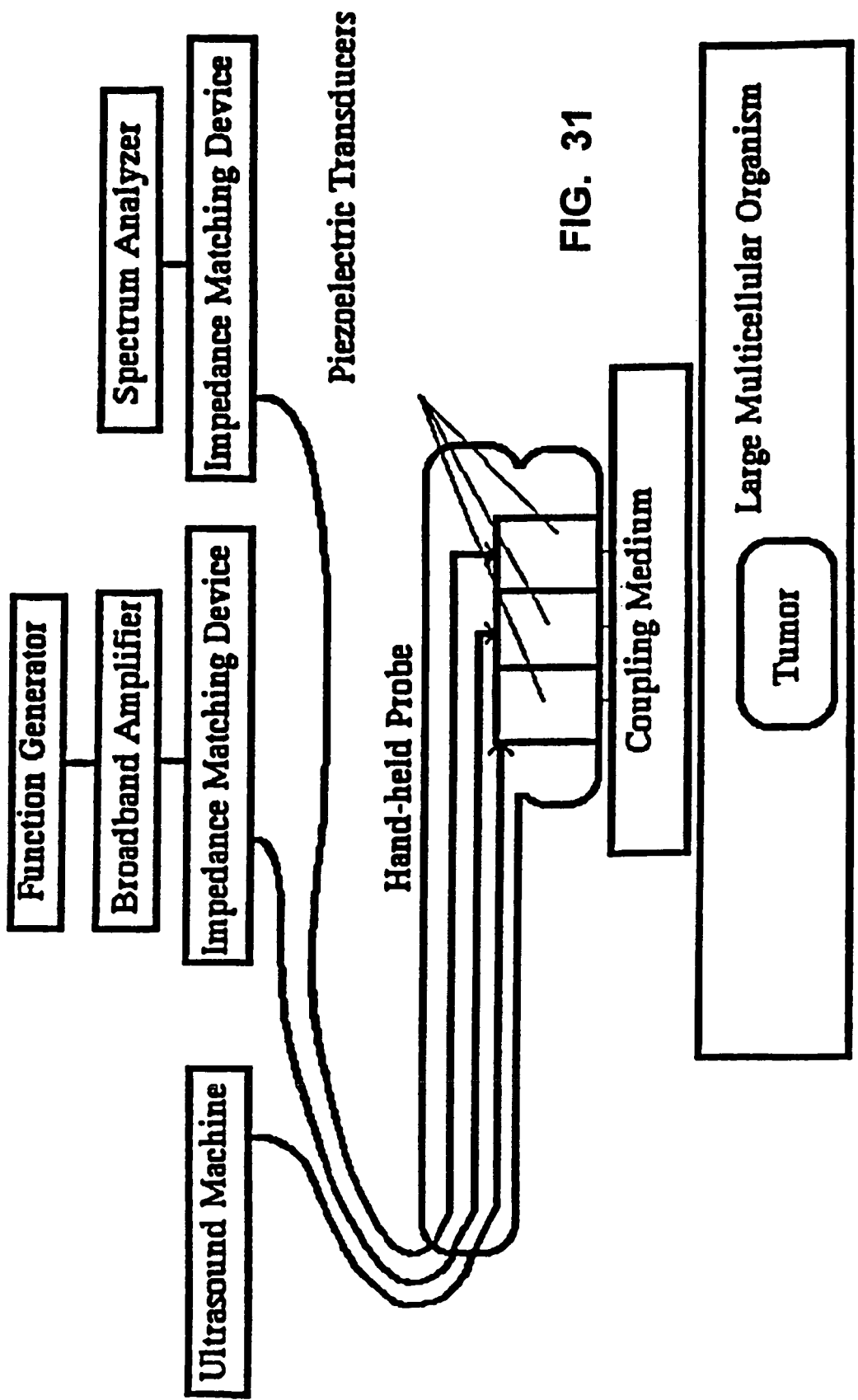
FIG. 31 is a block schematic showing a method for detecting benign or malignant tissue types using resonant acoustic and/or acousto-EM energy.

The present invention provides a means to detect and disrupt benign or malignant tissues and/or tissue masses using resonant acoustic and/or acousto-EM energy. For example, as shown in FIG. 31, an acoustic transducer designed with standard echo-reflective capabilities is used to determine the size and dimensions of a tissue mass. Based on the calculated resonant frequencies, a range is scanned to determine the precise resonant frequencies. Then one or more of those frequencies are delivered to the mass, disrupting its structure and allowing subsequent resorption of the mass by the body.

Also, the present invention provides a means to detect benign or malignant tissue types using resonant acoustic and/or acousto-EM energy, using the apparatus described in FIGS. 12 and 19 A &B, including any and all embodiments, the cell test disc or tissue preparation is placed between two transducers and the frequencies are scanned looking for resonant peaks and EM patterns. Differences in the resonant peaks and EM patterns will differentiate between tissue types, for example between normal epithelial cells and cancerous epithelial cells.

Example 6

Augmentation, Detection and/or Disruption of Biochemical Compounds or Tissues

Biologic organisms are composed of many biochemical compounds including nucleic acids, carbohydrates, lipids, amino acids, and steroids. Many biochemical compounds align themselves in regularly repeating patterns: in other words they adopt crystalline forms. Examples of biochemical crystals include insulin, hexokinase, aldolase, hemoglobin, myoglobin, and spectrin. In addition, certain tissues or cell structures adopt crystalline form such as bone, muscle fibers, and connective tissue fibers for the former, and cell membranes, Na/K membrane pumps, and visual rod receptors for the latter.

The biochemical compounds from which biological organisms are composed have their own unique resonant frequencies, based on their innate crystalline structure. Many of the biochemical compounds are also piezoelectric, intrinsic energy dissipation, acoustoelectric, and magnetoacoustic structures. As such, biochemical compounds are subject to the augmenting, disrupting, and/or detecting features of resonant acoustic and/or acousto-EM energy. The present invention uses specific resonant acoustic and/or acousto-EM frequencies, which can be used to treat a multilayer organism. The present invention also has the potential to utilize piezoelectric, intrinsic energy dissipation, acoustoelectric, and/or magnetoacoustic effects to achieve desired results, either alone or in combination with a resonant acoustic field.

Example 7

Stimulation or Disruption of Proteoglycans Adhesive Units Between Cells Yielding A Skin Welding Scalpel The present invention provides a method to stimulate and/or disrupt proteoglycans adhesive units between cells using resonant acoustic and/or acousto-EM energy. Millions of operations are performed on humans every year, using metal scalpels to make the incision. The use of such scalpels requires closure of the incisions with stitches, a period of healing, and invariably results in scar formation. In addition, millions of people suffer traumatic cuts, tears, or ruptures of the skin, again requiring closure of the wounds with stitches, a period of healing, and scar formation.

In multicellular organisms, the cells are held together by proteoglycans units, at the rate of approximately 1,600 per cell. These units are approximately 200 um long, with some variation between the species.

When an incision is made, or a traumatic break in a cell layer occurs, the cellular adhesions are ripped apart, some cells are ruptured, and blood vessels are torn open. White blood cells, platelets, and fibroblasts congregate in the extracellular space and eventually lead to the formation of a scar which readheres the tissues. During this healing phase the open tissues are much more susceptible to invasion by foreign organisms, and wound infection is a complication that must be constantly guarded against.

Even if the wound heals without the complication of infection, a scar still remains. Modern plastic surgery techniques try to either minimize or hide scars, but the formation of a scar is inevitable.

An energy field achieving acoustic resonance with the proteoglycans units at high amplitudes indicating high power levels will cause separation of the adhesive bonds between cells, thus producing separation of tissue layers, and in essence, a non-traumatic incision. The same energy field at lower amplitudes will cause readhesion of the adhesive bonds, with nearly instantaneous and scarless healing of the readhesed incision.

The present invention dramatically improves the surgical process by nontraumatically separating cell layers in the tissue, and by instantly readhering the cell layers with minimal or no scarring, using resonant acoustic frequencies. In so much as proteoglycans units may exhibit piezoelectric, intrinsic energy dissipation, acoustoelectric, and/or magnetoacoustic effects, the present invention has the potential to produce the above results using the electromagnetic energy pattern of the acousto-EM signature, either alone or in combination with a resonant acoustic field. The present invention also has veterinary and agricultural significance, i.e., treating wounds or performing surgery in livestock and poultry, and grafting of various plant tissues or branches from one plant to another.

Figure 33:
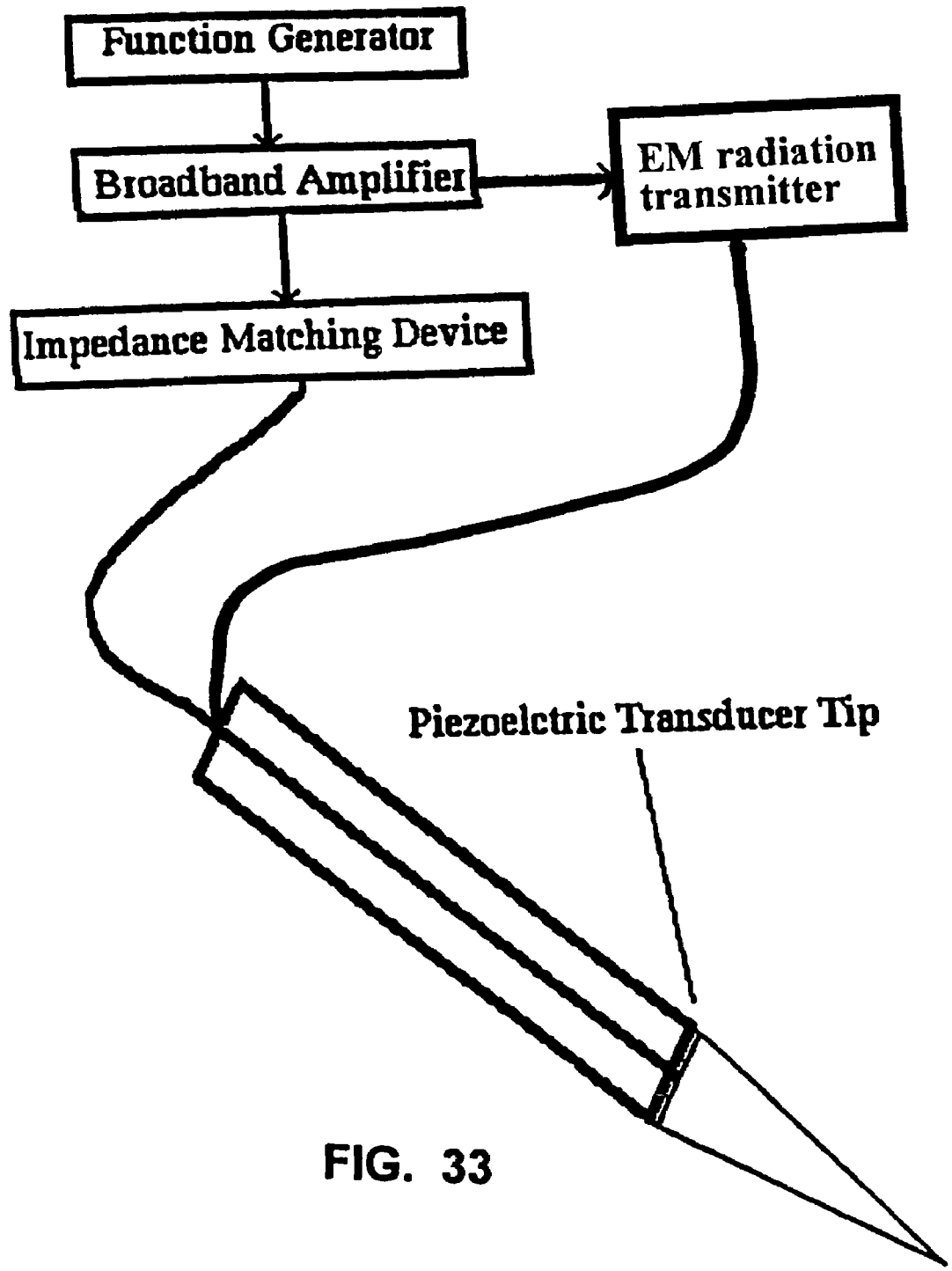
FIG. 33 is a block schematic showing a method for augmenting, identifying, detecting, and/or disrupting structures of multicellular organisms using resonant acoustic and/or acousto-EM energy.

For example, as shown in FIG. 33, a transducer tipped scalpel is used to produce an acoustic/acousto-EM wave of appropriate frequencies to disrupt the proteoglycans adhesive units between cells and create a surgical incision. At the end of the procedure the edges of the incision are held together, and another transducer of appropriate frequencies and type is passed over the incision, readhering the tissues.

Example 8

Augmentation. Detection and/or Disruption of Structures of Multicellular Organisms The augmentation, identification, detection, and/or disruption of multicellular organisms has many applications. The world population is plagued by a variety of pests such as insects, rodents, and mollusks. In other situations, the detection of various species in particular habitats is of importance to human activities. Finally, there are many multicellular organisms whose growth and augmentation are desired for harvesting of food, medicines, jewelry, etc. Pests can be eliminated by the use of resonant acoustic and/or acousto-EM frequencies matched to the size and shape of their body, parts of their bodies, or specific biochemical compounds contained in their bodies. For example, a resonant acoustic and/or acousto-EM frequency matched to the size of the head, thorax, or abdomen, could be lethal to bees, wasps, ant, or termites. Similarly, a resonant acoustic and/or acousto-EM frequency matched to the size and shape of a mouse's internal organ (brain, kidney, gonad, aorta, etc.) could be lethal to that animal. Mollusk pests such as the zebra shell mussel and barnacles could be controlled or eliminated through the use of resonant acoustic and/or acousto-EM frequencies matched to the size and shape of their eggs, internal organs, chitin shell, or cement/cement plate, etc.

Detection of various pest organisms such as termites, or desired organisms such as endangered species could be aided through the use and detection of resonant acoustic and/or acousto-EM frequencies specific for those organisms. The use of resonant acoustic and/or acousto-EM frequencies could potentially aid in the identification and differentiation of species and subspecies *throughout* the animal, plant, and microbiological kingdoms.

Examples of multicellular organisms whose growth and augmentation are desired for harvesting include plants and protein sources such as fish, clams, shrimp, chickens, and other livestock. Medicines, drugs, and chemicals harvested from a wide variety of plant and animal sources include hormones, perfumes, dyes, and vitamins. Other materials harvested from plant and animal sources are such an intrinsic part of human activities that they are simply too numerous to list (i.e., pearls, clothing fibers, building materials, leather, etc.) At lower power inputs of the resonant acoustic and/or acousto-EM frequencies, these organisms and their structures can be selectively augmented.

The present invention takes advantage of the discrete shape and size of numerous organisms to make use of resonant acoustic and/or acousto-EM frequencies specific to those organisms, for purposes of augmentation, identification, detection and/or disruption. Using the piezoelectric, intrinsic energy dissipation, acoustoelectric, and/or magnetoacousto effects, the invention has the potential to produce the above results by applying an electromagnetic energy pattern of the specific acousto-EM signature, either alone or in combination with a resonant acoustic field. The present invention has the potential to provide chemical-free control of numerous pests. The present invention also has the potential to provide for the detection and identification of numerous species of organisms. Lastly, the present invention has the potential to augment growth and metabolism in and of structures in various species deemed beneficial.

Figure 32:
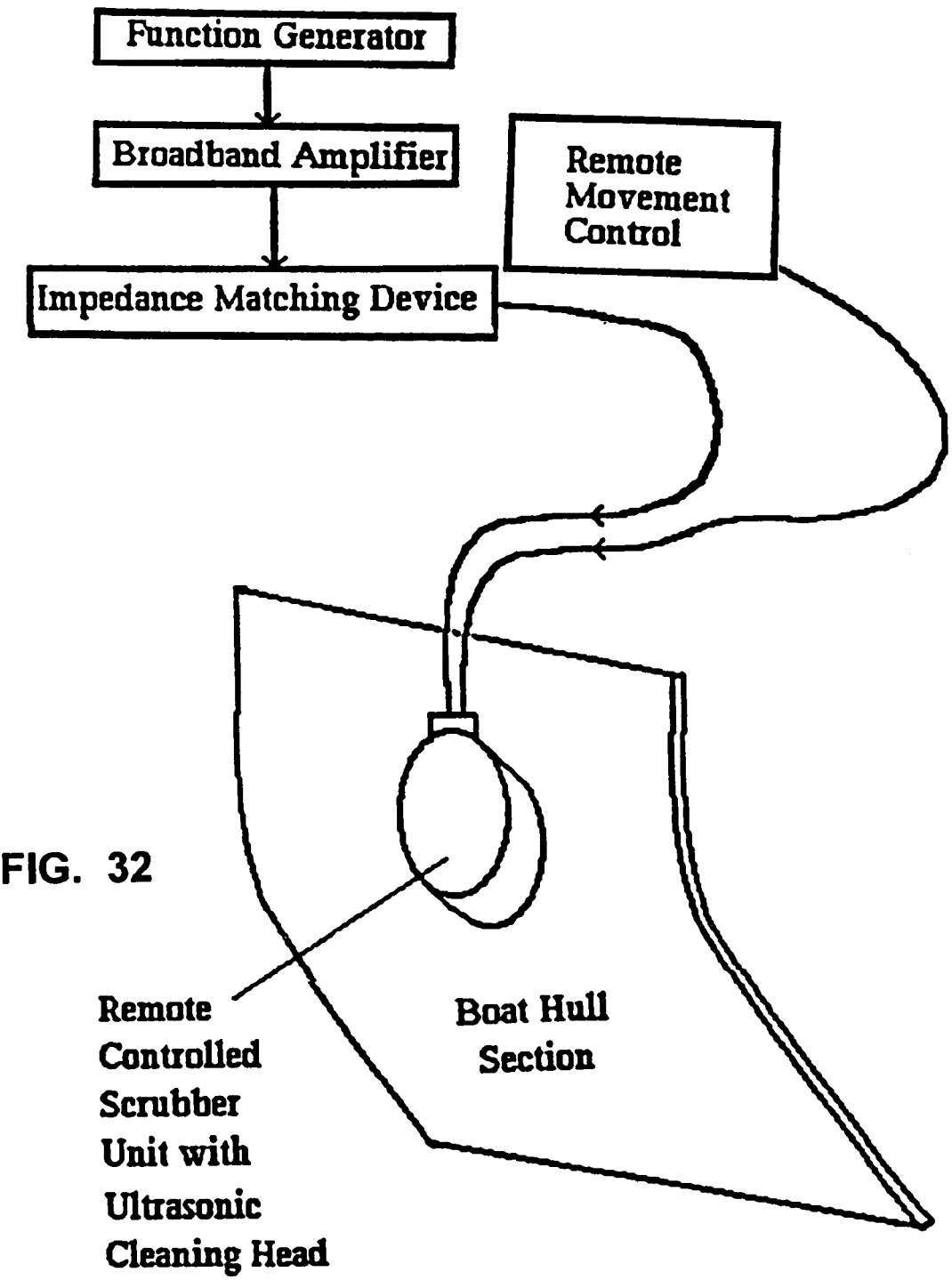
FIG. 32 is a block schematic showing a method for stimulating and/or disrupting proteoglycans adhesive units between cells using resonant acoustic and/or acousto-EM energy.

The present invention provides a means to augment, detect, and/or disrupt structures of multicellular organisms using resonant acoustic and/or acousto-EM energy. For example, as shown in FIG. 32, a transducer apparatus with the resonant frequency for the cement plate of barnacles (by which they attach themselves to the hulls of ships) is fitted into an underwater "scrubber" which is operated remotely from the deck of the ship via cables, or from inside the vessel via RF control. As the scrubber moves along the outside of the hull, the acoustic wave disrupts the cement plate of the barnacles, causing them to lose their grip on the hull and fall off into the ocean.

Example 9

Augmentation or Disruption of Growth Rate of Fish

The present invention provides for augmenting and/or disrupting the growth rate of fish in a commercial fishery as shown in FIG. 34.

Two breeding pairs of small fish were maintained in a 10 gallon fish tank at 80° F. The breeding pairs produced eggs which hatched in approximately 3–5 days. The three day old small-fry hatchlings were removed from the breeding tank and measured for acoustic resonance frequency profiles. The small-fries were placed, one at a time, in a drop of water on top of a 2.25 MHz Matec transducer to measure and determine resonant frequencies of the small-fries. All of the small-fry tested produced similar resonant acoustic frequencies profiles with minor individual variations. One of the strongest initial signals was at 2.4 MHz.

TEST A. The first test was conducted on two different groupings of small-fry, one group exposed to an acoustic resonant field and the other used as a control group. The experimental tanks were fitted with Matec 2.25 MHz acoustic transducers through a water tight grommet, through and parallel to the bottom of the tanks. One half of the small-fry were placed in a control tank that was connected to a transducer, but not activated. The other half of small-fry were placed in a tank with a transducer and an acoustic field was applied to the tank. The acoustic field transmitted at 2.4 MHz, continuously at 10 volts/sec. power. The small-fry that were in the control tank all thrived and grew while all the small-fry in the acoustic field died within two weeks.

TEST B. Another testing regime was conducted on small-fry wherein the small-fry were divided into three groups.

DAY 1. One third of the group was left in the breeding tank with parents as controls. One group was put in another small control tank, attached to a transducer but without activating power to the transducer. The third group was placed in a tank attached to a working transducer and the small-fry were exposed to an acoustic field of 2.4 MHz, using the pulse mode of the power source at 10 msec repetition rate with a 20 microsecond pulse width or duration. The voltage power was set at 300 volts/s, via the Matec TB 1000.

DAY 7. Within one week there was a noticeable difference in the sizes of the different groups of small-fry, the small-fry exposed to the acoustic resonance field being larger than the two control groups.

DAY 10. On the tenth (10) day of the experiment, all the small-fry were remeasured and the frequency exposing the small-fry in the acoustic exposed tank was reduced to 2.0 MHz but all other parameters remained the same. The acoustic exposed small-fry thrived.

DAY 14. Five of the small-fry in the small tank control group died.

DAY 16. Eighteen of the small-fry in the small tank control group had died by this time. The breeding tank group were unaffected. All remaining small-fry in all groups were measured using a centimeter ruler and the binocular microscope:

| | |
|---|---|
| Acoustic group | 7 mm long |
| Breeding tank control group | 6 mm long |
| Small tank control group | 5 mm long |

DAY 18. All but one of the small-fry in the small tank control group had died. The control group in the breeding tank were still alive and functioning and the acoustic resonance exposed group were thriving.

DAY 19. The resonant acoustic frequencies of the growing small-fry in the acoustic tank was measured again. The acoustic field was changed to 1.55 MHz, with all other parameters remaining the same except the pulse width of each repetition was reduced to 2 microseconds. This reduction of width of pulse had a marked influence on the growth of the small-fry indicating that the 20 microseconds was at the upper end of the power range for augmentation at these frequencies.

DAY 21. The sole remaining small-fry in the small tank control group was moved into the breeding control group. This sole small-fry was noticeably smaller than the other control groups but all control small-fry were noticeably smaller than the acoustic group.

DAY 41. In the acoustic group tank, the acoustic field was changed to 0.830 MHz, having all other parameters remain constant.

DAY 65. The acoustic field exposing the small-fry in the acoustic group tank was terminated. At approximately two months old, the acoustic resonance exposed fish were approximately the same size as much older 4 month old controls from an earlier control group and much larger than their counterparts in the breeding control group.

RESULTS: There was a significant difference in level of power input or intensity between TEST A and TEST B. In TEST A, the power was continuous at 10 Volts/sec. In TEST B the power was pulsed and the acoustic field was active at the most only 0.2% of the time. Therefore, even though the power was 300 volt/sec, the overall yield was only (300 V/sec×0.002) or 0.6 Volts/sec total power.

As the small-fry grew the acoustic resonant frequencies that induced function changes also changed due to difference in structure size and shape.

After termination of the acoustic field, the small fry were allowed to grow to maturity and breed. The fish exposed to acoustic energy at the resonant frequency matured and laid eggs significantly sooner than the control fish. No second generation effects were noted in offspring of either the acoustic exposed or control fish.

Example 10

Augmentation of Plant Growth

Testing was conducted to determine the effects of resonant acoustic energy on the germination and growth patterns of sugar snap peas. The seeds for the sugar snap peas were obtained from Lake Valley Seed Co., packed for lot 1997 lot A2B, 5717, Arapahoe, Boulder Colo., 80303.

Initially, the resonant acoustic frequency of pea sprouts was ascertained by determining the frequency for the maximum amplitude shown on an A-scan. By varying the frequency of the audio generator, the amplitude of the pea sprout was a maximum at the resonant frequency. Seven sugar snap peas were covered half way with room temperature water in a wide-mouth glass container and left on the counter to sprout. Six days later, the sprouts were tested as follows:

The Matec Ultrasonic Inspection System, with Tb 1000 and A to D data acquisition card was used the Tb 1000 settings were:

| Gain | 0–20 dB |
|---|---|
| Trigger | Internal + |
| Voltage | High |
| Rectify | None |
| LP filter | varied |
| HP filter | varied |
| Output level | 100% |
| Rep. Rate | 10.000 msec |
| Pulse Width | 2.00 usec |
| Frequency | 0.5–20 MHz |
| Mode | Through transmission |

A to D settings were:

| Data | On |
|---|---|
| Delay | none |
| Range | 12 usec |
| Signal path | RF |
| Volt. Range | 1 V |
| Channel | A/AC |
| Trigger | External + |
| Threshold | 1 |
| Sample rate | 100 MHz |
| Vid. Filtr | 1.7 usec |
| DAC offset | 1945 |

Transducers used in the experiment included the Matec 1.0 MHz, 2.25 MHz, 5.0 MHz and 10.0 MHz, all being 0.5 inches in diameter. These frequencies were initially chosen because calculation showed that based on the speed of sound in water (1,500 m/s) and the diameter of the sprouts (1–2 mm or 0.001–0.002 m), the resonant frequency across the diameter of the sprout should be in the low MHz range:

velocity=frequency×wavelength frequency=velocity÷wavelength=1,500 m/s 0.001 m 1.5 MHz Sprout #1 was excised from the pea halves, and was placed between two 2.25 MHz transducers, coupled with a thin coat of EKG gel. The Tb 1000 was set on scan increments of 0.005 MHz, and the sprout was scanned from the lowest (50 KHz) frequency available on the system to the highest (20 MHz). Variations in amplitude were observed during this frequency sweeping process, and the low MHz region was quickly identified as the highest amplitude region. Further frequency sweeping revealed maximum amplitude at 1.7 MHz.

The same procedure was followed for test sprout #2 and #3. Test sprout #2 was still attached to half of the pea, and the resonant frequency of 1.64 MHz was detected from the entire structure, although the gain had to be increased because of the attenuation of the acoustic field by the pea half Sprout #3 was an isolated sprout such as #1 and revealed a resonant frequency of 1.78 MHz.

The same procedure was repeated with the 1.0 MHz transducer and similar results were obtained. Thus, it was concluded that the acoustic resonant frequency for 4–5 day old sugar snap pea sprouts was 1.7 MHz±0.1 MHz. Having successfully identified a resonant frequency for a multicellular biological, the next step was to show disruption and/or augmentation effects from the application of an acoustic field at this frequency.

A number of germination tests were conducted using different power levels or voltages and length of exposure at the acoustic resonant frequency.

GERMINATION #1

A Matec 1.0 MHz transducer was used with the Tb 1000 system having the same settings as that described above in determining the acoustic resonant frequency except:

| Frequency | 1.7 MHz |
|---|---|
| Voltage | High |
| Rep. Rate | 10 msec |
| Pulse Width | 2 μsec |
| Through Mode | |

Two small plastic dishes were prepared with sterile cotton balls in a single layer in the bottom of the dishes with seven sugar snap pea seeds and filled with distilled water to cover the pea seeds halfway. The pea seeds in one dish served as a control. The 1.0 MHz transducer was clamped tightly in a ring stand clamp, and the face of the transducer was lowered into the center of the dish. The acoustic field of the transducer was lowered into the center of the dish. The acoustic field was initiated on day one and interrupted several times during the next 72 hours due to frequent storms in the area. The transducer was operating approximately only 18 hours during the first 48 hours of the test.

The experiment was terminated on day five. All seven of the acoustic pea seeds sprouted, while only five of the control pea seeds sprouted. Several spots of black mold were noted in the control dish. Comparison of the root sprouts revealed that the acoustic sprouts were twice as long as the control sprouts (2.9 cm vs. 1.6 cm). Interpretation of these results was ambiguous because of the tight clamping of the transducer, the frequent and repeated interruption of the acoustic field and the contaminating mold in the control dish. Accordingly, test trays were constructed with the transducer coming up through the bottom of the tray.

GERMINATION #2

The same acoustic equipment and setup was used in this germination as that used in germination #1. The 1.0 MHz transducer was clamped loosely in a ring stand clamp, and the face of the transducer was lowered into a larger plastic dish. A second 1.0 MHz transducer, unconnected to the signal generator was lowered into a larger control dish. Interruptions were infrequent.

The study was terminated on day #7. In the control dish, 79% had sprouted and the average root sprout length was 3.95 cm (n=81.) In the acoustic dish, only 69% had sprouted and the average root sprout length was 3.12 cm (n=80). It was concluded that this frequency at the higher power voltage output demonstrated a disruptive effect on pea sprouting and growth. GERMINATION #3

A new setup was implemented wherein the 1 MHz transducer was fitted into the bottom of two dishes which were modified by drilling a hole with rubber seals to accomodate a 0.5 inch diameter transducer. The transducers were placed face up through the bottom of the dish. Each dish was prepared with sterile cotton batting in a single layer in the bottom. Fifty sugar snap pea seeds were placed in the dishes and filled halfway with water. The control dish was prepared exactly as the acoustic dish but unconnected to the signal generator. The acoustic field was initiated on day #1 with the above settings used in germination #1, except that the pulse width was increased to 19.98 usec which was about 10 times the pulse width used in germination #1. It was also 10 times the power output as in experiment #2. Interruptions were infrequent.

The study was terminated on day #7. In the control dish, 82% had sprouted and the average root sprout length was similar to germination #2. In the acoustic dish, only 72% had sprouted and the average root sprout was similar to germination #2. This data confirmed that the frequency of 1.7 MHz at a high power voltage level demonstrated a disruptive effect on pea sprouting and growth.

GERMINATION #4

The same setup was used as that disclosed in germination #3 except:

| Voltage | Low |
|---|---|
| Rep. Rate | 2 μsec |
| Pulse Width | 0.3 μsec (this was adjusted to produce only one sonic wavelength per repetition) |

The results of this germination showed that only 84% of the control dish had sprouted, while in the acoustic dish, 90% had sprouted. The average root sprout length of the acoustic peas was 24% longer than the control peas. It was concluded that this frequency and a lower power acoustic field has an augmenting effect on the pea sprouting and growth. GERMINATION #5

The same setup and experiment disclosed in germination #4 was repeated with similar results. In the control dish, 84% had sprouted, while in the acoustic dish, 96% had sprouted. The average root sprout length of the acoustic peas was 30% longer than the control peas (3.26 cm vs. 2.49 cm). It was confirmed that the acoustic resonant frequency at low power had an augmenting effect on the growth of the peas.

The results of the above five germination tests, shown in Table 3, confirmed that acoustic resonant energy can have both an disruptive and augmenting effect depending on the length of exposure and power intensity of exposure. Also, it was concluded that the tight clamping of the transducer in gemination #1 must have damped and attenuated the power output from the transducer to mimic low power effect.

TABLE 3

| # | Frequency | Power Voltage | Rep. Rate msec | Pulse Width usec | Transducer Position | Sprouting Results % A | C* |
|---|---|---|---|---|---|---|---|
| 1 | 1.7 MHz | High | 10.00 | 2.0 | clamped | 100 | 75 |
| 2 | 1.7 MHz | High | 10.00 | 2.0 | clamped | 69 | 79 |
| 3 | 1.7 MHz | High | 10.00 | 19.98 | bottom | 72 | 82 |
| 4 | 1.7 MHz | Low | 13.00 | 0.3 | bottom | 90 | 84 |
| 5 | 1.7 MHz | Low | 13.00 | 0.3 | bottom | 96 | 84 |

*A and C define the percentage rates of survival and growth of Acoustic (A) and Control (C) peas.

GERMINATION #6

Germination trays were prepared by placing sterile cotton in the bottom of round plastic bowls equipped with acoustic transducers in the bottom. Seventy-five peas (Sugar snap, Lake Valley lot A2B 1997) were placed in each tray and distilled water was added as needed. An acoustic field was delivered to one group of peas for three days using a Matec 1.0 MHz transducer with a repetition rate of 10 msec having a pulse width of 2 μsec. The peas were then transferred to 6 inch diameter tapered black plastic pots, filled with plant growing medium, having bottom openings for water drainage. Three peas were planted in each container.

The peas were grown indoors with a 1000 watt growlight. The peas grew to maturity and into plants bearing pea pods which were measured and weighed. Table 4 provides information relating to the overall growth pattern of the mature pea plants.

TABLE 4

| | Acoustic Exposed Peas | Control Peas |
|---|---|---|
| Number of Mature Plants | 64 | 54 |
| Percent Plants | 119% | 100% |
| Number of Pods from Mature Plants | 307 | 287 |
| Percent Pods | 107% | 100% |
| Average Plant Length | 81 inches | 80 inches |
| Weight of Peas | 3.7oz. | 3.1oz. |
| Percent Weight | 119% | 100% |
| Weight per Plant | 0.058oz. | 0.057oz. |
| Volume of Peas | 160 ml | 130 ml |
| Percent Volume | 123% | 100% |

Conclusion—The acoustically treated peas had approximately 20% greater weight and volume of peas. Weight of peas per plant was identical between the two groups. Hence, the acoustic treatment affected crop yield indirectly, by increasing germination. The acoustic treatment during the first three days affected germination only, and did not affect the subsequent growth and crop yield after the acoustic field was discontinued.

GERMINATION #7

DAY 1 Germination trays (2) were prepared as above in germination #6 with 115 peas per tray. Neither tray was equipped with acoustic transducers. In this experiment, peas contained in one of the prepared trays were induced into acoustic resonance by an acousto-EM field which was delivered via exposure in a shielded room using a 20 foot antenna and an E field generator. EM energy at a frequency of 1.7 MHz was applied continuously at a power of 8.5 volts/m. The tray containing the control peas was kept in a second shielded room without exposure to an acousto-EM field.

DAY 3–11 of the peas exposed to the acousto-EM field sprouted while only 5 of the control peas sprouted. The acousto-EM exposed peas were almost twice the length of the control peas.

DAY 6–45 of the peas exposed to the acousto-EM field had sprouted while only 35 of the control group had sprouted.

DAY 10–61 of the peas exposed to the acousto-EM field had sprouted while only 45 of the control group had sprouted. The average length of the leaf sprout on the exposed acousto-EM field group was 3,3 cm while the average length of the control group was only 2.7 cm.

RESULTS: Applying an acousto-EM signature augmented the germination and growth rate of the peas.

Example 11

Detection and Identification of Inorganic Structures

The methods and systems of the present invention have a wide range of useful applications, such as on-site identification both qualitatively and quantitatively of various types of inorganic matter or structures, recognition of impurities in metal alloys, recognition of armaments and weapons, such as plastic explosives, etc.

Detection and identification can be achieved by applying acoustic energy at a frequency closely matching the resonant frequency of an object or structure thereby inducing acoustic resonance therein for detection of a unique acoustic and/or acousto-EM signature. Using methods known to those skilled in the art, any device capable of generating and transmitting acoustic energy through any medium can be used to generate the resonant acoustic and/or acousto-EM signatures utilized by this invention including the apparatus disclosed and shown above in FIG. 1.

Using methods known to those skilled in the art, any device capable of detecting and analyzing acoustic energy and/or EM energy through any medium can be used to detect the resonant acoustic and/or acousto-EM signatures utilized by the invention such as disclosed and shown above in FIG. 2.

The system shown in FIG. 12 gives a schematic overview of the necessary components to be utilized in determining resonant acoustic frequencies of different inorganic materials or structures. Predetermination of the specific frequencies and acoustic and/or acousto-EM signatures will provide a database for later comparisons.

Figure 35A:
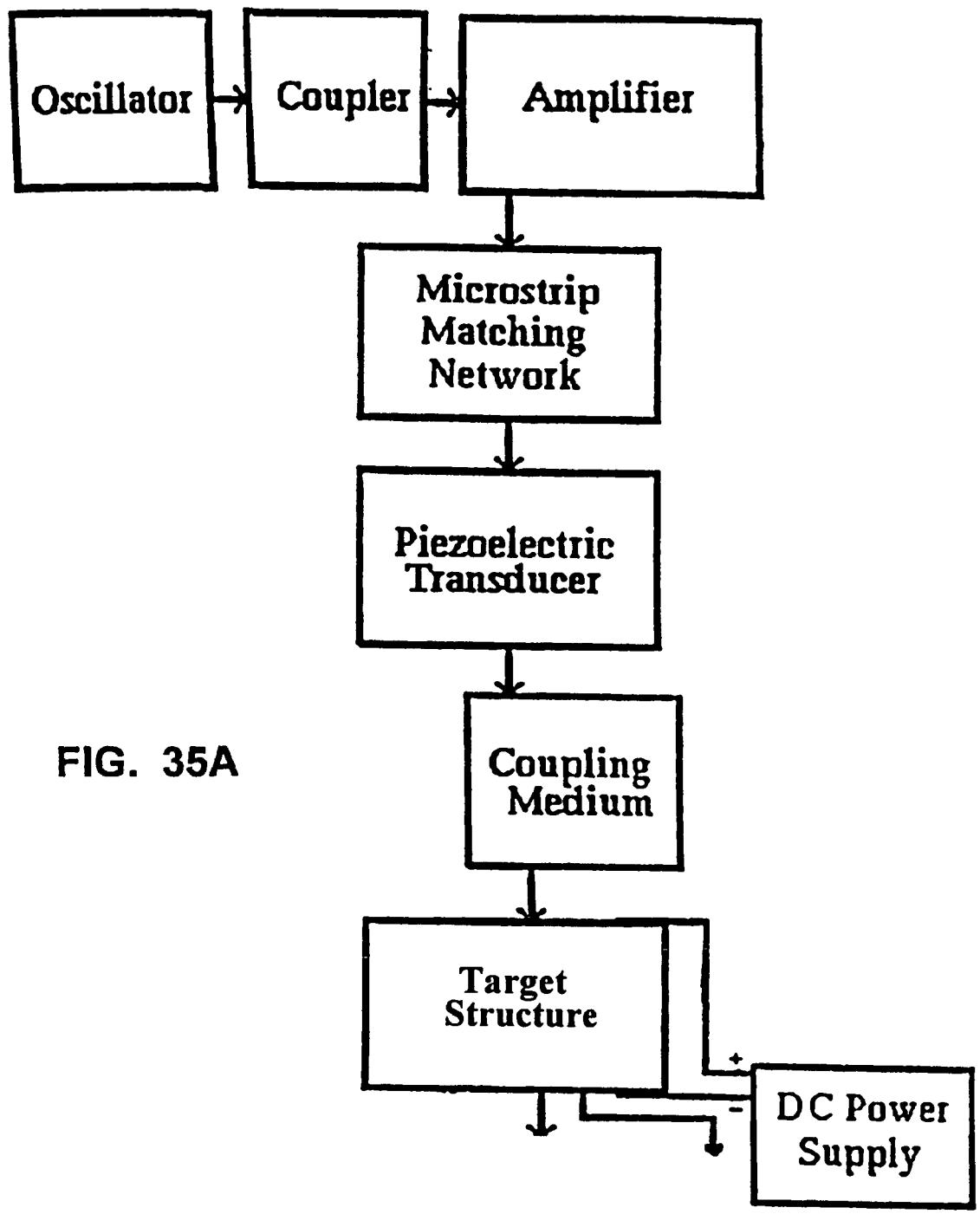
FIGS. 35 A & B are block diagrams showing a method and system for determining acoustic and/or acousto-EM frequencies of inorganic material or structure.
Figure 35B:
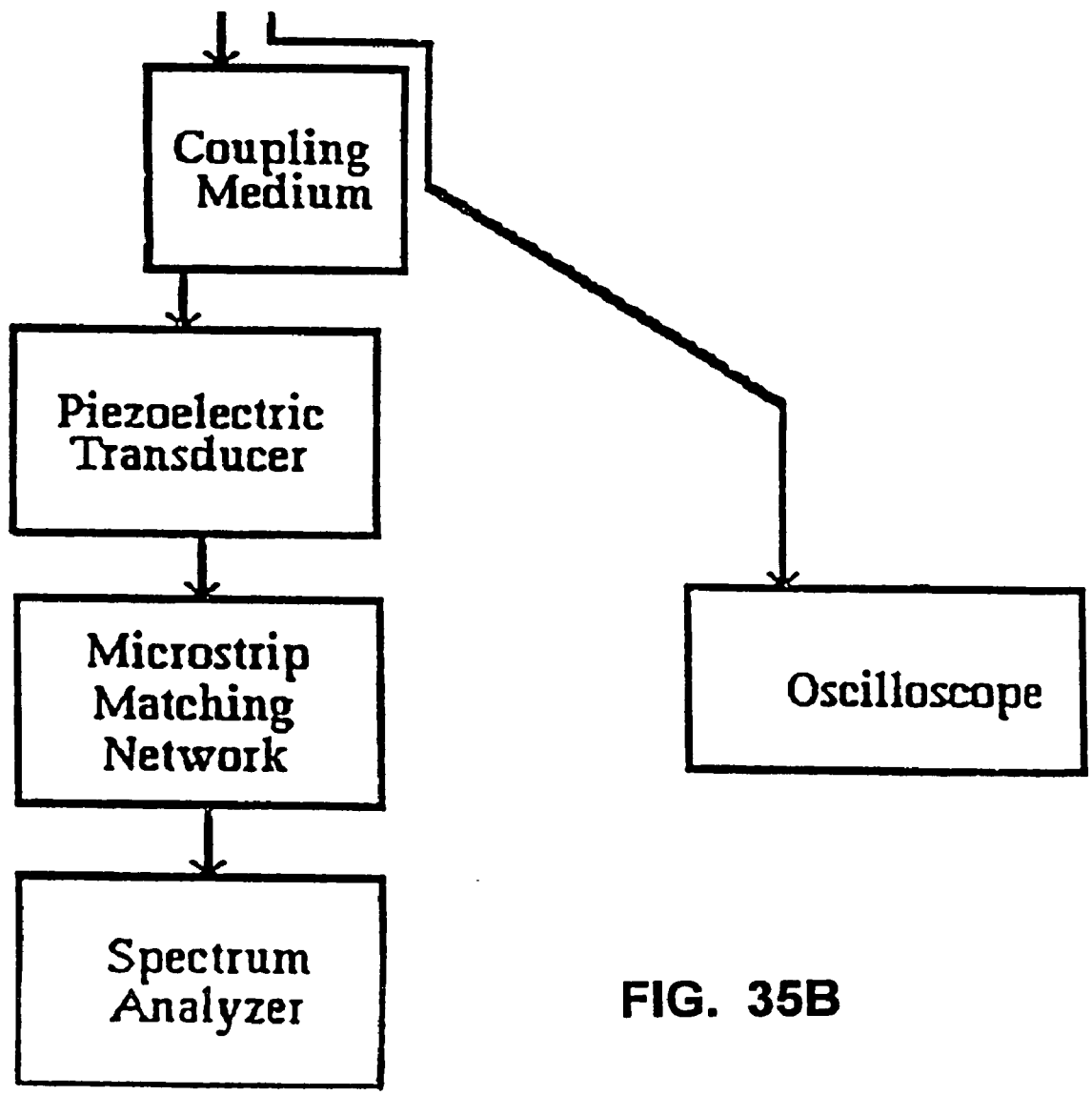

In FIGS. 35 A & B block diagrams show the apparatus setup wherein resonant acoustic energy can be combined with acousto-EM energy for a spectroscopic method to identify, detect and distinguish similar or dis-similar objects. This can be accomplished by stimulating an object to resonance by the use of acoustic energy, electromagnetic energy or both. When the resonant acoustic frequencies are applied to the sample, acoustic resonance is induced and a unique electromagnetic energy pattern is generated, that being the resonant acousto-EM signature. Mechanisms producing the resonant acousto-EM signature may include, but are not limited to piezoelectricity, acoustoelectricity, magnetoacoustics and/or intrinsic energy dissipation. The resonant acousto-EM signature is a manifestation of electromagnetic properties and/or fields including, but not limited to, direct current, alternating current, magnetic field, electric field, EM radiation, and/or acoustic cyclotron resonance.

Analysis is then performed on the resultant acoustic, electromagnetic or combined energy spectrum produced. The distribution of acoustic and electromagnetic frequencies and/or properties is then characterized to describe a unique acoustic and/or acousto-EM signature of the object.

The present invention may be utilized in security systems such as in airports where concerns regarding the transport of plastic explosives or plastic weapons into airlines terminals and carriers are generating increased security surveillance. Metal detectors are not capable of detecting polymers because in most cases the polymers will not respond to the magnetic fields of the device. Likewise, the other alternatives such as X-rays devices or trained animals are not able to distinguish one polymer from another, and therefore, some explosives can be difficult to detect.

A detection device can be used that will recognize the unique acoustic signature and/or acousto-EM signature which characterizes a particular plastic explosive.

To determine the acoustic resonant frequency of the plastic explosive, the natural frequency of the plastic containing the explosive has to be determined first. The method to determine the resonant frequency which in turn determines the frequency needed to induce acoustic resonance includes the following steps. A sample of the plastic having a known quantity of explosive material is placed between two transducers comprising thin slices of thin film zinc oxide on a sapphire substrate available from Teledyne Electronic Technology. The sample is adhered to the transducers by phenyl salicylate, a coupling medium that acts as an adhesive and also allows the transfer of energy. One of the transducers is connected to a Teledyne Microstrip Matching Network, which is an impedance matching device. The impedance matching device is in turn connected to a Hewlett-Packard Model 6286A power source. The other transducer is also connected to a Teledyne Microstrip Matching Network which in turn is connected to a B & K Precision Model 2625 spectrum analyzer. The acoustic signal, of the plastic test sample, transmitted from the transducer is fed into the positive lead of the spectrum analyzer. The known acoustic signals from the testing fluids, holders, transducer material served as a control and are fed into the negative lead of the spectrum analyzer. Using this setup the control signatures are canceled out and the remaining resonant acoustic signature displayed is from the plastic explosive, yielding a qualitative result and a unique signature.

The power source is activated and a range of voltages is transmitted to the transducer. The electrical signal induces a mechanical strain in the transducer material causing an acoustical energy wave in a specific frequency range corresponding to the voltage that is delivered by the power source. This acoustic wave is transmitted through the plastic sample and received by the second transducer. The electrical output from the transducer is converted into a readable format by the spectrum analyzer. The resonant frequency and in turn the resonant acoustic signature can be determined by this method. By varying the voltage from the power source, the amplitude of the transmitted acoustic wave reacts to the different applied voltages. When the amplitude of the signal reaches a maximum, the plastic sample is in acoustic resonance and the frequency that induces this state substantially corresponds to the resonant frequency. At this point, the resonant acoustic and/or acousto-EM signature can be determined.

Once the resonant acoustic signature of the plastic explosive is determined then a test can be conducted with several different types of plastic, some that contained the explosive and some that do not. Again each sample is placed in the same setup as explained above. The previously determined frequency range to induce acoustic resonance in the sample containing the explosive is administered by the power source using the corresponding voltage. The samples are individually tested and only the samples containing explosives reach maximum amplitude at the predetermined acoustic resonant frequency. Using this method a unique signature for a plastic that contains a certain type of explosive can be determined.

Once the qualitative resonant acoustic signature has been determined it can be stored in a microprocessor or other memory storage device for subsequent comparative analysis in a recognition mode. Also once the qualitative resonant acoustic and/or acousto-EM energy signature has been determined, quantitative results may be determined by comparing the resonant acoustic signature amplitudes from samples of known concentration of the plastic explosives. Samples with higher concentrations of plastic explosives will have a higher resonant acoustic signature amplitudes. In turn, a ratio can be derived allowing for assessment of load in the sample of unknown concentration.

Suitcases, packages and people can be scanned at an airport terminal to determine if a plastic explosive is being transported into the terminal or on a carrier. A suitcase can be placed between two transducers, one transducer generates the acoustic signal and sweeps through a wide band of target frequencies, and the other transducer detects the transmitted acoustic signal. The acoustic signal transmitted from the suitcase is fed into the positive lead of a signal analyzer. The known acoustic resonant signatures for leather, paper, fabric, plastics, and other materials that would normally be included in passenger's luggage or carry-on packages are fed into the negative lead of the signal analyzer. Thus the control signatures cancel out their component resonant frequencies in the positive lead sample. The remaining frequencies are analyzed for the acoustic resonant signature of the plastic explosive.

In another embodiment, the electromagnetic energy pattern of the acousto-EM signature of a plastic explosive is transmitted to the suitcase. If an acoustic transducer detects an acoustic signal from within the suitcase which is indicating the material has been induced into acoustic resonance then detection is affirmed. The amplitude of the acoustic signal may provide additional information on the relative size or amount of explosive in the suitcase.

In yet another embodiment the acousto-EM signature of a plastic explosive is transmitted to the suitcase. Both acoustic energy and acousto-EM properties of the contents within the suitcase are measured to detect and identify the plastic explosive.

That which is claimed is:

1. A method for augmenting at least one function of a targeted biologic structure, which comprises targeting the biologic structure by applying to the biologic structure at least one substantially complete acoustic signature of the biologic structure to induce acoustic resonance in the biologic structure.

2. The method of claim 1, wherein said providing comprises applying resonant acousto-EM energy at a sufficient power intensity to augment at least one function of the biologic structure, said at least one function being selected from the group of functions consisting of growth, reproduction, regeneration, embryogenesis, metabolism, fermentation, germination, oxidation or reduction activity and wound healing.

3. The method of claim 1, wherein said biologic structure comprises at least one structure selected from the group of structures consisting of virus, bacteria, fungi, tissue masses, worms, arthropods, chitins, plants, animals, microorganisms, multicellular organisms, protozoa, liver, muscle, feet, brain, kidney, spleen, blood, lung, lens of eye, aqueous humor, vitreous humor, animal cell, plant cell, proteins, molecules, cell wall, capsule, spore, pili, plasma membrane, organ, portions of structures, components of structures, flagellum, crytoplasmic inclusion body, basal body, parasite, appendages, skin, shell, egg, cement/cement plate, bone, DNA, RNA, carbohydrates, lipids, lipopolysaccharides, glycolipids, glycoproteins, proteoglycans, chloroplasts, mitochondria, endoplasmic reticulum, endotoxins, exotoxins, proteases and ligands for host cell receptors.

4. A method for augmenting at least one function of a targeted biologic structure, which comprises targeting the biologic structure by providing to the biologic structure at least one resonant acousto-EM energy of the biologic structure.

5. The method of claim 4, wherein said providing comprises applying at least a portion of an acousto-EM signature of the biologic structure.

6. The method of claim 4, wherein said providing comprises applying at least one substantially complete acousto-EM signature of the biologic structure.

7. The method of claim 4, wherein said providing occurs at a sufficient power intensity to augment at least one function of the biologic structure, said at least one function being selected from the group of functions consisting of growth, reproduction, regeneration, embryogenesis, metabolism, fermentation, germination, oxidation activity, reduction activity and wound healing.

8. The method of claim 4, wherein said biologic structure comprises at least one structure selected from the group of structures consisting of virus, bacteria, fungi, tissue masses, worms, arthropods, chitins, plants, animals, microorganisms, multicellular organisms, protozoa, liver, muscle, feet, brain, kidney, spleen, lung, lens of eye, aqueous humor, vitreous humor, plant cell, proteins, molecules, cell wall, capsule, spore, pili, plasma membrane, organ, portions of structures, components of structures, flagellum, crytoplasmic inclusion body, basal body, parasite, appendages, skin, shell, egg, cement/cement plate, bone, DNA, RNA, carbohydrates, lipids, lipopolysaccharides, glycolipids, glycoproteins, proteoglycans, chloroplasts, mitochondria, endoplasmic reticulum, endotoxins, exotoxins, proteases and ligands for host cell receptors.

9. A method for augmenting at least one function of at least one structure selected from the group of structures consisting of organs, and organisms, which augmenting comprises targeting said at least one structure by inducing acoustic resonance therein.

10. The method of claim 9, wherein said group of structures consisting of organs and organisms comprises at least one member selected from the group consisting of virus, bacteria, fungi, tissue masses, worms, arthropods, chitins, plants, animals, microorganisms, multicellular organisms, protozoa, liver, muscle, feet, brain, kidney, spleen, blood, lung, lens of eye, aqueous humor, vitreous humor, animal cell, plant cell, proteins, molecules, cell wall, capsule, spore, pili, plasma membrane, organ, portions of structures, components of structures, flagellum, crytoplasmic inclusion body, basal body, parasite, appendages, skin, shell, egg, cement/cement plate, bone, DNA, RNA, carbohydrates, lipids, lipopolysaccharides, glycolipids, glycoproteins, proteoglycans, chloroplasts, mitochondria, endoplasmic reticulum, endotoxins, exotoxins, proteases and ligands for host cell receptors.

11. A method for augmenting at least one function of a targeted biologic structure selected from the group consisting of organs and organisms, which comprises targeting the biologic structure by inducing acoustic resonance in the biologic structure with select frequencies that augment the targeted biologic structure but have no substantial deleterious effect on nearby, non-resonating structures.

12. The method of claim 11, wherein said group of structures consisting of organs and organisms comprises at least one member selected from the group consisting of virus, bacteria, fungi, tissue masses, worms, arthropods, chitins, plants, animals, microorganisms, multicellular organisms, protozoa, liver, muscle, feet, brain, kidney, spleen, blood, lung, lens of eye, aqueous humor, vitreous humor, animal cell, plant cell, proteins, molecules, cell wall, capsule, spore, pili, plasma membrane, organ, portions of structures, components of structures, flagellum, crytoplasmic inclusion body, basal body, parasite, appendages, skin, shell, egg, cement/cement plate, bone, DNA, RNA, carbohydrates, lipids, lipopolysaccharides, glycolipids, glycoproteins, proteoglycans, chloroplasts, mitochondria, endoplasmic reticulum, endotoxins, exotoxins, proteases and ligands for host cell receptors.

13. A method for augmenting at least one function of a targeted biologic structure which comprises:
   a) detecting at least one signature of the targeted biologic;
   b) comparing said at least one signature to at least one reference signature; and
   c) targeting the biologic structure by inducing acoustic resonance in the biologic structure.

14. The method of claim 13, wherein said biologic structure comprises at least one structure selected from the group of structures consisting of virus, bacteria, fungi, tissue masses, worms, arthropods, chitins, plants, animals, microorganisms, multicellular organisms, protozoa, liver, muscle, feet, brain, kidney, spleen, blood, lung, lens of eye, aqueous humor, vitreous humor, animal cell, plant cell, proteins, molecules, cell wall, capsule, spore, pili, plasma membrane, organ, portions of structures, components of structures, flagellum, crytoplasmic inclusion body, basal body, parasite, appendages, skin, shell, egg, cement/cement plate, bone, DNA, RNA, carbohydrates, lipids, lipopolysaccharides, glycolipids, glycoproteins, proteoglycans, chloroplasts, mitochondria, endoplasmic reticulum, endotoxins, exotoxins, proteases and ligands for host cell receptors.

15. A system for inducing targeted acoustic resonance in a biologic structure to augment at least one function of the biologic structure comprising:
   a) means for providing to the biologic structure at least one resonant acousto-EM signature of the biologic structure.

16. A method for augmenting the growth of an aquatic species comprising:
   a) determining at least one first resonant frequency of said aquatic species; and
   b) applying said at least one first resonant frequency at a sufficient power intensity to cause said augmenting to occur.

17. The method of claim 16, wherein said determining comprises measuring acoustic resonance frequency profiles.

18. The method of claim 14, wherein said measuring comprises transmitting acoustic energy to said aquatic species with at least one transducer.

19. The method of claim 18, wherein said determining comprises placing said aquatic species adjacent said at least one transducer and scanning said aquatic species with a range of acoustic frequencies.

20. The method of claim 16, further comprising determining at least one second resonant frequency of said aquatic species; and applying said at least one second resonant frequency at a sufficient power intensity to cause further augmenting to occur.

21. The method of claim 20, wherein said at least one second resonant frequency is applied at a later point in time after said aquatic species has grown in size.

22. The method of claim 16, wherein said applying comprises placing at least one transducer in communication with said aquatic species.

23. The method of claim 22, wherein said at least one transducer is placed in at least one wall of an enclosure that contains said aquatic species.

24. The method of claim 16, wherein said augmenting the growth comprises at least one of increasing survivability and increasing growth rate.

25. The method of claim 16, wherein said augmenting comprises increasing survivability and increasing growth rate.

26. The method of claim 16, wherein said aquatic species comprises at least one fish.

27. The method of claim 26, wherein said at least one fish comprises small-fry.

28. The method of claim 16, wherein said at least one fish comprises a plurality of fish contained within an enclosure.

29. A method for augmenting the growth of an aquatic species comprising:
   a) determining at least one first acoustic resonance frequency profile of said aquatic species;
   b) applying at least a portion of said first acoustic resonance frequency profile at a sufficient power intensity to cause said augmenting to occur;
   c) determining and applying at least one second acoustic resonance frequency profile by substantially repeating the steps a) and b) above at a point in time after said aquatic species has grown in size; and
   d) repeating step c) to achieve additional augmentation of said aquatic species.

30. The method of claim 29, wherein said aquatic species comprises at least one fish.

31. The method of claim 30, wherein said at least one fish comprises small-fry.

32. The method of claim 30, wherein said at least one fish comprises a plurality of fish contained within an enclosure.

33. A method for augmenting the growth of a plant species comprising;
   a) determining at least one first resonant acoustic frequency of said plant species by utilizing a frequency sweeping process; and
   b) applying said at least one first resonant acoustic frequency at a sufficient power intensity to cause said augmenting to occur.

34. The method of claim 33, wherein said frequency sweeping process comprises utilizing at least one transducer and at least one signal generator.

35. The method of claim 33, wherein said augmenting the growth comprises at least one of enhancing germination and increasing growth rate.

36. The method of claim 33, wherein said applying comprises placing at least one transducer in communication with said plant species.

37. A method for enhancing germination of a plant species comprising:
   a) determining at least one first resonant acoustic frequency of said plant species by utilizing a frequency sweeping process, and
   b) applying said at least one first resonant frequency at a sufficient power intensity to cause said enhanced germination.

38. A method for enhancing growth of a targeted biologic structure which comprises targeting the biologic structure by applying at least one substantially complete acousto-EM signature of the biologic structure to achieve acoustic resonance in the biologic structure.

39. A method for augmenting the growth of an aquatic species comprising: utilizing at least one acoustic transducer to transmit to said aquatic species at least one first resonant acoustic frequency of said aquatic species, said at least one acoustic transducer operating at a sufficient power intensity to cause said augmenting to occur.

40. The method of claim 39, further comprising transmitting at least one second resonant frequency of said aquatic species at a sufficient power intensity to cause further augmenting to occur.

* * * * *

UNITED STATES PATENT AND TRADEMARK OFFICE
CERTIFICATE OF CORRECTION

| | | |
|---|---|---|
| PATENT NO. | : 7,165,451 B1 | |
| APPLICATION NO. | : 09/786794 | |
| DATED | : January 23, 2007 | |
| INVENTOR(S) | : Juliana H.J. Brooks and Albert E. Abel | |

It is certified that error appears in the above-identified patent and that said Letters Patent is hereby corrected as shown below:

Column 49, lines 43-45 (i.e., Claim 18) should read as follows:

--18. The method of claim 17, wherein said measuring comprises transmitting acoustic energy to said aquatic species with at least one transducer.--

Signed and Sealed this

Fourth Day of December, 2007

JON W. DUDAS
*Director of the United States Patent and Trademark Office*